US00RE42376E

(19) United States
(12) Reissued Patent
Wissner et al.

(10) Patent Number: US RE42,376 E
(45) Date of Reissued Patent: May 17, 2011

(54) SUBSTITUTED 3-CYANOQUINOLINES

(75) Inventors: Allan Wissner, Ardsley, NY (US); Hwei-Ru Tsou, New City, NY (US); Dan M. Berger, New City, NY (US); Middleton B. Floyd, Jr., Suffern, NY (US); Philip R. Hamann, Thiells, NY (US); Nan Zhang, Bayside, NY (US); Philip Frost, Morris Township, NJ (US)

(73) Assignee: Wyeth Holdings Corporation, Madison, NJ (US)

(21) Appl. No.: 12/785,269

(22) Filed: May 21, 2010

Related U.S. Patent Documents

Reissue of:
(64) Patent No.: 6,297,258
Issued: Oct. 2, 2001
Appl. No.: 09/630,270
Filed: Aug. 1, 2000

U.S. Applications:
(63) Continuation of application No. 09/405,868, filed on Sep. 24, 1999, now abandoned.

(60) Provisional application No. 60/150,699, filed on Sep. 29, 1998.

(51) Int. Cl.
*A61K 31/47* (2006.01)
*C07D 215/44* (2006.01)

(52) U.S. Cl. ..... 514/313; 514/228.2; 514/235.2; 514/253.01; 514/278; 514/312; 546/19; 546/153; 546/159; 546/160; 546/171; 544/58.6; 544/128; 544/328; 544/331; 544/363

(58) Field of Classification Search ..... 546/19, 546/153, 159, 160, 171; 544/58.6, 128, 328, 544/331, 363; 514/313, 228.2, 235.2, 253, 514/278, 312
See application file for complete search history.

(56) References Cited

U.S. PATENT DOCUMENTS

| | | | | |
|---|---|---|---|---|
| 5,480,883 | A | 1/1996 | Spada et al. | |
| 5,686,457 | A | 11/1997 | Traxler et al. | |
| 6,002,008 | A | 12/1999 | Wissner et al. | |
| 6,288,082 | B1 * | 9/2001 | Wissner et al. | 514/313 |
| 6,972,288 | B1 * | 12/2005 | Himmelsbach et al. | 514/234.8 |

FOREIGN PATENT DOCUMENTS

| | | |
|---|---|---|
| EP | 0520722 | 12/1992 |
| EP | 0566226 | 10/1993 |
| EP | 0602851 | 6/1994 |
| EP | 0635498 | 1/1995 |
| EP | 0635507 | 1/1995 |
| WO | 9515758 | 6/1995 |
| WO | WO 95/15758 | 6/1995 |
| WO | 9519774 | 7/1995 |
| WO | 9519970 | 7/1995 |
| WO | WO 95/19774 | 7/1995 |
| WO | WO 95/19970 | 7/1995 |
| WO | 9521613 | 8/1995 |
| WO | 9523141 | 8/1995 |
| WO | WO 95/21613 | 8/1995 |
| WO | WO 95/23141 | 8/1995 |
| WO | 9524190 | 9/1995 |
| WO | WO 95/24190 | 9/1995 |
| WO | 9609294 | 3/1996 |
| WO | WO 96/09294 | 3/1996 |
| WO | 9633977 | 10/1996 |
| WO | 9633978 | 10/1996 |
| WO | 9633979 | 10/1996 |
| WO | 9633980 | 10/1996 |
| WO | 9633981 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | 9802434 | 1/1998 |
| WO | 9802438 | 1/1998 |
| WO | WO 98/02434 | 1/1998 |
| WO | WO 98/02438 | 1/1998 |
| WO | 9813350 | 4/1998 |
| WO | WO 98/13350 | 4/1998 |
| WO | 9843960 | 10/1998 |

(Continued)

OTHER PUBLICATIONS

Want, Bioorg & Med Chem Lett, vol. 10, pp. 2477-2480, 2000.*
Bridges et al., Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor, J. Med. Chem. 39:267-276 (1996).
Burke, T.R., "Protein-tyrosine kinase inhibitors," Drugs of the Future 17:119 (1992).
Chang et al., Protein-tyrosine kinase inhibition: mechanism-based discovery of antitumor agents, J. Nat. Prod. 55:1529-1560 (1992).
Dolle et al., 5,7-Dimethoxy-3-(4-pyridinyl)quinoline is a potent and selective inhibitor of human vascular beta-type platelet-derived growth factor receptor tyrosine kinase, J. Med. Chem. 37(17):2627-2629 (1994).

(Continued)

*Primary Examiner* — D. Margaret Seaman
(74) *Attorney, Agent, or Firm* — Jeffrey H. Tidwell; Stephen D. Prodnuk; David Rubin

(57) ABSTRACT

This invention provides compounds of formula I having the structure

1 wherein $G_1$, $G_2$, $R_1$, $R_4$, Z, n, and X are defined in the specification or a pharmaceutically acceptable salt thereof which are useful as antineoplastic agents and in the treatment of polycystic kidney disease.

35 Claims, No Drawings

FOREIGN PATENT DOCUMENTS

| | | | |
|---|---|---|---|
| WO | WO 98/43960 | | 10/1998 |
| WO | 99/61590 | * | 12/1999 |

OTHER PUBLICATIONS

Du et al., Abnormal polarization of EGF receptors and autocrine stimulation of cyst epithelial growth in human ADPKD, Am. J. Physiol. 269(2 Pt 1):487-495 (1995).
Fry et al., A specific inhibitor of the epidermal growth factor receptor tyrosine kinase, Science 19:265(5175):1093-1095 (1994).
Gattone et al., Epidermal growth factor ameliorates autosomal recessive polycystic kidney disease in mice, Dev. Biol 169(2):504-510 (1995).
Gazit et al., Tyrphostins. 5. Potent inhibitors of platelet-derived growth factor receptor tyrosine kinase: structure-activity relationships in quinoxalines, quinolines, and indole tyrphostins, J. Med. Chem., 39(11):2170-2177 (1996).
Ife et al., Reversible inhibitors of the gastric (H+/K+)-ATPase. 3. 3-substituted-4-(phenylamino)quinolines, J. Med. Chem. 35(18):3413-3422 (1992).
Maguire et al., A new series of PDGF receptor tyrosine kinase inhibitors: 3-substituted quinoline derivatives, J. Med. Chem. 37:2129-2137 (1994).
Nauta et al., Biliary epithelial cells from mice with congenital polycystic kidney disease are hyperresponsive to epidermal growth factor, Pediatr. Res. 37(6):755-763 (1995).
Wilson et al., Autocrine, endocrine and paracrine regulation of growth abnormalities in autosomal dominant polycystic kidney disease, Eur. J. Cell Biol. 61(1):131-138 (1993).
Chang, C.J. et al., *J. Nat. Prod.,* 55, 1529 (1992).
Du J. et al., *Am. J. Physiol.,* 269 (2 Pt 1), 487 (1995).
Nauta J. et al., *Pediatric Research,* 37(6), 755 (1995).
Gattone, V.H. et al., *Developmental Biology,* 169(2), 504 (1995).
Wilson, P.D. et al., *Eur. J. Cell. Biol.,* 61(1), 131 (1993).
Ife, R.J. et al., *J. Med. Chem.,* 35(18), 3413 (1992).
Gazit, A. et al., *J. Med. Chem.,* 35(11), 2170 (1996).
Dolle, R.E. et al., *J. Med. Chem.,* 372, 2627, (1994).
Maguire, M.P. et al., *J. Med. Chem.,* 37, 2129 (1994).
Fry, D.W. et al., *Science,* 265, 1093 (1994).
Rewcastle, A.J. et al., *J. Med. Chem.,* 39, 267, (1996).
Bridges, A.J. et al., *J. Med. Chem.,* 39, 267 (1996).

* cited by examiner

SUBSTITUTED 3-CYANOQUINOLINES

Matter enclosed in heavy brackets [ ] appears in the original patent but forms no part of this reissue specification; matter printed in italics indicates the additions made by reissue.

This is a continuation of application Ser. No. 09/405,868 filed on Sep. 24, 1999 now abandoned which application claims the benefit of U.S. Provisional Application No. 60/150,699 filed Sep. 29, 1998; the entire disclosure of each of these applications is incorporated by reference herein.

BACKGROUND OF THE INVENTION

This invention relates to certain substituted 3-cyano quinoline compounds as well as the pharmaceutically acceptable salts thereof. The compounds of the present invention inhibit the action of certain growth factor receptor protein tyrosine kinases (PTK) and other protein kinases thereby inhibiting the abnormal growth of certain cell types. The compounds of this invention are therefore useful for the treatment of certain diseases that are the result of deregulation of these PTKs. The compounds of this invention are anti-cancer agents and are useful for the treatment of cancer in mammals. In addition, the compounds of this invention are useful for the treatment of polycystic kidney disease in mammals. This invention also relates to the manufacture of said 3-cyano quinolines, their use for the treatment of cancer and polycystic kidney disease, and the pharmaceutical preparations containing them.

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated; the result of which is uncontrolled cell proliferation which can lead to tumor growth and ultimately to the disease known as cancer [Wilks A. F., Adv. Cancer Res., 60, 43 (1993) and Parsons, J. T.; Parsons, S. J., Important Advances in Oncology, DeVita V. T. Ed., J. B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers [Slamon, D. J., et. al., Science, 244, 707 (1989) and Science, 235, 1146 (1987)]. Deregulation of EGF-R kinase has been associated with epidermoid tumors [Reiss, M., et. al., Cancer Res., 51, 6254 (1991)], breast tumors [Macias, A., et. al., Anticancer Res., 7, 459 (1987)], and tumors involving other major organs [Gullick, W. J., Brit. Med. Bull., 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Burke. T. R., Drugs Future, 17, 119 (1992) and Chang, C. J.; Geahlen, R. L., J. Nat. Prod., 55, 1529 (1992)]. The compounds of this invention inhibit the kinase activity of EGF-R and are therefore useful for treating certain disease states, such as cancer, that result, at least in part, from deregulation of this receptor. The compounds of this invention are also useful for the treatment and prevention of certain precancerous conditions, such as the growth of colon polyps, that result, at least in part, from deregulation of this receptor.

It is also known that deregulation of EGF receptors is a factor in the growth of epithelial cysts in the disease described as polycystic kidney disease [Du J., Wilson P. D., Amer. J. Physiol., 269(2 Pt 1), 487 (1995); Nauta J., et al., Pediatric Research, 37(6), 755 (1995); Gattone V. H., et al., Developmental. Biology, 169(2), 504 (1995); Wilson P. D., et al., Eur. J. Cell Biol., 61(1), 131, (1993)]. The compounds of this invention, which inhibit the catalytic function of the EGF receptors, are consequently useful for the treatment of this disease.

The mitogen-activated protein kinase (MAPK) pathway is a major pathway in the cellular signal transduction cascade from growth factors to the cell nucleus. The pathway involves kinases at two levels: MAP kinase kinases (MAPKK), and their substrates MAP kinases (MAPK). There are different isoforms in the MAP kinase family. (For review, see Rony Seger and Edwin G. Krebs, FASEB, Vol. 9, 726, June 1995). The compounds of this invention can inhibit the action of two of these kinases: MEK, a MAP kinase kinase, and its substrate ERK, a MAP kinase. MEK is activated by phosphorylation on two serine residues by upstream kinases such as members of the raf family. When activated, MEK catalyzes phosphorylation on a threonine and a tyrosine residue of ERK. The activated ERK then phosphorylates and activates transcription factors in the nucleus, such as fos and jun, or other cellular targets with PXT/SP sequences. ERK, a p42 MAPK is found to be essential for cell proliferation and differentiation. Overexpression and/or over-activation of Mek or ERK has been found to be associated with various human cancers (For example, Vimala S. Sivaraman, Hsien-yu Wang, Gerard J. Nuovo, and Craig C. Malbon, J. Clin. Invest. Vol. 99, No. 7 April 1997). It has been demonstrated that inhibition of MEK prevents activation of ERK and subsequent activation of ERK substrates in cells, resulting in inhibition of cell growth stimulation and reversal of the phenotype of ras-transformed cells (David T. Dudley, Long Pang, Stuart J. Decker, Alexander J. Bridges, and Alan R. Saltiel, PNAS, Vol. 92, 7686, August 1995). Since, as demonstrated below, the compounds of this invention can inhibit the coupled action of MEK and ERK, they are useful for the treatment of diseases such as cancer which are characterized by uncontrolled cell proliferation and which, at least in part, depend on the MAPK pathway.

Epithelial Cell Kinase (ECK) is a receptor protein tyrosine kinase (RPTK) belonging to the EPH (Erythropoietin Producing Hepatoma) family. Although originally identified as an epithelial lineage-specific tyrosine kinase, ECK has subsequently been shown to be expressed on vascular endothelial cells, smooth muscle cells, and fibroblasts. ECK is a type I transmembrane glycoprotein with the extracellular ligand-binding domain consisting of a cysteine-rich region followed by three fibronectin type III repeats. The intracellular domain of ECK possesses a tyrosine kinase catalytic domain that initiates a signal transduction cascade reflecting the ECK function. ECK binds and is subsequently activated by its counter-receptor, Ligand for Eph-Related Kinase (LERK)-1, which is an immediate early response gene product readily inducible in a lineage-unrestricted manner with proinflammatory cytokines such as IL-1 or TNF. Soluble LERK-1 has been shown to stimulate angiogenesis in part by stimulating ECK in a murine model of corneal angiogenesis. Unlike their normal counterparts, tumor cells of various lineages constitutively express LERK-1 and this expression can further be upregulated by hypoxia and proinflammatory cytokines. Many of these tumor cells also express ECK at higher levels than their normal counterparts, thereby creating an opportunity for autocrine stimulation via ECK: LERK-1 interaction. The increased expression of both ECK and LERK-1 has been correlated with the transformation of melanomas from the noninvasive horizontal phase of growth into very invasive vertically growing metastatic melanomas. Together, the ECK: LERK-1 interaction is believed to promote tumor growth via its tumor growth promoting and angiogenic effects. Thus, the inhibition of the ECK tyrosine kinase activity mediating signaling cascade induced by its binding and cross-linking to LERK-1 may be therapeutically beneficial in cancer, inflammatory diseases, and hyperproliferative disorders. As is shown below, the compounds of this invention inhibit the tyrosine kinase activity of ECK and are therefore useful for the treatment of the aforementioned disorders.

Growth of most solid tumors is dependent on the angiogenesis involving activation, proliferation and migration of vascular endothelial cells and their subsequent differentiation into capillary tubes. Angiogenization of tumors allows them access to blood-derived oxygen and nutrients, and also provides them adequate perfusion. Hence inhibiting angiogenesis is an important therapeutic strategy in not only cancer but also in a number of chronic diseases such as rheumatoid arthritis, psoriasis, diabetic retinopathy, age-related macular degeneration, and so on. Tumor cells produce a number of angiogenic molecules. Vascular Endothelial Growth Factor (VEGF) is one such angiogenic factor. VEGF, a homodimeric disulfide-linked member of the PDGF family, is an endothelial cell-specific mitogen and is known to cause profound increase in the vascular endothelial permeability in the affected tissues. VEGF is also a senescence-preventing survival factor for endothelial cells. Almost all nucleated tissues in the body possess the capability to express VEGF in response to various stimuli including hypoxia, glucose deprivation, advanced glycation products, inflammatory cytokines, etc. Growth-promoting angiogenic effects of VEGF are mediated predominantly via its signaling receptor Kinase insert Domain containing Receptor (KDR). The expression of KDR is low on most endothelial cells; however, activation with angiogenic agents results in a significant upregulation of KDR on endothelial cells. Most angiogenized blood vessels express high levels of KDR. KDR is a receptor protein tyrosine kinase with an extracellular VEGF-binding domain consisting of 7 immunoglobulin-like domains and a cytoplasmic domain containing the catalytic tyrosine kinase domain split by a kinase-insert region. Binding to VEGF causes dimerization of KDR resulting in its autophosphorylation and initiation of signaling cascade. Tyrosine kinase activity of KDR is essential for mediation of its functional effects as a receptor for VEGF. Inhibition of KDR-mediated functional effects by inhibiting KDR's catalytic activity is considered to be an important therapeutic strategy in the treatment of angiogenized disease states including cancer. As is shown below, the compounds of this invention inhibit the tyrosine kinase activity of KDR and are therefore useful for the treatment of the aforementioned disease states.

In addition to the above utilities some of the compounds of this invention are useful for the preparation of other compounds of this invention.

The compounds of this invention are certain substituted 3-cyano quinolines. Throughout this patent application, the quinoline ring system will be numbered as indicated in the formula below; the numbering for the quinazoline ring system is also shown:

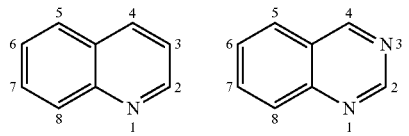

No 3-cyano quinolines have been reported that have biological activity as inhibitors of protein tyrosine kinases. A 3-cyano quinoline with a 4-(2-methyl anilino) substituent having gastric ($H^+/K^+$)-ATPase inhibitory activity at high concentrations has been described [Ife R. J., et al., J. Med. Chem., 35(18), 3413 (1992)].

There are quinolines that do not have the 3-cyano substituent and, unlike the compounds of this invention, are unsubstituted at the 4-position but are reported to be inhibitors of protein tyrosine kinases [Gazit A., et al., J. Med. Chem., 39(11), 2170 (1996)]. A series of quinolines that have a 3-pyridyl substituent and no substituent at the 4-position have been described as inhibitors of platelet derived growth factor receptor kinase [Dolle R. E., et al., J. Med. Chem., 372, 2627 (1994) and Maguire M. P., et al., J. Med. Chem., 372, 129 (1994)]. The patent applications WO 96/09294 and WO-9813350 describe inhibitors of protein tyrosine kinases that include 4-anilino quinolines with a large variety of substituents on positions 5-8 but which must also have a hydrogen or fluorine atom at position 3. The U.S. Pat. No. 5,480,883 describes quinoline derivatives that are inhibitors of protein tyrosine kinases but these derivatives do not have the unique combination of substituents, including the 3-cyano group, contained in the compounds of the present invention. The applications WO-9802434 and WO-9802438 describe quinoline derivatives that are tyrosine kinase inhibitors but these quinolines do not have the important 3-cyano substituent.

In addition to quinolines, certain quinazoline derivatives that are similar, in some respects, to the compounds of this invention are known to be inhibitors of protein tyrosine kinases. The application EP-520722 describes 4-anilinoquinazolines that contain simple substituents such as chloro, trifluoromethyl, or nitro groups at positions 5 to 8. The application EP-566226 is similar but with a much larger variety of substituents now allowed at positions 5 to 8. The application WO-9609294 describes compounds with similar substituents at positions 5 to 8 and with the substituent at to 4-position consisting of some polycyclic ring systems. Some simple substituted quinazolines are also described in the applications WO-9524190, WO-9521613, and WO-9515758. The applications EP-602851 and WO-9523141 cover similar quinazoline derivatives where the aryl group attached at position 4 can be a variety of heterocyclic ring structures. The application EP-635498 describes certain quinazoline derivatives that have alkenoylamino and alkynoylamino groups among the substituents at position 6 and a halogen atom at position 7. The application WO-9519774 describes compounds where one or more of the carbon atoms at positions 5-8 can be replaced with heteroatoms resulting in a large variety of bicyclic systems where the left-hand ring is a 5 and 6-membered heterocyclic ring; in addition, a variety of substituents are allowed on the left-hand ring. The application EP-682027-A1 describes certain pyrrolopyrimidine inhibitors of PTKs. The application WO-9519970 describes compounds in which the left-hand aromatic ring of the basic quinazoline structure has been replaced with a wide variety of different heterocyclic rings so that the resulting inhibitors are tricyclic. The application EP-635507 describes quinazolines where an additional 5 or 6-membered heterocyclic ring with optional substitution is fused at positions 5 and 6.

In addition to the aforementioned patent applications, a number of publications describe 4-anilinoquinazolines: Fry, D. W., et. al., Science, 265, 1093 (1994), Rewcastle G. W., et. al., J. Med. Chem., 38, 3482 (1995), and Bridges, A. J., et. al., J. Med. Chem., 39, 267, (1996). There are no publications that describe 3-cyano quinolines as PTK inhibitors.

DESCRIPTION OF THE INVENTION

This invention provides a compound of formula 1:

1

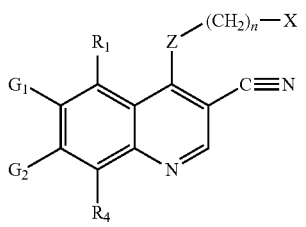

wherein:

X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylarnino, alkanoylamino of 1-6 carbon atoms, alkenoylarnino of 3-8 carbon atoms, alkynoylamino of 3-8 carbon atoms, carboxyalkyl of 2-7 carbon atoms, carboalkoxyalky of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino;

Z is —NH—, —O—, —S—, or —NR—;

R is alkyl of 1-6 carbon atoms, or carboalkyl of 2-7 carbon atoms;

$G_1$, $G_2$, $R_1$, and $R_4$ are each, independently, hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,

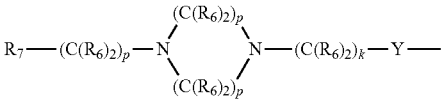

$R_8R_9$—CH—M—$(C(R_6)_2)_k$—Y—, $R_7$—$(C(R_6)_2)_g$—Y—, $R_7$—$(C(R_6)_2)_p$—M—$(C(R_6)_2)_k$—Y—, or Het-$(C(R_6)_2)_q$—W—$(C(R_6)_2)_k$—Y— with the proviso that either $G_1$ or $G_2$ or both $G_1$ and $G_2$ must be a radical selected from the group

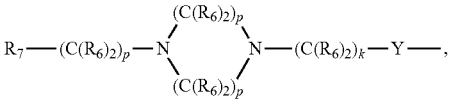

$R_8R_9$—CH—M—$(C(R_6)_2)_k$—Y—, $R'_7$—$(C(R_6)_2)_g$—Y—, $R_7$—$(C(R_6)_2)_p$—M—$(C(R_6)_2)_k$—Y—, Het-$(C(R_6)_2)_q$—W—$(C(R_6)_2)_k$—Y—, or $R_2$—$\overset{H}{N}$—;

Y is a divalent radical selected from the group consisting of

—$(CH_2)_a$—, —O—, and —$\underset{R_6}{N}$—;

$R_7$ is —$NR_6R_6$, —J, —$OR_6$, —$N(R_6)_3^+$, or —$NR_6(OR_6)$;

$R'_7$ is —$NR_6(OR_6)$, —$N(R_6)_3^+$, alkenoxy of 1-6 carbon atoms, alkynoxy of 1-6 carbon atoms, alkynoxy of 1-6 carbon atoms, N-alkyl-N-alkenylamino of 4 to 12 carbon atoms, N,N-dialkenylamino of 6-12 carbon atoms, N-alkyl-N-alkynylamino of 4 to 12 carbon atoms, N-alkenyl-N-alkynylamino of 4 to 12 carbon atoms, or N,N-dialkynylamino of 6-12 carbon atoms with the proviso that the alkenyl or alkynyl moiety is bound to a nitrogen or oxygen atom through a saturated carbon atom;

M is >$NR_6$, —O—, >N—$(C(R_6)_2)_pNR_6R_6$, or >N—$(C(R_6)_2)_p$—$OR_6$;

W is $>NR_6$, —O— or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane tetrahydropyran, and

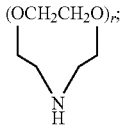

wherein the heterocycle is optionally mono- or di-substituted on carbon or nitrogen with $R_6$, optionally mono- or di-substituted on carbon with hydroxy, $—N(R_6)_2$, or $—OR_6$, optionally mono or di-substituted on carbon with the mono-valent radicals $—(C(R_6)_2)_s OR_6$ or $—(C(R_6)_2)_sN(R_6)_2$, or optionally mono or di-substituted on a saturated carbon with divalent radicals —O— or $—O(C(R_6)_2)_sO—$;

$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxyniethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;

$R_2$, is selected from the group consisting of

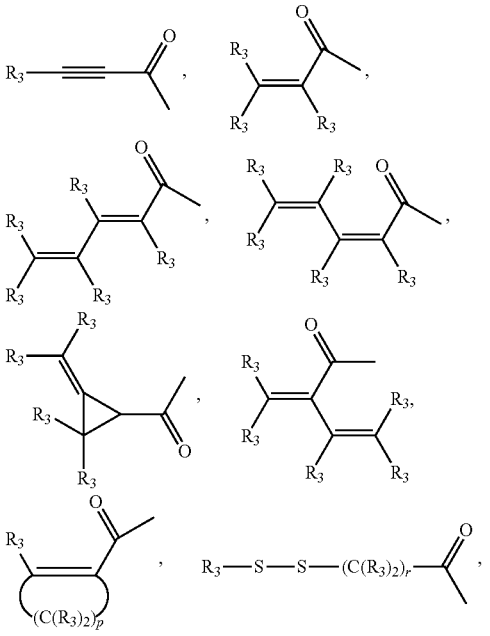

-continued

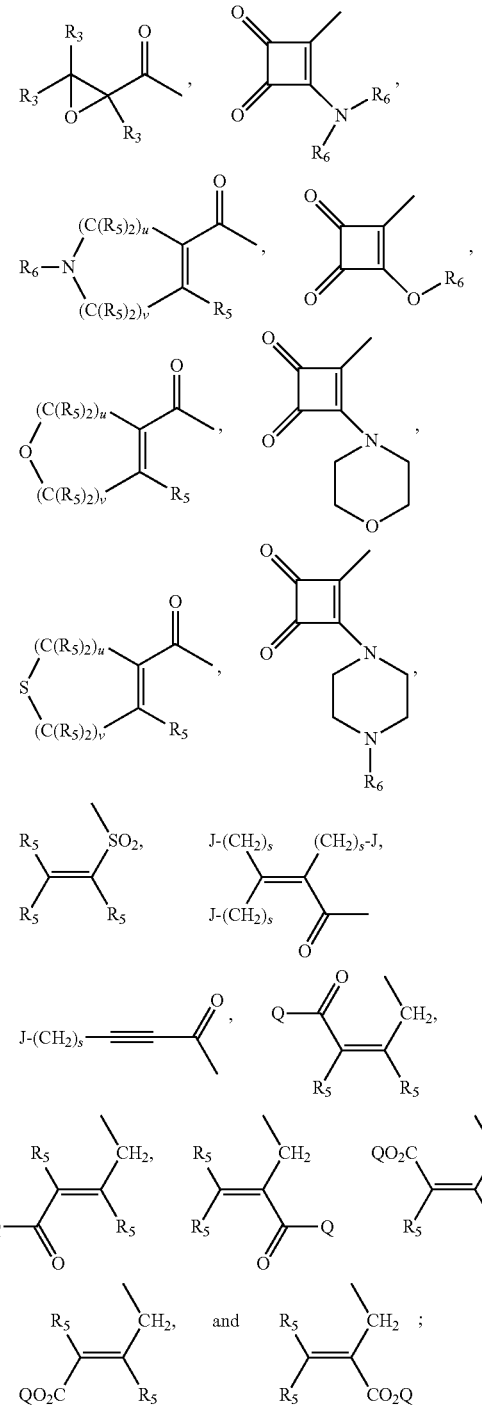

$R_3$ is independently hydrogen, alkyl of 1-6 carbon atoms, carboxy, carboalkoxy of 1-6 carbon atoms, phenyl, carboalkyl of 2-7 carbon atoms,

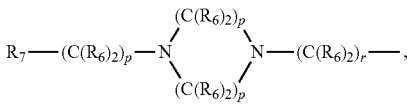

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

with the proviso that at least one of the $R_3$ groups is selected from the group

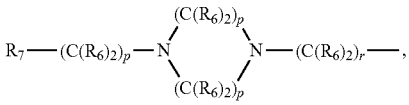

$R'_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R^5$ is independently hydrogen, alkyl of 1-6 carbon atoms, carboxy, carboalkoxy of 1-6 carbon atoms, phenyl, carboalkyl of 2-7 carbon atoms,

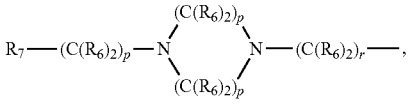

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_rNR_6R_6$, or —$(C(R_6)_2)_rOR_6$;

J is independently hydrogen, chlorine, fluorine, or bromine;

Q is alkyl of 1-6 carbon atoms or hydrogen;

a=0 or 1;

g=1-6;

k=0-4;

n is 0-1;

p=2-4;

q=0-4;

r=1-4;

s=1-6;

u=0-4 and v=0-4, wherein the sum of u+v is 2-4;

or a pharmaceutically acceptable salt thereof, provided that when $R_6$ is alkenyl of 2-7 carbon atoms or alkynyl of 2-7 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^+$, or —$NR_6(OR_6)$, then g=2-6;

when M is —O— and $R_7$ is —$OR_6$, then p=1-4;

when Y is —$NR_6$—, then k=2-4;

when Y is —O— and M or W is —O—, then k=1-4;

when W is not a bond with Het bonded through a nitrogen atom, then q=2-4;

and when W is a bond with Het bonded through a nitrogen atom and Y is —O— or —$NR_6$—, then k=2-4.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The alkyl portion of the alkyl, alkoxy, alkanoyloxy, alkoxymethyl, alkanoyloxymethyl, alkylsulphinyl, alkylsulphonyl, aminoalkyl, N-alkylaminoalkyl, N,N-dialkylaminoalkyl, N-alkylaminoalkoxy, N,N-dialkylaminoalkoxy, alkylsulfonamido, carboalkoxy, carboalkyl, carboxyalkyl, carboalkoxyalkyl, alkanoylamino, N-alkylcarbamoyl, and N,N-dialkylcarbamoyl substituents include both straight chain as well as branched carbon chains. The alkenyl portion of the alkenyl, alkenoyloxymethyl, alkenyloxy, alkenylsulfonamido, substituents include both straight chain as well as branched carbon chains and one or more sites of unsaturation and all possible configurational isomers. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —$CO_2H$ radical. Carboalkoxy of 2-7 carbon atoms is defined as a —$CO_2R''$ radical, where R" is an alkyl radical of 1-6 carbon atoms. Carboxyalkyl is defined as a $HO_2C$—R'" radical where R'" is a divalent alkyl radical of 1-6 carbon atoms. Carboalkoxyalkyl is defined as a R"$O_2C$—R'"— radical where R'" is a divalent akyl radical and where R" and R'" together have 2-7 carbon atoms. Carboalkyl is defined as a —COR" radical, where R" is an alkyl radical of 1-6 carbon atoms. Alkanoyloxy is defined as a —OCOR" radical, where R" is an alkyl radical of 1-6 carbon atoms. Alkanoyloxymethyl is defined as R"$CO_2CH_2$— radical, where R" is an alkyl radical of 1-6 carbon atoms. Alkoxymethyl is defined as R"$OCH_2$— radical, where R" is an alkyl radical of 1-6 carbon atoms. Alkylsulphinyl is defined as R"SO— radical, where R" is an alkyl radical of 1-6 carbon atoms. Alkylsulphonyl is defined as R"$SO_2$— radical, where R" is an alkyl radical of 1-6 carbon atoms. Alkylsulfonamido, alkenylsulfonamido, alkynylsulfonamido are defined as R"$SO_2NH$— radical, where R" is an alkyl radical of 1-6 carbon atoms, an alkenyl radical of 2-6 carbon atoms, or an alkynyl radical of 2-6 carbon atoms, respectively. N-alkylcarbamoyl is defined as R"NHCO— radical, where R" is an alkyl radical of 1-6 carbon atoms. N,N-dialkylcarbamoyl is defined as R" R'NCO— radical, where R" is an alkyl radical of 1-6 carbon atoms, R' is an alkyl radical of 1-6 carbon atoms and R', and R" may be the same or different. When X is substituted, it is preferred that it is mono-, di-, or tri-substituted, with monosubstituted being most preferred. It is preferred that of the substituents R1 and R4, at least one is hydrogen and it is most preferred that both be hydrogen. It is also preferred that X is a phenyl ring, Z is —NH—, and n=0.

Het is a heterocycle, as defined above which may be optionally mono- or di-substituted with $R_6$ on carbon or nitrogen, optionally mono- or di-substituted on carbon with hydroxy, —$N(R_6)_2$, or —$OR_6$, optionally mono or di-substituted on carbon with with —$(C(R_6)_2)_sOR_6$ or —$(C(R_6)_2)_sN(R_6)_2$, and optionally mono or di-substituted on a saturated carbon with divalent radicals —O— or —$O(C(R_6)_2)_sO$— (carbonyl and ketal groups, respectively); in some cases when Het is substituted with —O— (carbonyl), the carbonyl group can be hydrated. Het may be bonded to W when q=0 via a carbon atom on the heterocyclic ring, or when Het is a nitrogen containing heterocycle which also contains a saturated carbon-nitrogen bond, such heterocycle may be bonded to carbon, via the nitrogen when W is a bond. When q=0 and Het is a nitrogen containing heterocycle which also contains an unsaturated carbon-nitrogen bond, that nitrogen atom of the heterocycle may be bonded to carbon when W is a bond and the resulting heterocycle will bear a positive charge. When Het is substituted with $R_6$, such substitution may be on a ring carbon, or in the case of a nitrogen containing heterocycle, which also contains a saturated carbon-nitrogen, such nitrogen may be substituted with $R_6$ or in the case of a nitrogen containing heterocycle, which also contains an unsaturated carbon-nitrogen, such nitrogen may be substituted with $R_6$ in with case the heterocycle will bear a positive charge. Preferred heterocycles include pyridine, 2,6-disubstituted morpholine, 2,5-disubsti tuted thiomorpholine, 2-substituted imidazole, substituted thiazole, thiazolidine, N-substituted imidazole, N-substituted 1,4-piperazine, N-subsitituted piperadine, dioxane, 1,3-dioxolane, and N-substituted pyrrolidine.

The compounds of this invention may contain one or more asymmetric carbons atoms; in such cases, the compounds of this invention include the individual diasteromers, the racemates, and the individual R and S entantiomers thereof. Some of the compound of this invention may contain one or more double bonds; in such cases, the compounds of this invention include each of the possible configurational isomers as well as mixtures of these isomers.

The preparation of the compounds and intermediates of this invention encompassed by Formula 5 is described below in Flowsheet 1 where Z and n are as described above and X' is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkoxy of 1-6 carbon atoms, alkylthio of 1-6 carbon atoms, hydroxy, trifluoromethyl, cyano, nitro, carboxy, carboalkyl of 2-7 carbon atoms, phenoxy, phenyl, thiophenoxy, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, aminomethyl, N-alkylaminomethyl of 2-7 carbon atoms, N,N-dialkylaminomethyl of 3-7 carbon atoms, mercapto, and benzoylamino;

$R_1'$, $R_2'$, $R_3'$, and $R'_4$ are each, independently, hydrogen, halogeno, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, halomethyl, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, trifluoromethyl, cyano, nitro, carboxy, carboalkyl of 2-7 carbon atoms, phenoxy, phenyl, thiophenoxy, benzyl, alkoxyamino of 1-4 carbon atoms, dialkylamino of 2 to 12 carbon atom, N,N-dialkylaminoalkyl of 3-14 carbon atoms, phenylamino, benzylamino, N-alkylcarbamoyl of 1-6 carbon atoms, N,N-dialkylcarbamoyl of 2-12 carbon atoms. According to the sequence of reaction outlined in flowsheet 1, a quinoline-3-carboxylic acid ester of Formula 2 is hydrolyzed with base to furnish a carboxylic acid of Formula 3. The carboxylic acid group of 3 is converted to an acyl imidazole by heating it with carbonyldiimidazole in an inert solvent such as dimethylformamide (DMF) followed by the addition of ammonia to give the amide 4. Dehydration of the amide functional group with a dehydrating agent such as trifluoroacetic anhydride in pyridine, phosphorous pentoxide in an inert solvent, or the like gives the 3-cyano quinolines, 5, of this invention. In those cases where any of the intermediates have an asymmetric carbon atom, they can be used as the racemate or as the individual R or S entantiomers in which case the compounds of this invention will be in the racemic or R and S optically active forms, respectively. The quinoline-3-carboxylic acid esters of Formula 2, the quinoline-3-carboxylic acids of Formula 3, and the quinoline-3-carboxylic amides of Formula 4 needed to prepare the compounds of this invention are either already known to the art or can be prepared by procedures known in the art as detailed in the following references:

Sarges, Reinhard; Gallagher, Andrea; Chambers, Timothy J.; Yeh, Li An, J. Med. Chem., 36, 2828 (1993); Savini, Luisa; Massarelli, Paola; Pellerano, Cesare; Bruni, Giancarlo, Farmaco, 48(6), 805 (1993); Ife, Robert J.; Brown, Thomas H.; Keeling, David J.; Leach, Colin, J. Med. Chem., 35, 3413 (1992); Hanifin, J. William; Capuzzi, Rosemary; Cohen, Elliott, J. Med. Chem., 12(5), 1096 (1969); Marecki, Paul E.; Bambury, Ronald E., J. Pharm. Sci., 73(8), 1141 (1984); Pellerano, C.; Savini, L.; Massarelli, P.; Bruni, G.; Fiaschi, A. I., Farmaco, 45(3), 269, (1990); Marecki, Paul E.; Bambury, Ronald E., J. Pharm. Sci., 73(8), 114 (1984); patent application WO 8908105; U.S. Pat. No. 4,343,804; U.S. Pat. No. 3,470,186.

FLOWSHEET 1

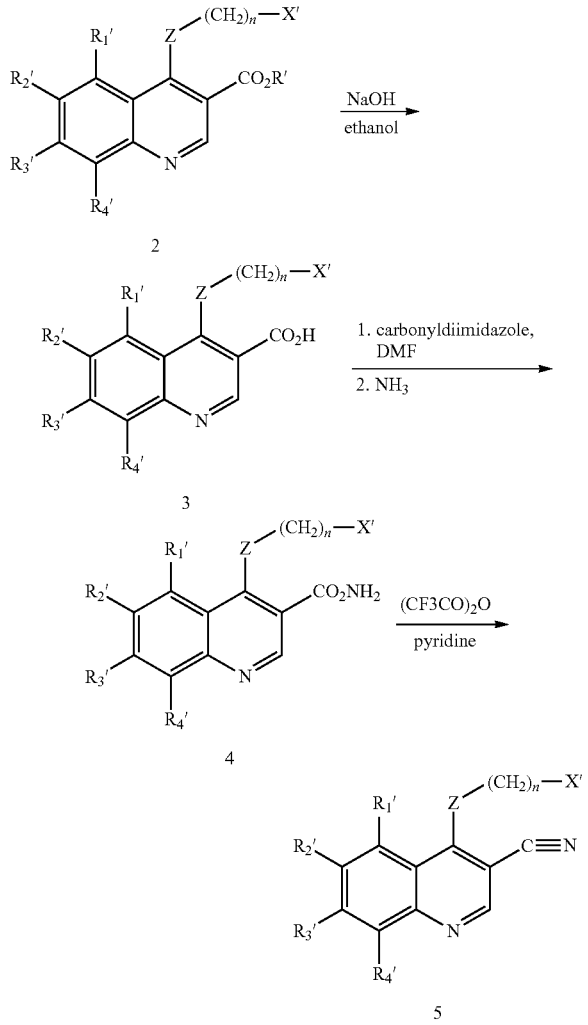

The preparation of the compounds of this invention encompassed by Formula 12 is described below in Flowsheet 2 where X, Z, n, $R_1$, $G_2$, $G_1$, and $R_4$ are as described above. The substituted aniline of Formula 6 is heated with or without a solvent with the reagent 7 to give intermediate 8 as a mixture of isomers. Thermolysis of 8 in a high boiling solvent such as diphenyl ether at 200-350° C. gives the 3-cyano quinolones of Formula 9; these intermediates may also exist in the 4-hydroxy quinoline tautomeric form. In those cases where $R_4$ is a hydrogen atom, the intermediates 9 may be formed as a mixture of two regioisomers. These isomers can be separated by methods well known in the art including, but not limited to, fractional crystallization and chromatographic methods. The separated isomers can then be converted separately to the compounds of the invention. Alternatively, the isomers can be separated at a later stage of the synthesis. Heating compounds 9 with or without solvent with a chlorinating agent such as phosphorous oxychloride or phosphorous pentachloride gives the 4-chloro-3-cyano quinolines of Formula 10. Condensation of 10 with a nucleophilic amine, aniline, mercaptan, thiophenol, phenol, or alcohol reagent of Formula 11 gives the 3-cyano quinolines intermediates of Formula 12; this condensation can be accelerated by heating the reaction mixture or by using basic catalysts such as trialkylamines, sodium hydride in an inert solvent, sodium or potassium alkoxides in an alcohol solvents, and the like. In those cases where the substituents may contribute an asymmetric carbon atom, the intermediates can be used as the racemate or as the individual R or S entantiomers in which case the compounds of this invention will be in the racemic or R and S optically active forms, respectively. In cases where the substituents may contribute more than one asymmetric carbon atoms, diasteriomers may be present; these can be separated by methods well known in the art including, but not limited to, fractional crystallization and chromatographic methods. In those cases where $R_1$, $G_2$, $G_1$, and $R_4$ moieties contain primary or secondary amino groups, the amino groups may first have to be used in protected form prior to reaction with reagent 7. Suitable protecting groups include, but are not limited to, tert-butoxycarbonyl (BOC) and benzyloxycarbonyl (CBZ) protecting groups. The former protecting group can be removed from the final products of Formula 12 by treatment with an acid such as trifluoroactic acid while the latter protecting group can be removed by catalytic hydrogenation. In those cases where the $R_1$, $G_2$, $G_1$, and $R_4$ moieties contain hydroxyl groups, the hydroxyl groups may first have to be used in protected form prior to reaction with reagent 7. Suitable protecting groups include, but are not limited to, t-butyldimethylsilyl, tetrahydropyranyl, or benzyl protecting groups. The first two protecting groups can be removed from the final products of formula 12 by treatment with an acid such as acetic acid or hydrochloric acid while the latter protecting group can be removed by catalytic hydrogenation.

FLOWSHEET 2

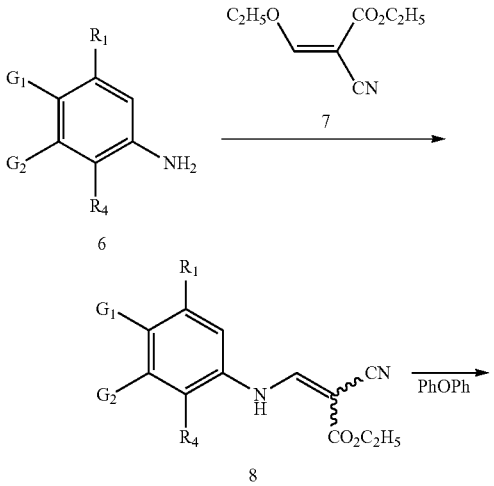

-continued

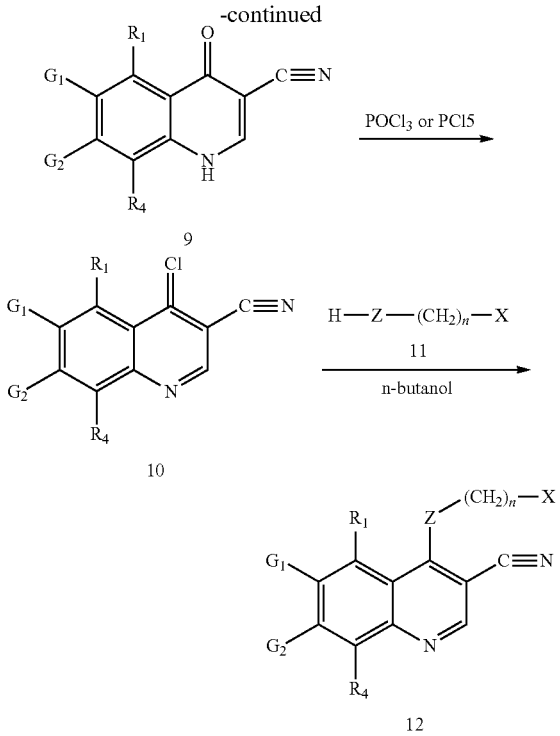

The preparation of intermediate 15 (identical to intermediate 9 of Flowsheet 2) can also be prepared as describe below in Flowsheet 3. Heating the substituted aniline of Formula 13 with dimethylformamide dimethyl acetal with or without a solvent gives intermediates for Formula 14. The reaction of 14 with the lithium anion of acetonitrile prepared using a base such as n-butyl lithium or the like in an inert solvent gives the 3-cyano quinolones, 15, or the 3-cyano-4-hydroxy quinoline tautomers thereof which can be converted to the compounds of this invention. In those cases where $R_1$, $G_2$, $G_1$, and $R_4$ moieties contain primary or secondary amino groups, the amino groups may first have to be used in protected form. Suitable protecting groups include, but are not limited to, tert-butoxycarbonyl (BOC) and benzyloxycarbonyl (CBZ) protecting groups. The former protecting group can be removed from the final products of Formula 15 by treatment with an acid such as trifluoroactic acid while the latter protecting group can be removed by catalytic hydrogenation. In those cases where the $R_1$, $G_2$, $G_1$, and $R_4$ moieties contain hydroxyl groups, the hydroxyl groups may first have to be used in protected form. Suitable protecting groups include, but are not limited to, t-butyldimethylsilyl, tetrahydropyranyl, or benzyl protecting groups. The first two protecting groups can be removed from the final products of formula 15 by treatment with an acid such as acetic acid or hydrochloric acid while the latter protecting group can be removed by catalytic hydrogenation.

FLOWSHEET 3

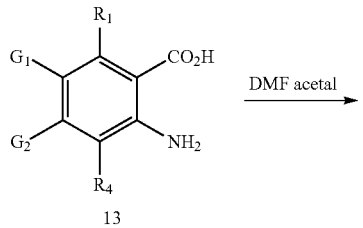

-continued

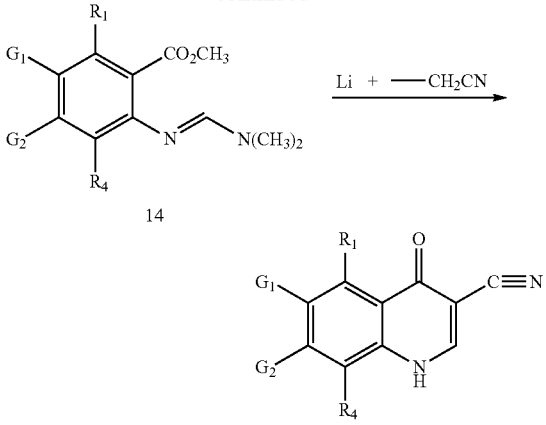

The preparation of the compounds of this invention encompassed by Formula 24 is described below in Flowsheet 4 wherein $R_1$, $G_2$, $R_4$, Z, n, and X are defined. $R_{10}$ is alkyl of 1-6 carbon atoms (preferably isobutyl). $R_2$' is a radical selected from the group consisting of:

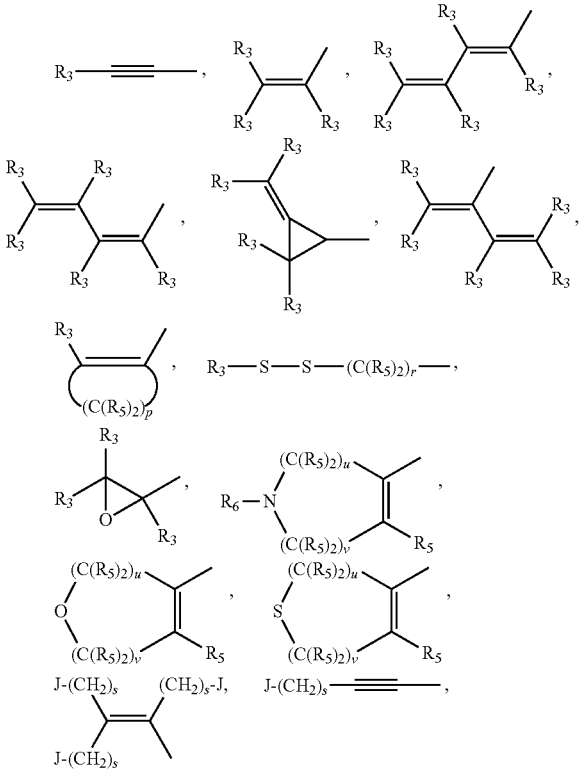

wherein $R_6$, $R_3$, $R_5$, J, s, r, u, and v are defined. According to the reactions outlined in Flowsheet 4, a 4-chloro-3-cyano-6-nitroquinoline, 16, can be reacted with an amine or aniline 17 by heating in an inert solvent such as tetrahydrofuran, butanol, or methoxyethanol to give compounds of Formula 20 where Z is —NH—. The reaction of 16 with a mercaptan or thiophenol 18 in an inert solvent can be accomplished using a base such as sodium hydride to give compounds of Formula 20 where Z is —S—. The reaction of 16 with a alcohol or phenol 19 in an inert solvent can be accomplished using a base such as sodium hydride to give compounds of Formula 20 where Z is —O—. Compounds of Formula 20 can be reduced to a 6-amino-3-cyano-quinoline, 21, using a reducing agent such as sodium hydrosulfite in a two phase system consisting of tetrahydrofuran and water in the presence of a small amount of phase transfer catalyst or by using iron in refluxing protic solvents containing acetic acid or ammonium chloride. Acylation of 21 with either an acid chloride of Formula 22 or a mixed anhydride of Formula 23 (which is prepared from the corresponding carboxylic acid) in an inert solvent such as tetrahydrofuran (THF) in the presence of an organic base such as pyridine, triethylamine, diisopropylethylamine, or N-methyl morpholine gives the compounds of this invention of Formula 24. In those cases where 22 or 23 have an asymmetric carbon atom, they can be used as the racemate or as the individual R or S entantiomers in which case the compounds of this invention will be in the racemic or R and S optically active forms, respectively. In those cases, where the $R_2$' contains primary or secondary amino groups, the amino groups will first have to be protected prior to anhydride or acid chloride formation. Suitable protecting groups include, but are not limited to, tert-butoxycarbonyl (BOC) and benzyloxycarbonyl (CBZ) protecting groups. The former protecting group can be removed from the final products of Formula 24 by treatment with an acid such as trifluoroactic acid while the latter protecting group can be removed by catalytic hydrogenation. In those cases where the $R_2$' contains hydroxyl groups, the hydroxyl groups may first have to be protected prior to anhydride or acid chloride formation. Suitable protecting groups include, but are not limited to, t-butyldimethylsilyl, tetrahydropyranyl, or benzyl protecting groups. The first two protecting groups can be removed from the final products of Formula 24 by treatment with an acid such as acetic acid or hydrochloric acid while the latter protecting group can be removed by catalytic hydrogenation. In those cases, in intermediates 17, 18, or 19 where X contains primary or secondary amino groups or hydroxyl groups, it may be necessary to protect these groups prior to the reaction with 16. The same amine or alcohol protecting groups describe above can be used and they can be removed from the products 24 as previously described.

FLOWSHEET 4

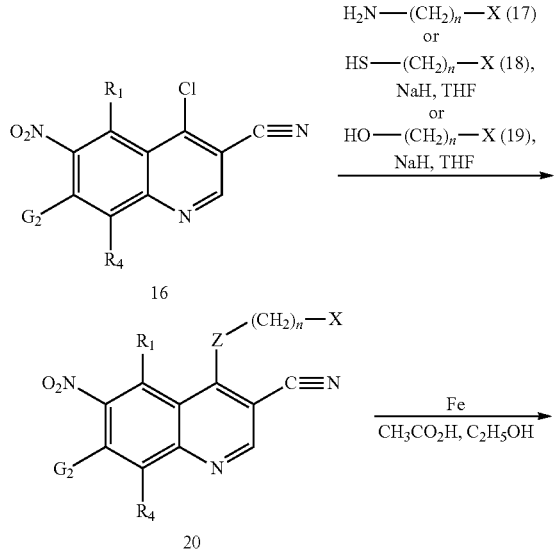

-continued

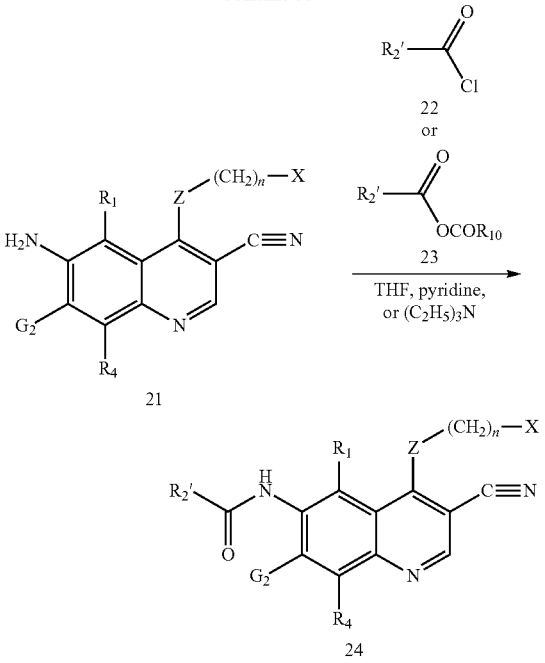

By using methods similar to that describe above in Flowsheet 4, the intermediates 25 can be converted to the compounds of this invention, 26.

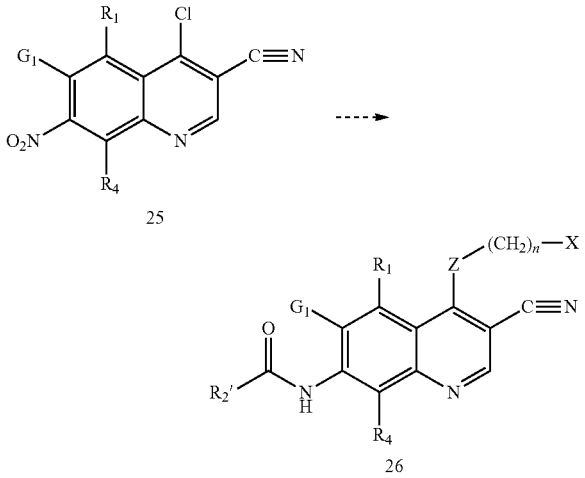

In order to prepare the compounds of this invention, certain amines are required. Some representative amines are shown below in List A wherein $R_6$, p, and r are as defined above. These amines are available commercially, are known in the chemical literature, or can be prepared by simple procedures that are well known in the art. In some cases, these amines may have an asymmetric carbon atoms; they can be used as the racemate or they can be resolved and used as the individual R or S entantiomers in which case the compounds of this invention will be in the racemic or optically active forms, respectively. Throughout this application in the Flowsheets shown below, these amines, and other similar amines, will be represented by the generic structure of the formula:

$(R')_2NH$, wherein this formula can represent a primary or secondary amine.

List A

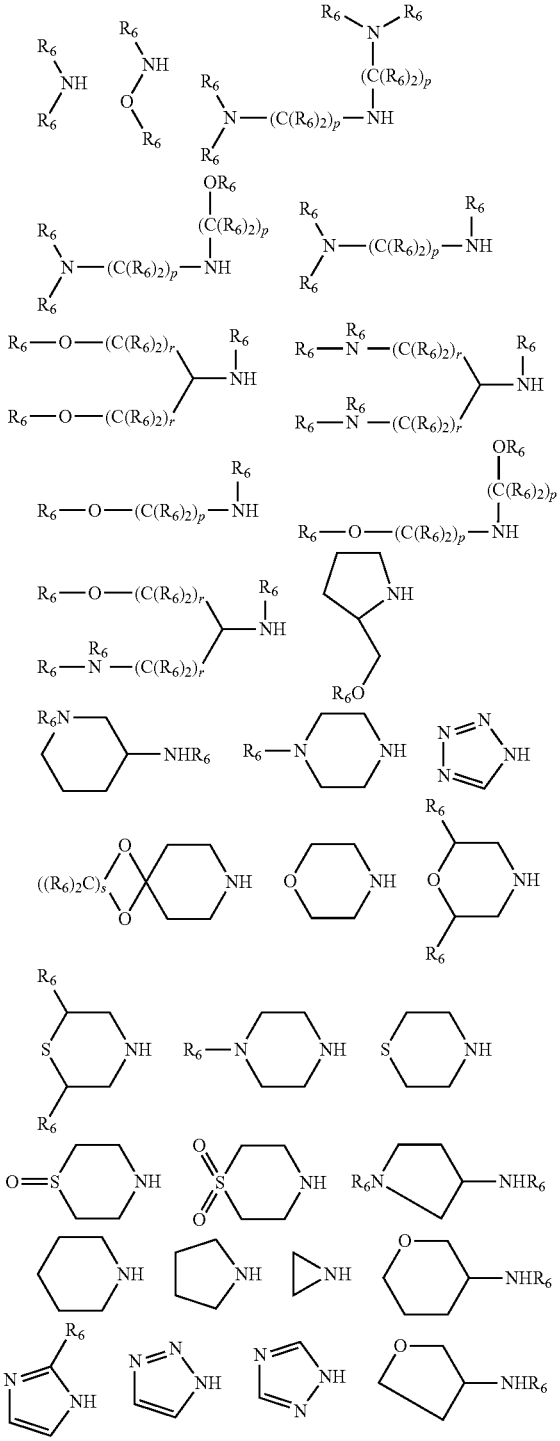

In order to prepare the compounds of this invention certain alcohols are required. Some representative alcohols are shown below in List B wherein $R_6$, p, and r are as defined above. These alcohols are available commercially, are known in the chemical literature, or can be prepared by simple procedures that are well known in the art. In some cases, these alcohols may have an asymmetric carbon atoms; they can be used as the racemate or they can be resolved and used as the individual R or S entantiomers in which case the compounds of this invention will be in the racemic or optically active forms, respectively. Throughout this application in the Flowsheets shown below, these alcohols, and other similar alcohols, will be represented by the generic structure of the formula:

List B

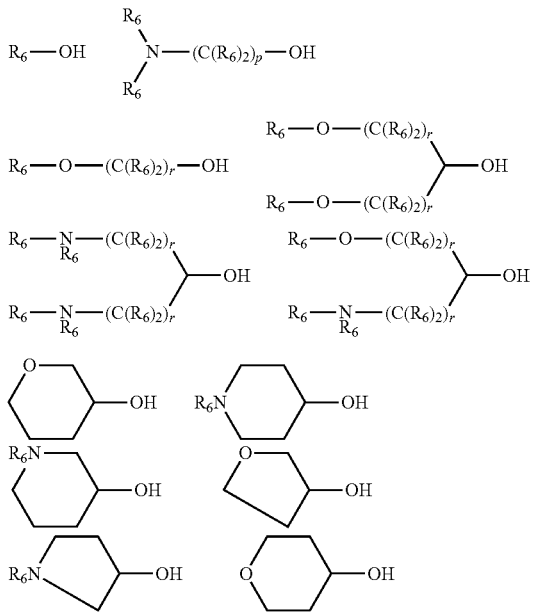

In order to prepare some of the compounds of this invention certain mixed anhydrides of Formulas 31, 34, and 38 are required; these are prepared as outlined below in Flowsheet 5-6 wherein $R_6$, $R_{10}$, X, Z, n, and s are as defined above. J' is a halogen atom chlorine, bromine, or iodine, or is a toslyate (p-toluenesulfonate) or mesylate (methanesulfonate) group. The reaction of 27 with an amine of List A is accomplished by heating in an inert solvent such as tetrahydrofuran or N,N-dimethylformamide, or using potassium or cesium carbonate in acetone. The temperature and duration of the heating will depend on the reactivity of 27; longer reaction times and higher temperatures may be required when s is greater than 1. Treatment of 28 with an alkyl lithium reagent followed by quenching with an atmosphere of dry carbon dioxide furnishes the carboxylic acids of Formula 29. These can be converted to mixed anhydrides of Formula 31 using a reagent such as isobutylchloroformate in an inert solvent such as tetrahydrofuran in the presence of a base such as N-methylmorpholine. These anhydrides can then be used to prepare the compounds of this invention as described above in Flowsheet 4. The reaction of 27 with an alcohol of List B is accomplished using sodium hydride or other non-nucleophic base such as potassium or cesium carbonate in an inert solvent such as tetrahydrofuran, acetone, or N,N-dimethylformamide. In some cases, the alcohol of List B can also be the solvent of the reaction. Treatment of 32 with an alkyl lithium reagent followed by quenching with an atmosphere of dry carbon dioxide furnishes the carboxylic acids of Formula 33. These can be converted to mixed anhydrides Formula 34 using a reagent such as isobutylchloroformate in an inert solvent such as tetrahydrofuran in the presence of a base such as N-methylmorpholine. These anhydrides can then be used to prepare the compounds of this invention as described above in Flowsheet 4.

FLOWSHEET 5

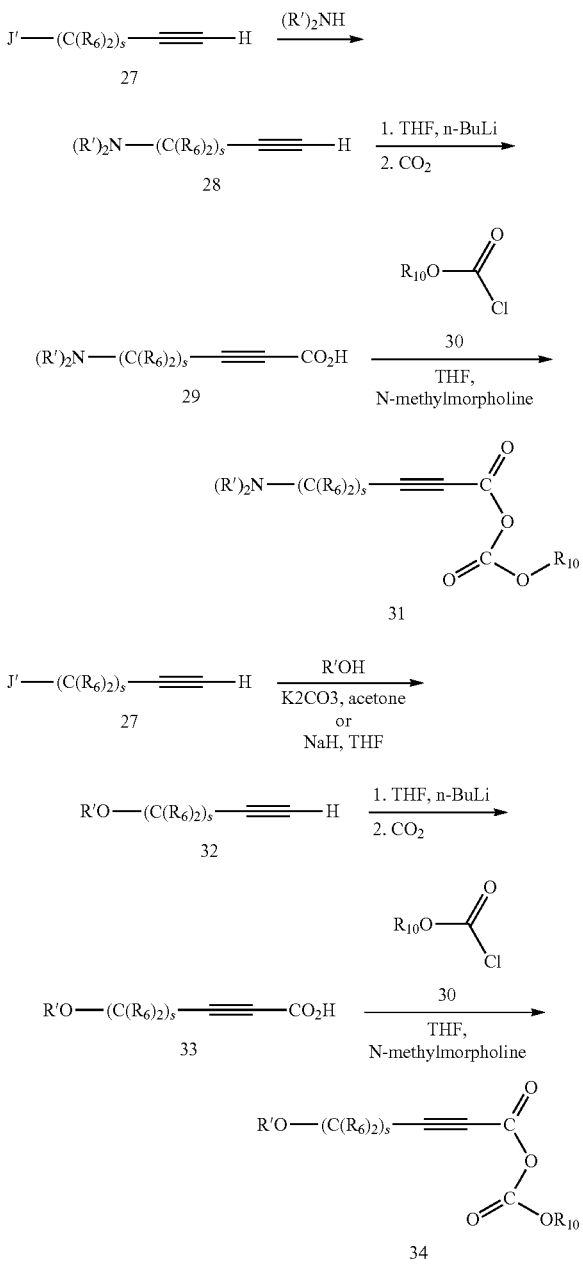

As outline in Flowsheet 6 below wherein $R_1$, $G_2$, $R_4$, $R_6$, $R_{10}$, X, Z, n, and s are as defined above, alcohols 35 can be protected with a t-butyl dimethysilyl protecting group by the reaction with the respective silyl chloride in methylene chloride in the presence of triethylamine and 4-N,N-dimethylamino pyridine (DMAP). The resulting protected alcohols, 36, are converted to the acetylenic Grignard reagents which, in turn, are maintained under an atmosphere of dry carbon dioxide to give the carboxylic acids 37. As described above these are converted to the mixed anhydrides 38 which on reaction with the 6-amino3-cyanoquinoline 39 gives 40. In the final step of the sequence, the silyl protecting group is removed by treating with acid in a protic solvent mixture to give the compounds represented by Formula 41.

FLOWSHEET 6

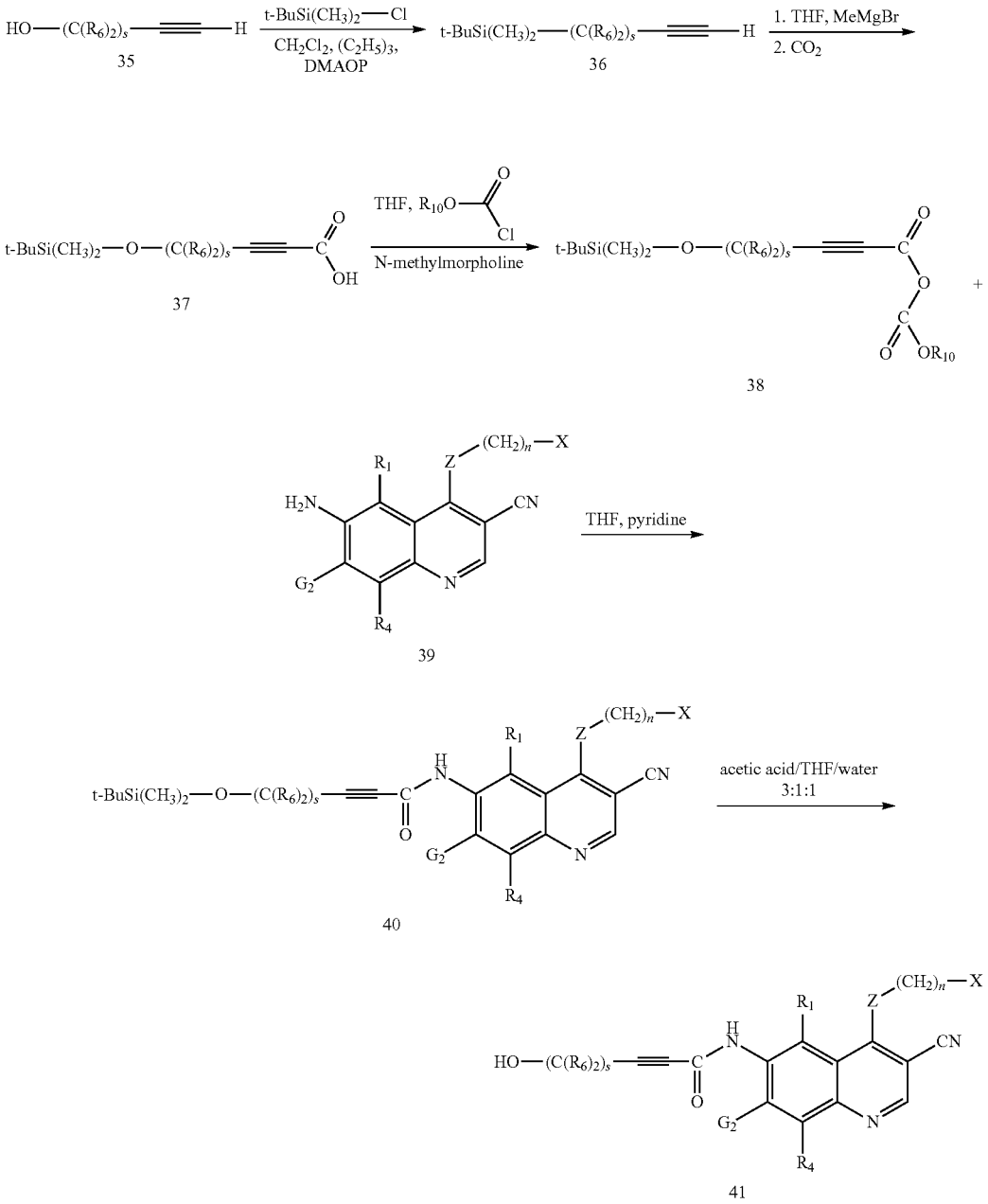

Compounds of this invention are also prepared as shown below in Flowsheet 7 wherein $R_1$, $G_2$, $R_4$, $R_6$, $R_{10}$, X, Z, n, and s are as defined above. J' is a halogen atom chlorine, bromine, or iodine, or is a toslyate or mesylate group. Treatment of 42 with an alkyl lithium reagent at low temperature followed by quenching with an atmosphere of dry carbon dioxide furnishes the carboxylic acids of formula 43. These can be converted to mixed anhydrides of Formula 44 using a reagent such as isobutylchloroformate in an inert solvent such as tetrahydrofuran in the presence of a base such as N-methylmorpholine. These anhydrides can then be used to prepare the compounds of this invention as by the reaction with the 6-amino-3-cyanoquinolines 45 described above in the Flowsheets. The reaction of 46 with an alcohol of List B is accomplished using sodium hydride or other non-nucleophic base in an inert solvent such as tetrahydrofuran or N,N-dimethylformamide to give the compounds of this invention represented by 47. In some cases, the alcohol of List B can also be the solvent of the reaction. The reaction of 46 with an amine of List A gives the compounds of this invention represented by 48 is accomplished by heating in an inert solvent such as tetrahydrofuran or N,N-dimethylformamide, or using potassium or cesium carbonate in acetone. The temperature and duration of the heating will depend on the reactivity of 46; longer reaction times and higher temperatures may be required when s is greater than 1.

FLOWSHEET 7
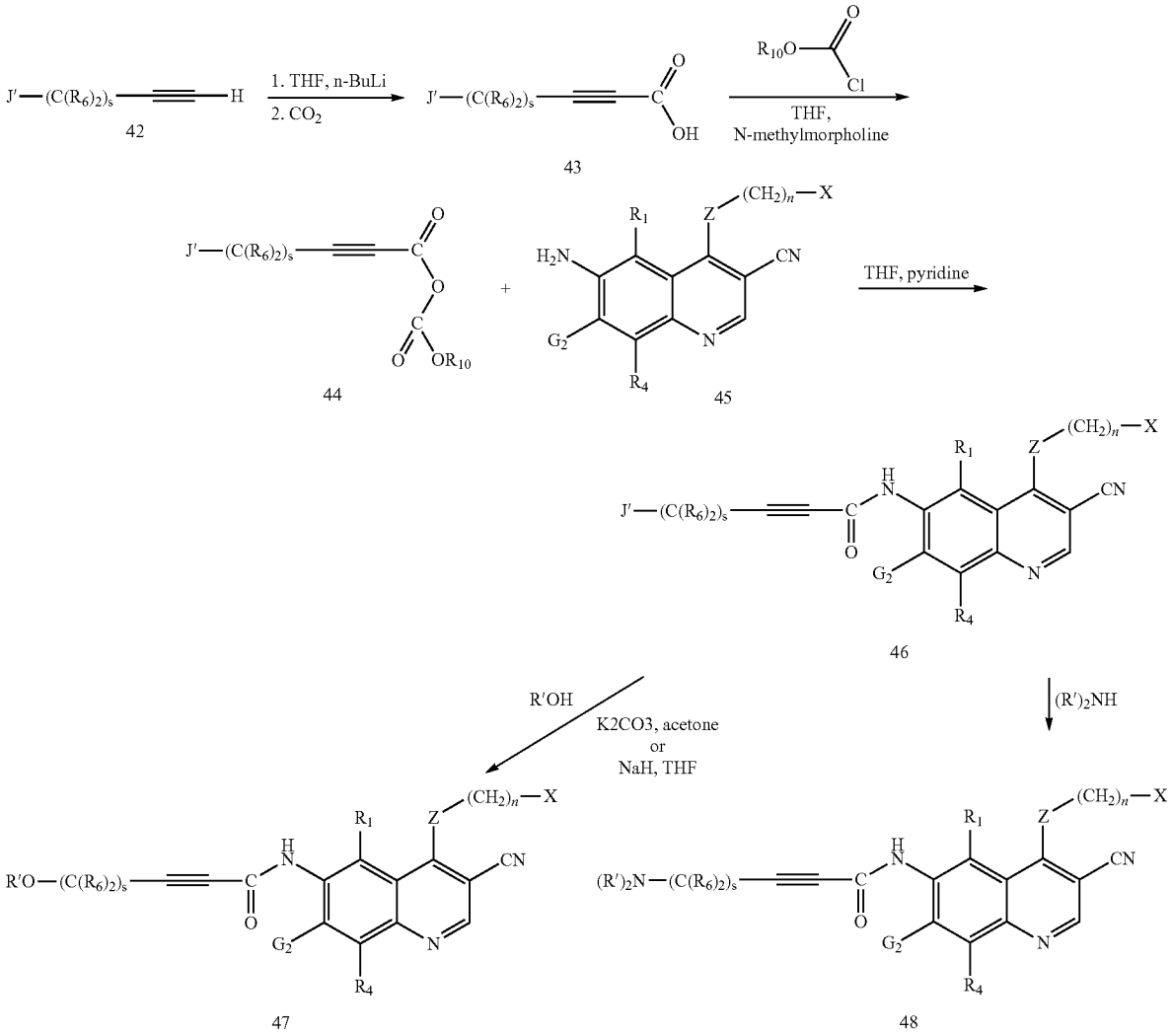
Using methods similar to that summarized above, 45b can be converted to 47b or 48b.
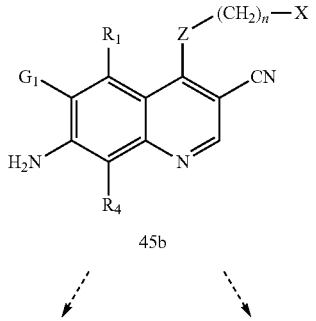

-continued

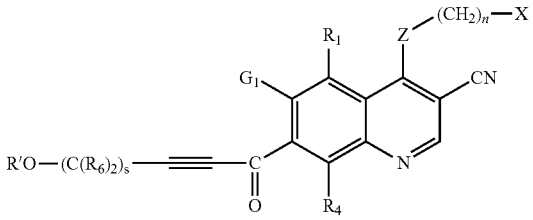

47b

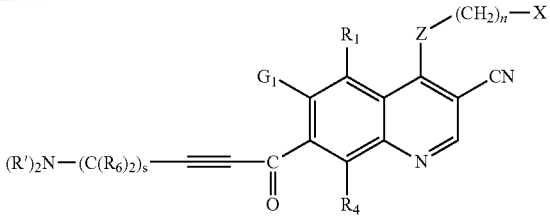

48b

Other carboxylic acid chlorides and anhydrides needed to prepare some of the compounds of this invention are prepared as shown below in Flowsheet 8 wherein $R_6$, $R_3$, $R_{10}$, X, Z, J', n, and s are as defined above. Q' is an alkyl group of 1-6 carbon atoms. The esters 49, 53, or 57 can be hydrolyzed with a base such as barium hydroxide to give the respective carboxylic acid 50, 54, or 58. These acid can be converted to the respective carboxylic acid chlorides 51 or 56 by using oxalyl chloride and catalytic N,N-dimethylforrnamide in an inert solvent or respective mixed anhydrides 55 or 59 by using isobutyl chloroformate and an organic base such as N-methylmorpholine. The leaving group in compounds represented by Formula 52 can be displaced by the amines of List A or the alcohols of List B by using procedures previously described to give the intermediates 57 and 53, respectively. These carboxylic acid chlorides 51 and 56 and these anhydrides 55 and 59 can be used to prepare some of the compounds of this invention by using the methods outlined herein above in the Flowsheets.

FLOWSHEET 8

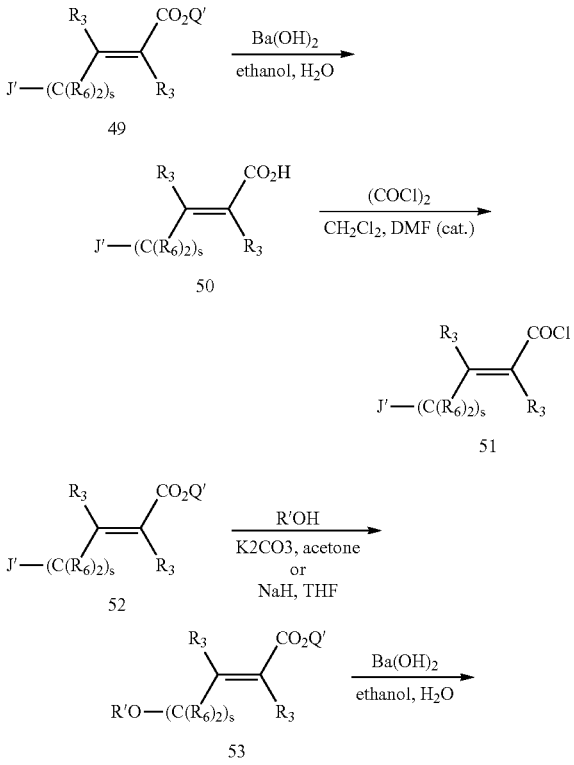

-continued

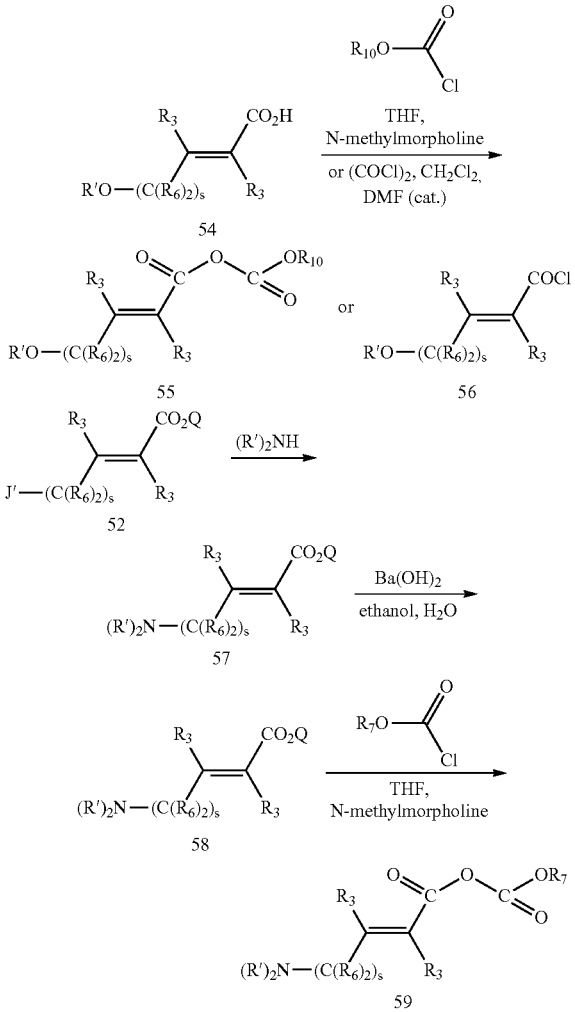

By using the methods identical to those outlined above in Flowsheet 8, it is possible to prepare the analogous carboxylic acid chlorides and anhydrides given below in List C wherein $R_6$, $R_3$, p, and s are as previously defined. G is the radical:

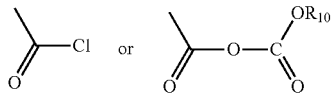

and A is the radical:

—N(R')$_2$, —OR', or –J' wherein —N(R')$_2$ is derived from the amines of List A, —OR' are derived from the alcohols of List B, and J' is a leaving group as defined previously. By making use of these carboxylic acid chlorides and anhydrides, by following the methods summarized in the above in Flowsheets, and by pursuing the details described in the examples given below, many of the compounds of this invention can be prepared.

List C

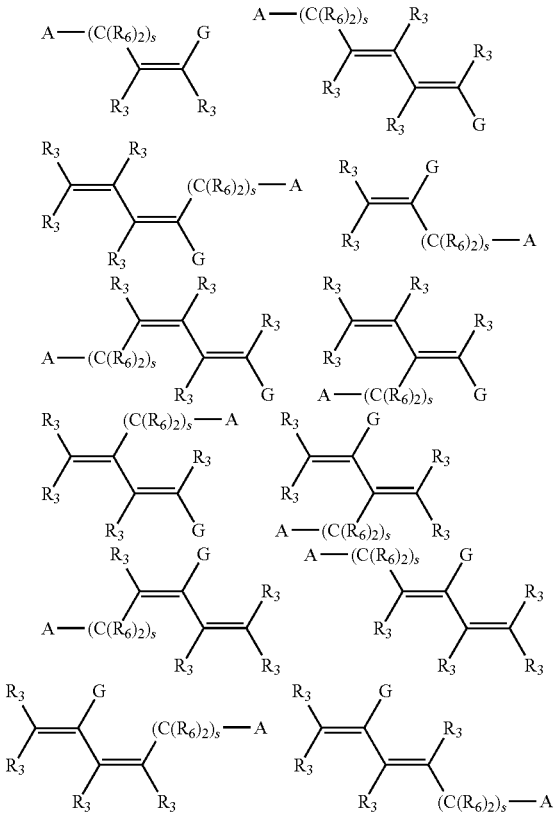

-continued

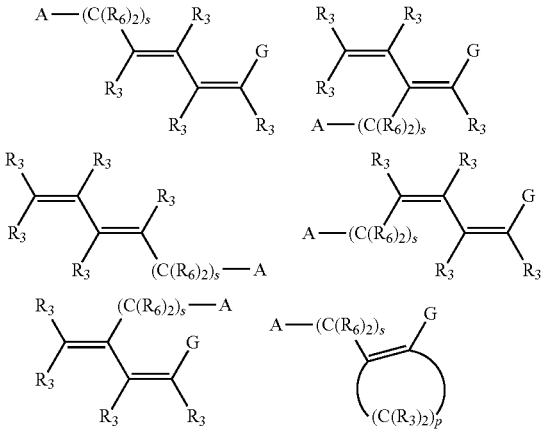

Compounds of this invention represented by Formulas 62-63 can be prepared as shown in Flowsheet 9 wherein $R_1$, $G_2$, $R_4$, $R_6$, $R_3$, $R_{10}$, X, Z, J', n, and s are as defined above. The reaction of the carboxylic acid chlorides 60 and the 6-amino-3-cyanoquinolines 61 using an organic base in an inert solvent gives the compounds of this invention represented by Formula 62. The reaction of 62 with an alcohol of List B is accomplished using sodium hydride or other non-nucleophic base such as potassium or cesium carbonate in an inert solvent such as tetrahydrofuran, acetone, or N,N-dimethylformamide to give the compounds of this invention represented by 63. In some cases, the alcohol of List B can also be the solvent of the reaction. The reaction of 62 with an amine of List A to give the compounds of this invention represented by 64 is accomplished by heating in an inert solvent such as tetrahydrofuran or N,N-dimethylformamide. The temperature and duration of the heating will depend on the reactivity of 62; longer reaction times and higher temperatures may be required when s is greater than 1. In addition, by using this method, the carboxylic acid chlorides and mixed anhydrides listed in List C can be used to prepare the analogous compounds of this invention.

FLOWSHEET 9

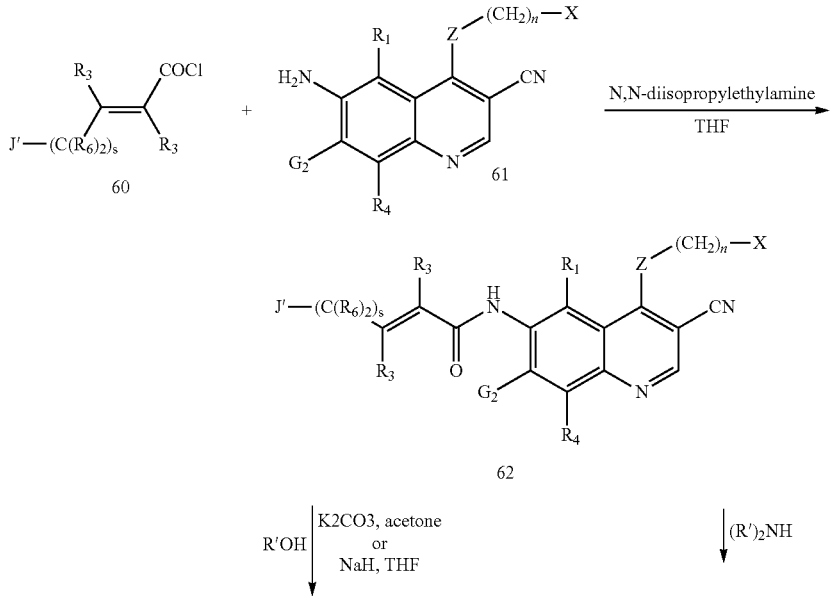

-continued

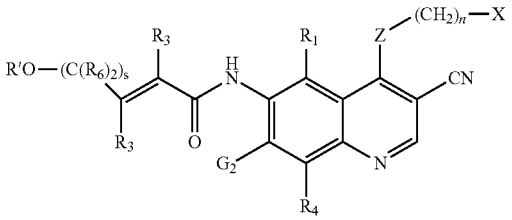

63

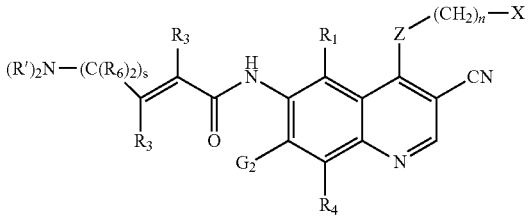

64

By applying the methods summarized above, 61b can be converted to 63b and 64b via the intermediate 62b.

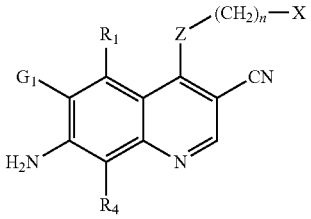

61b

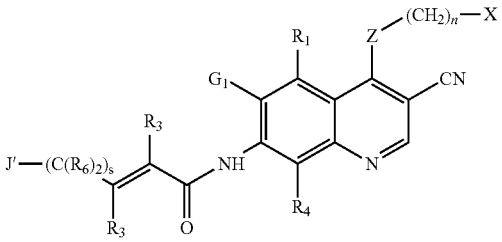

62b

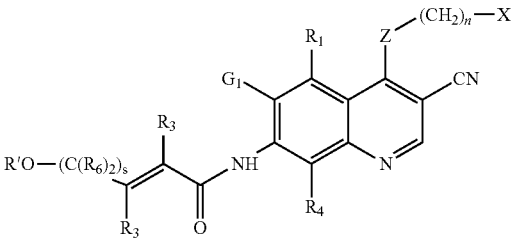

63b

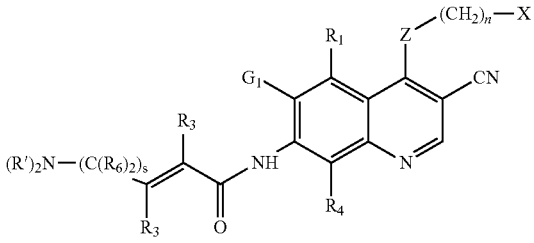

64b

The reaction of 62 or 62b with a nitrogen containing heterocycle HET which also contains an unsaturated carbon-nitrogen bond is accomplished by refluxing in an inert solvent and gives the compounds of this invention 64c and 64d, respectively where the compound bears a positive charge. The counter anion J'—can be replaced with any other pharmaceutically acceptable anion using the appropriate ion exchange resin.

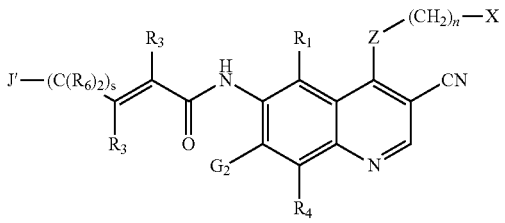

62

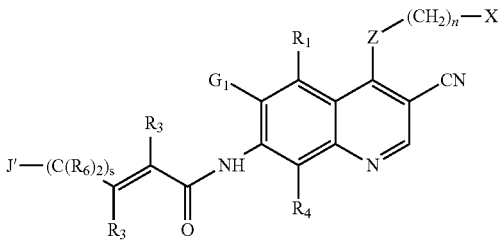

62b

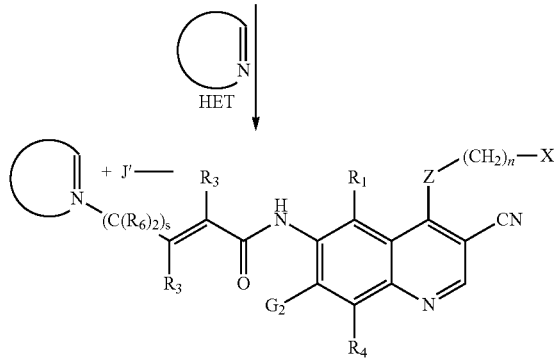

64c

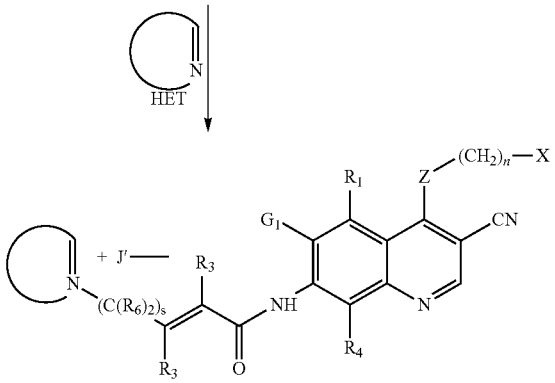

64d

Some of the compounds of this invention can be prepared as outline below in Flowsheet 10 wherein $R_1$, $G_2$, $R_3$, $R_4$, $R_6$, $R_{10}$, X, Z, J', n, and r are as defined above. The acetylenic alcohols 65 can be coupled to the halides, mesylates, or tosylates 66 using a base such as sodium hydride in an inert solvent such as tetrahydrofuran. The resulting acetylene, 67, is then treated with an alkyl lithium reagent at low temperature. Maintaining the reaction under an atmosphere of carbon dioxide then gives the carboxylic acids 68. These, in turn, are reacted with the 6-amino-3-cyanoquinolines, 69, via the mixed anhydrides to give the compounds of this invention represented by Formula 70. Alternatively, the intermediates 67 can be prepared starting with an alcohol 71 by first treating it with a base such as sodium hydride in an inert solvent such as tetrahydrofuran and then adding an acetylene 72 that has an appropriate leaving group. In a similar manner, the amino alcohols represented by the formula: $(R_6)_2N—(C(R_6)_2)_r—OH$ by reacting with 72, and applying the chemistry of Flowsheet 10, can be converted to the compounds of this invention represented by the formulas:

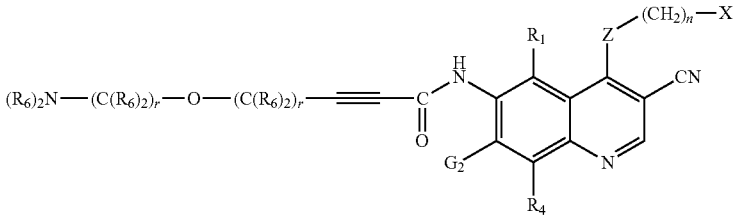

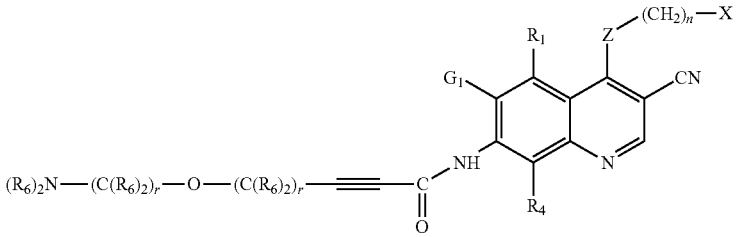

FLOWSHEET 10

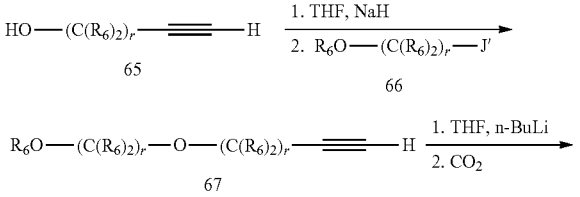

-continued

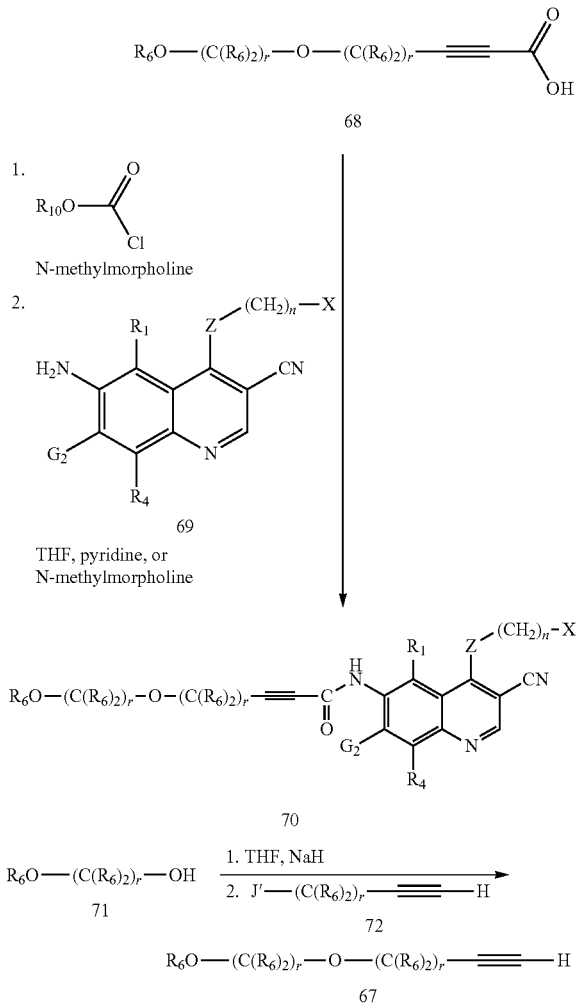

By applying similar methods as described above, 69b can be converted to the compounds of this invention represented by 70b.

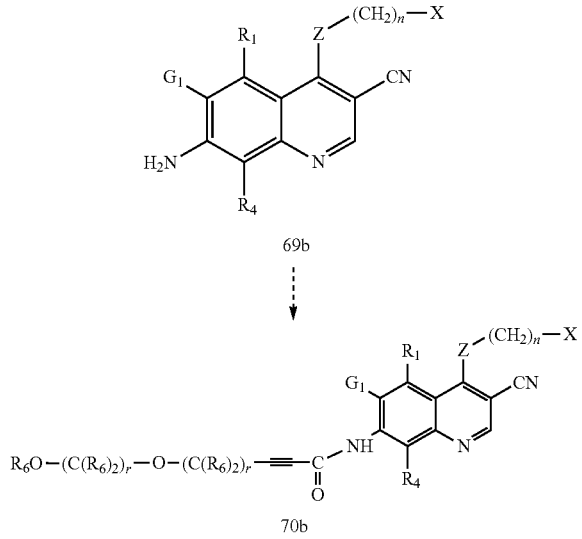

The compounds of this invention represented by Formula 76 and 77 are prepared as shown below in Flowsheet 11 wherein $R_1$, $R_3$, $R_4$, $R_6$, and n defined above and the amines $HN(R'')_2$ are selected from the group:

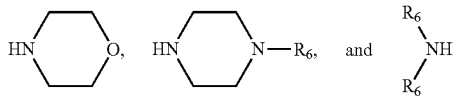

Refluxing 73 and 74 in an a solvent such as ethanol gives the intermediate 75 which can react with an amine in refluxing ethanol to give the compounds of this invention represented by Formula 76. Treating 75 with an excess of a sodium alkoxide in an inert solvent or a solvent from which the alkoxide is derived gives the compounds of this invention of Formula 77.

FLOWSHEET 11

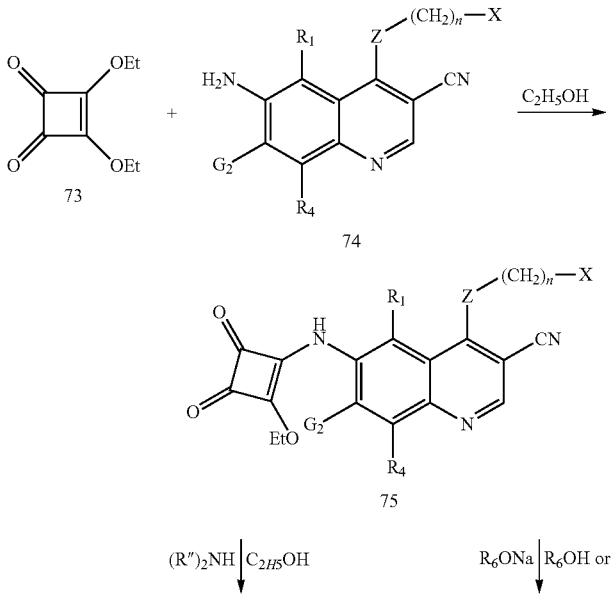

-continued

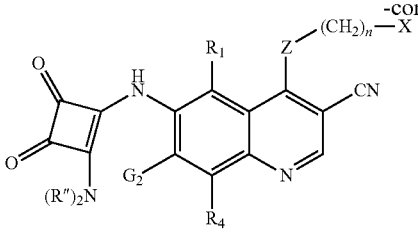

76

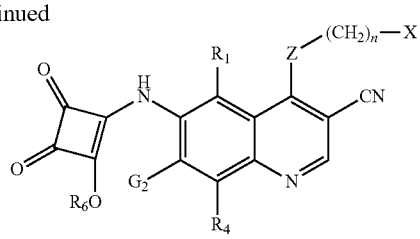

77

In a manner similar to that described above, 74b can be converted to 76b or 77b.

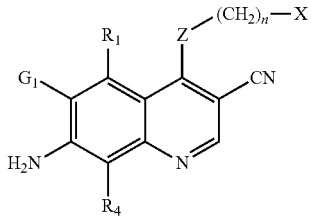

74b

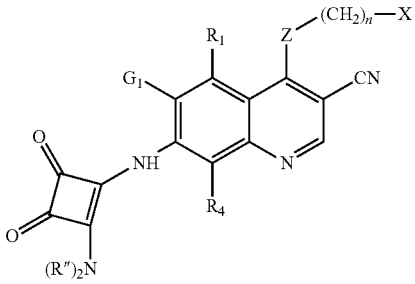

76b

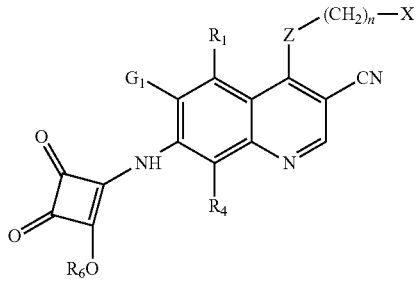

77b

Compounds of this invention represented by Formula 83 can be prepared as shown in Flowsheet 12 wherein $R_1$, $G_2$, $R_4$, $R_6$, $R_3$, $R_{10}$, X, Z, n, and r are as defined above. The reaction of the mecapto carboxylic acids 78 with the reagents 79 give the compounds represented by Formula 80. Alternatively, 80 can be prepared from the mercaptan $R_3SH$ using the mercapto acid 78, triethylamine and 2,2'-dipyridyl disulfide. Mixed anhydride formation to give 81 followed by condensation with the 6-amino-3-cyanoquinolines 82 give the compounds of this invention.

FLOWSHEET 12

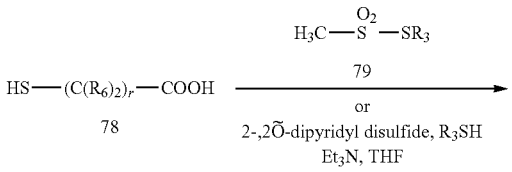

-continued

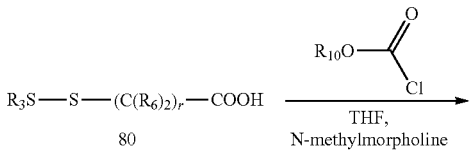

80

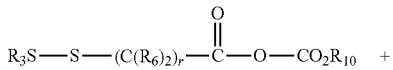

81

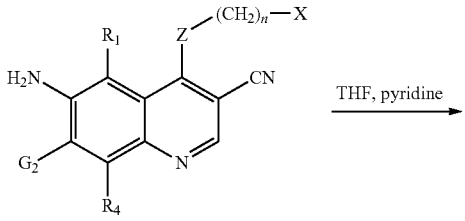

82

-continued

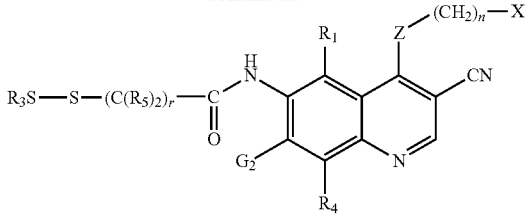

83

By applying similar methods as described above 821 can be converted to 83.

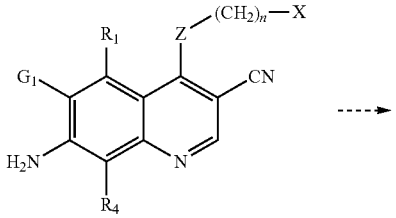

82b

-continued

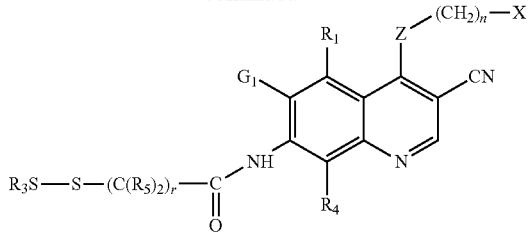

83b

Compounds of this invention represented by Formulas 86-88 can be prepared as shown in Flowsheet 13 wherein $R_1$, $G_2$, $R_1$, $R_4$, $R_5$, J', X, Z, and n are as defined above. Q' is alkyl of 1-6 hydrogen atoms, alkoxy of 1-6 hydrogen catoms, hydroxy, or hydrogen. Akylation of 84 with the 6-amino-3-cyanoquinolines 85 can be accomplished by heating in an inert solvent such as N,N-dimethylformamide using a base such as potassium carbonate to give the compounds of this invention represented by the Formula 86. When Q' is alkoxy, the ester group can be hydrolyzed to an acid using a base such as sodium hydroxide in methanol. In a similar manner, by using intermediates 89 and 90, the compounds of this invention represented by Formulas 87 and 88 can be prepared, respectively.

FLOWSHEET 13

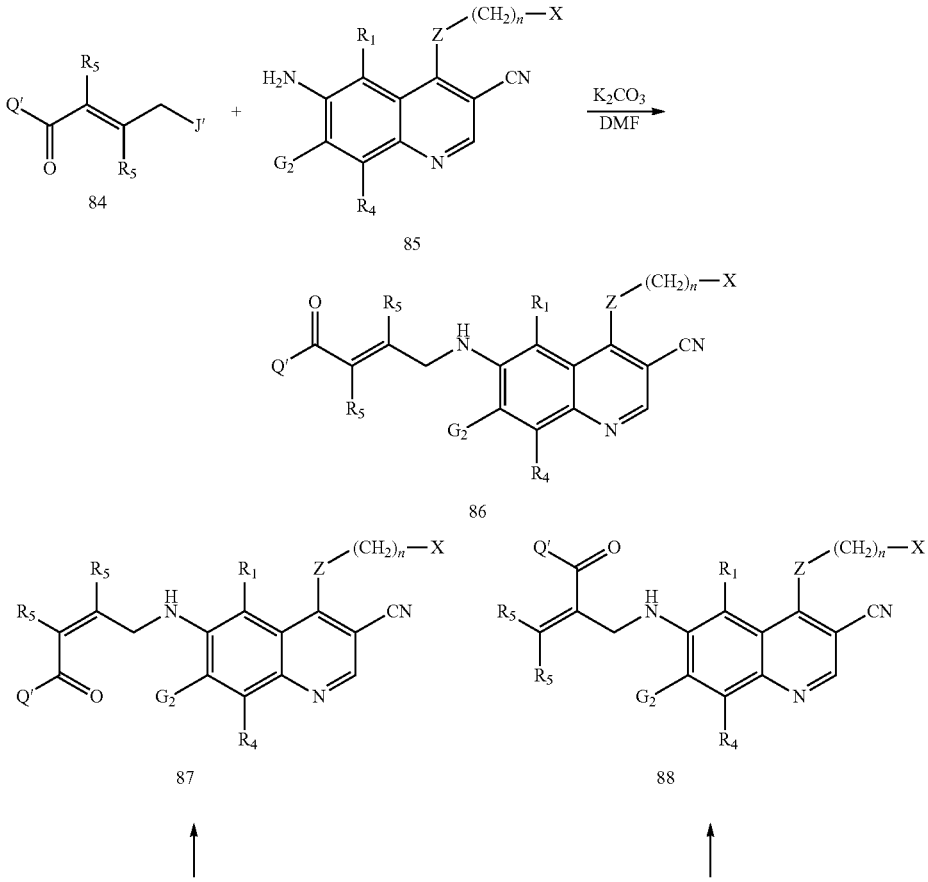

-continued

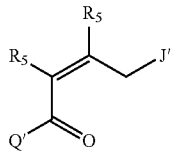

89

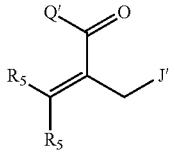

90

By apply similar methods as described above 85b can be converted to 86b-88b.

85b

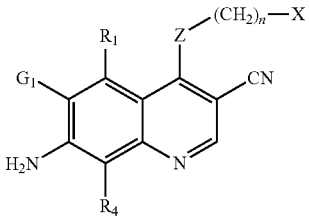

86b

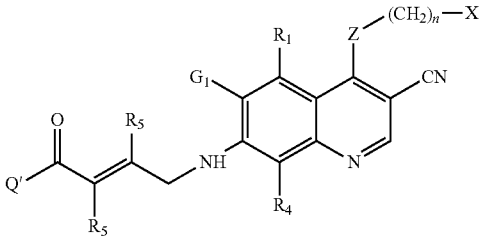

87b

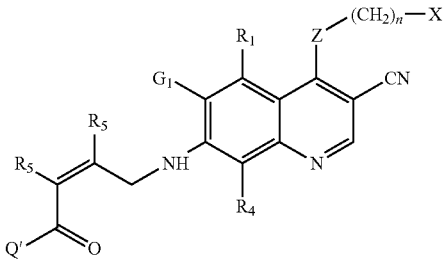

88b

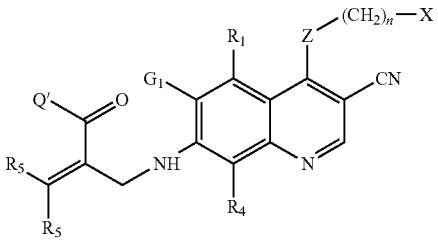

Compounds of this invention represented by Formula 93 can be prepared as shown in Flowsheet 14 wherein $R_1$, $G_2$, $R_1$, $R_4$, $R_5$, X, Z, and n are as defined above. The reaction of reagent 91 with the 6-amino-3-cyanoquinolines 92 is accomplished using an excess of an organic base such as triethylamine and an inert solvent such as tetrahydrofuran to give compounds of this invention represented by Formula 93.

FLOWSHEET 14

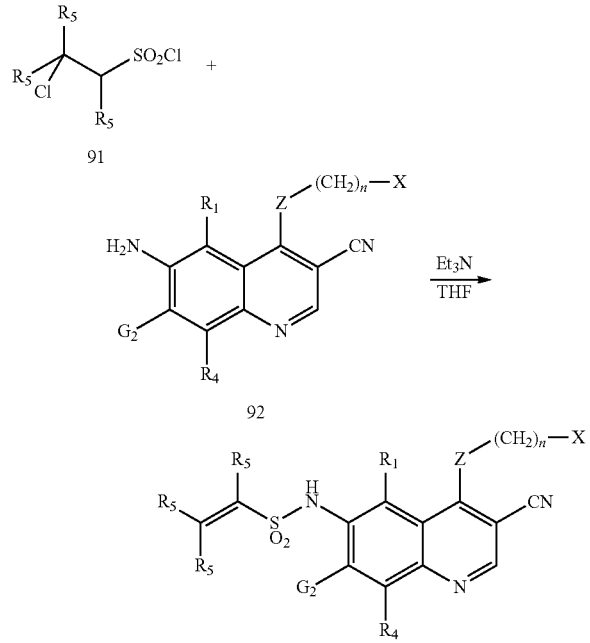

91

92

93

Compounds of this invention represented by Formula 96 can be prepared as shown in Flowsheet 15 wherein $R_1$, $G_1$, $R_1$, $R_4$, $R_5$, $R_6$, W, Het, X, Z, k, and n are as defined above by the Mitsunobu reaction of phenol 94 and an alcohol 95 in an inert solvent. Alternatively, the Mitsunobu reaction can be applied to compound 97 to give 98. This compound can be converted to 96 as described above in Flowsheet 4. The heterocycle can be introduced at the 6-position by using the corresponding compounds where $G_1$ is hydroxy and $G_2$ is located at the 7-position.

FLOWSHEET 15

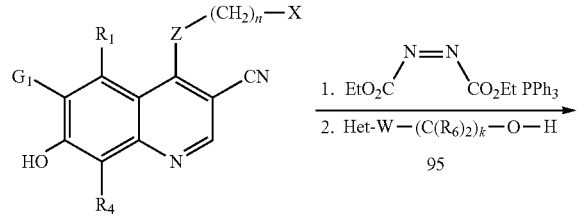

94

95

-continued

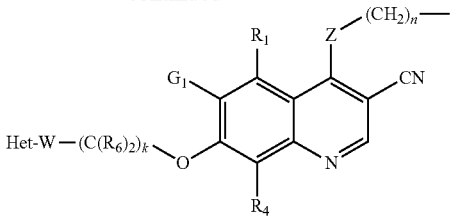

96

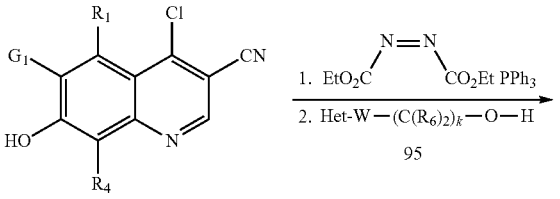

97

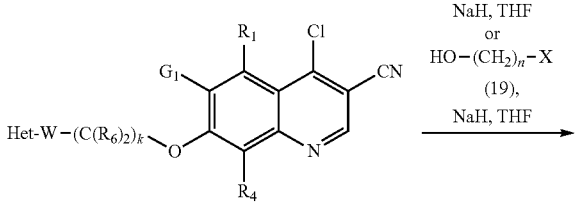

98

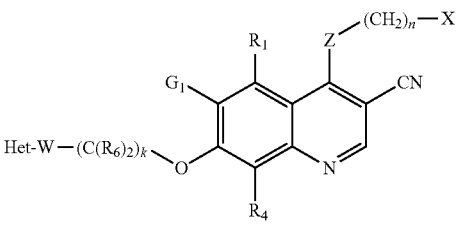

96

There are certain functional group manipulations that are useful to prepare the compounds of this invention that can be applied to various intermediate 3-cyanoquinolines as well as to the final compounds of this invention. These manipulations refer to the substituents $R_1$, $G_1$, $G_2$, or $R_4$ that are located on the 3-cyanoquinolines shown in the above Flowsheets. Some of these functional group manipulations are described below:

Where one or more of $R_1$, $G_1$, $G_2$, or $R_4$ is a nitro group, it can be converted to the corresponding amino group by reduction using a reducing agent such as iron in acetic acid or by catalytic hydrogenation. Where one or more of $R_1$, $G_1$, $G_2$, or $R_4$ is an amino group, it can be converted to the corresponding dialkyamino group of 2 to 12 carbon atoms by alkylation with at least two equivalents of an alkyl halide of 1 to 6 carbon atoms by heating in an inert solvent or by reductive alkylation using an aldehyde of 1 to 6 carbon atoms and a reducing agent such as sodium cyanoborohydride. Where one or more of $R_1$, $G_1$, $G_2$, or $R_4$ is a methoxy group, it can be converted to the corresponding hydroxy group by reaction with a demethylating agent such as boron tribromide in an inert solvent or by heating with pyridinium chloride with or without solvent. Where one or more of $R_1$, $G_1$, $G_2$, or $R_4$ is an amino group, it can be converted to the corresponding alkylsulfonamido, alkenylsulfonamido, or alkynylsulfonamido group of 2 to 6 carbon atoms by the reaction with an alkylsulfonyl chloride, alkenylsulfonyl chloride, or alkynylsulfonyl chloride, respectively, in an inert solvent using a basic catalyst such as triethylamine or pyridine. Where one or more of $R_1$, $G_1$, $G_2$, or $R_4$ is an amino group, it can be converted to the corresponding alkyamino group of 1 to 6 carbon atoms by alkylation with one equivalent of an alkyl halide of 1 to 6 carbon atoms by heating in an inert solvent or by reductive alkylation using an aldehyde of 1 to 6 carbon atoms and a reducing agent such as sodium cyanoborohydride in a protic solvent such as water or alcohol, or mixtures thereof. Where one or more of $R_1$, $G_1$, $G_2$, or $R_4$ is hydroxy, it can be converted to the corresponding alkanoyloxy, group of 1-6 carbon atoms by reaction with an appropriate carboxylic acid chloride, anhydride, or mixed anhydride in a inert solvent using pyridine or a trialkylamine as a catalyst. Where one or more of $R_1$, $G_1$, $G_2$, or $R_4$ is hydroxy, it can be converted to the corresponding alkenoyloxy group of 1-6 carbon atoms by reaction with an appropriate carboxylic acid chloride, anhydride, or mixed anhydride in an inert solvent using pyridine or a trialkylamine as a catalyst. Where one or more of $R_1$, $G_1$, $G_2$, or $R_4$ is hydroxy, it can be converted to the corresponding alkynoyloxy group of 1-6 carbon atoms by reaction with an appropriate carboxylic acid chloride, anhydride, or mixed anhydride in a inert solvent using pyridine or a trialkylamine as a catalyst. Where one or more of $R_1$, $G_1$, $G_2$, or $R_4$ is carboxy or a carboalkoxy group of 2-7 carbon atoms, it can be converted to the corresponding hydroxymethyl group by reduction with an appropriate reducing agent such as borane, lithium borohydride, or lithium aluminum hydride in a inert solvent; the hydroxymethyl group, in turn, can be converted to the corresponding halomethyl group by reaction in an inert solvent with a halogenating reagent such as phosphorous tribromide to give a bromomethyl group, or phosphorous pentachloride to give a chloromethyl group. The hydroxymethyl group can be acylated with an appropriate acid chloride, anhydride, or mixed anhydride in an inert solvent using pyridine or a trialkylamine as a catalyst to give the compounds of this invention with the corresponding alkanoyloxymethyl group of 2-7 carbon atoms, alkenoyloxymethyl group of 2-7 carbon atoms, or alkynoyloxymethyl group of 2-7 carbon atoms. Where one or more of $R_1$, $G_1$, $G_2$, or $R_4$ is a halomethyl group, it can be converted to an alkoxymethyl group of 2-7 carbon atoms by displacing the halogen atom with a sodium alkoxide in an inert solvent. Where one or more of $R_1$, $G_1$, $G_2$, or $R_4$ is a halomethyl group, it can be converted to an aminomethyl group, N-alkylaminomethyl group of 2-7 carbon atoms or N,N-dialkylaminomethyl group of 3-14 carbon atoms by displacing the halogen atom with ammonia, a primary, or secondary amine, respectively, in an inert solvent.

In addition to the methods described herein above, there a number of patent applications that describe methods that are useful for the preparation of the compounds of this invention. Although these methods describe the preparation of certain quinazolines, they are also applicable to the preparation of correspondingly substituted 3-cyanoquinolines. The chemical procedures described in the application WO-9633981 can be used to prepare the 3-cyanoquinoline intermediates used in this invention wherein $R_1$, $G_1$, $G_2$, or $R_4$ are alkoxyalkylamino groups. The chemical procedures described in the application WO-9633980 can be used to prepare the 3-cyanoquinoline intermediates used in this invention wherein $R_1$, $G_1$, $G_2$, or $R_4$ are aminoalkylalkoxy groups. The chemical procedures described in the application WO-9633979 can be used to prepare the 3-cyanoquinoline intermediates used in this invention wherein $R_1$, $G_1$, $G_2$, or $R_4$ are alkoxyalkylamino groups. The chemical procedures described in the application WO-9633978 can be used to prepare the 3-cyanoquinoline intermediates used in this invention wherein $R_1$, $G_1$, $G_2$, or $R_4$ are aminoalkylamino groups. The chemical procedures described in the application WO-9633977 can be used to prepare the 3-cyanoquinoline intermediates used in this invention wherein $R_1$, $G_1$, $G_2$, or $R_4$ are aminoalkylalkoxy groups. Athough the above patent applications describe compounds where the indicated functional group have been introduced onto the 6-position of a quinazoline, the same chemistry can be used to introduce the same groups unto positions occupied by the $R_1$, $G_1$, $G_2$, and $R_4$ substituents of the compounds of this invention.

Representative compounds of this invention were evaluated in several standard pharmacological test procedures that showed that the compounds of this invention possess significant activity as inhibitors of protein tyrosine kinases, and are antiproliferative agents. Based on the activity shown in the standard pharmacological test procedures, the compounds of this invention are therefore useful as antineoplastic agents. The test procedures used and results obtained are shown below.

Inhibition of Epidermal Growth Factor Receptor Kinase (EGF-R) Using Recombinant Enzyme Representative test compounds were evaluated for their ability to inhibit the phosphorylation of the tyrosine residue of a peptide substrate catalyzed by the enzyme epidermal growth factor receptor kinase. The peptide substrate (RR-SRC) has the sequence arg-arg-leu-ile-glu-asp-ala-glu-tyr-ala-ala-arg-gly. The enzyme used in this assay is the His-tagged cytoplasmic domain of EGFR. A recombinant baculovirus ($vHcEGFR_{52}$) was constructed containing the EGFR cDNA encoding amino acids 645-1186 preceded by Met—Ala—$(His)_6$. Sf9 cells in 100 mm plates were infected at an moi of 10 pfu/cell and cells were harvested 48 h post infection. A cytoplasmic extract was prepared using 1% Triton X-100 and applied to Ni-NTA column. After washing the column with 20 mM imidazole, HcEGFR was eluted with 250 mM imidazole (in 50 mM $Na_2HPO_4$, pH 8.0, 300 mM NaCl). Fractions collected were dialyzed against 10 mM HEPES, pH 7.0, 50 mM NaCl, 10% glycerol, 1 ug/mL antipain and leupeptin and 0.1 mM Pefabloc SC. The protein was frozen in dry ice/methanol and stored −70° C.

Test compounds were made into 10 mg/mL stock solutions in 100% dimethylsulfoxide (DMSO). Prior to experiment, stock solutions were diluted to 500 uM with 100% DMSO and then serially diluted to the desired concentration with HEPES buffer (30 mM HEPES pH 7.4).

For the enzyme reaction, 10 μL of each inhibitor (at various concentrations) were added to each well of a 96-well plate. To this was added 3 μL of enzyme (1:10 dilution in 10 mM HEPES, pH 7.4 for final conc. of 1:120). This was allowed to sit for 10 min on ice and was followed by the addition of 5 μl peptide (80 μM final conc.), 10 μl of 4×Buffer (Table A), 0.25 μL $^{33}$P-ATP and 12 μL $H_2O$. The reaction was allowed to run for 90 min at room temperature and was followed by spotting the entire volume on to precut P81 filter papers. The filter discs were washed 2× with 0.5% phosphoric acid and radioactivity was measured using a liquid scintillation counter.

TABLE A

| Reagent | Final | 100 Rxns |
|---|---|---|
| 1M HEPES (pH 7.4) | 12.5 mM | 50 μL |
| 10 mM $Na_3VO_4$ | 50 uM | 20 μL |
| 1M $MnCl_2$ | 10 mM | 40 μL |
| 1 mM ATP | 20 uM | 80 μL |
| $^{33}$P-ATP | 2.5 uCi | 25 μL |

The inhibition data for representative compounds of the invention are shown below in TABLE 1. The $IC_{50}$ is the concentration of test compound needed to reduce the total amount of phosphorylated substrate by 50%. The % inhibition of the test compound was determined for at least three different concentrations and the $IC_{50}$ value was evaluated from the dose response curve. The % inhibition was evaluated with the following formula:

$$\% \text{ inhibition}=100-[\text{CPM(drug)}/\text{CPM(control)}]\times 100$$

where CPM(drug) is in units of counts per minute and is a number expressing the amount of radiolabled ATP (g-$^{33}$P) incorporated onto the RR-SRC peptide substrate by the enzyme after 90 minutes at room temperature in the presence of test compound as measured by liquid scintillation counting. CPM(control) is in units of counts per minute and was a number expressing the amount of radiolabled ATP (g-$^{33}$P) incorporated into the RR-SRC peptide substrate by the enzyme after 90 minutes at room temperature in the absence of test compound as measured by liquid scintillation counting. The CPM values were corrected for the background counts produced by ATP in the absence of the enzymatic reaction. The $IC_{50}$ values in TABLE 1 are averages of the individual determinations.

TABLE 1

(recombinant enzyme)
Inhibition of Epidermal Growth Factor Receptor Kinase

| Compound | IC50 (μM) | Number of Tests |
|---|---|---|
| 72 | 0.006 | 1 |
| 74 | 0.01 | 1 |
| 75 | 0.0004 | 2 |
| 76 | 0.01 | 2 |
| 77 | 0.006 | 1 |
| 79 | 0.00036 | 3 |
| 82 | 0.05 | 1 |
| 93 | 1.0 | 1 |
| 95 | 0.005 | 1 |
| 96 | 0.1 | 1 |
| 108 | 0.026 | 2 |
| 106 | 0.013 | 2 |
| 107 | 0.5 | 1 |
| 109 | 0.007 | 2 |
| 89 | 0.01 | 1 |
| 115 | 0.005 | 1 |
| 91 | 0.015 | 1 |
| 119 | 0.00005 | 1 |
| 103 | 0.008 | 2 |

Inhibition of Epithelial Cell Kinase (ECK)

In this standard pharmacological test procedure, a biotinylated peptide substrate is first immobilized on neutravidincoated microtiter plates. The test drug, the Epithelial Cell Kinase (ECK), $Mg^{++}$, sodium vanadate (a protein tyrosine phosphatase inhibitor), and an appropriate buffer to maintain pH (7.2) are then added to the immobilized substrate-containing microtiter wells. ATP is then added to initiate phosphorylation. After incubation, the assay plates are washed with a suitable buffer leaving behind phosphorylated peptide which is exposed to horse radish peroxidase (HRP)-conjugated anti-phosphotyrosine monoclonal antibody. The antibody-treated plates are washed again and the HRP activity in individual wells is quantified as a reflection of degree of substrate phosphorylation. This nonradioactive format was used to identify inhibitors of ECK tyrosine kinase activity where the $IC_{50}$ is the concentration of drug that inhibits substrate phosphorylation by 50%. The results obtained for representative compounds of this invention are listed in TABLE 2. Multiple entries for a given compound indication it was tested multiple times.

Inhibition of Kinase Insert Domain Containing Receptor (KDR: the catalytic domain of the VEGF receptor)

In this standard pharmacological test procedure, KDR protein is mixed, in the presence or absence of a inhibitor compound, with a substrate peptide to be phosphorylated (a copolymer of glutamic acid and tyrosine, E:Y::4:1) and other cofactors such as $Mg^{++}$ and sodium vanadate (a protein tyrosine phosphatase inhibitor) in an appropriate buffer to maintain pH (7.2). ATP and a radioactive tracer (either $P^{32}$- or $P^{33}$- labeled ATP) is then add to initiate phosphorylation. After incubation, the radioactive phosphate associated with the acid-insoluble fraction of the assay mixture is then quantified as reflection of substrate phosphorylation. This radioactive format was used to identify inhibitors of KDR tyrosine kinase activity where the $IC_{50}$ is the concentration of drug that inhibits substrate phosphorylation by 50%. The results obtained for representative compounds of this invention are listed in TABLE 2. Multiple entries for a given compound indication it was tested multiple times.

Mitogen Activated Protein Kinase (MAPK) Assay

To evaluate inhibitors of the MAP (mitogen activated protein) kinase a two component coupled standard pharmacological test procedure, which measures phosphorylation of a serine/threonine residue in an appropriate sequence in the substrate in the presence and absence of a putative inhibitor, was used. Recombinant human MEK 1 (MAPKK) was first used to activate recombinant human ERK2 (MAPK) and the activated MAPK (ERK) was incubated with substrate (MBP peptide or MYC peptide) in the presence of ATP, $Mg^{+2}$ and radiolabeled $^{33}P$ ATP. The phosphorylated peptide was captured on a P 81 phosphocellulose filter (paper filter or embedded in microtiter plate) washed and counted by scintillation methods.

The peptide substrates used in the assay are MBP, peptide substrate (APRTPGGRR), or synthetic Myc substrate, (KKFELLPTPPLSPSRR•5 TFA. The recombinant enzymes used were prepared as GST fusion proteins of human ERK 2 and human MEK 1. Inhibitor samples were prepared as 10× stocks in 10% DMSO and an appropriate aliquot was used to deliver either 10 ug/ml for a single point screening dose or 100, 10, 1, and 0.1 uM final concentration for a dose response curve. Final DMSO concentrations were less than or equal to 1%.

The reaction was run as follows in 50 mM Tris kinase buffer, pH 7.4 in a reaction volume of 50 ul. The appropriate volume of kinase buffer and inhibitor sample was added to the tube. Appropriate dilution of enzyme was delivered to give 2-5 ug recombinant MAPK (Erk) per tube. The inhibitor was incubated with MAPK (Erk) for 30 min at 0 deg. C. Recombinant Mek (MAPKK) (0.5-2.5 ug) or fully activated Mek (0.05-0.1 units) was added to activate the Erk and incubated for 30 min at 30° C. Then substrate and gamma $^{33}P$ ATP was were added to give a final concentration of 0.5-1 mM MBPP or 250-500 uM Myc; 0.2-0.5 uCi gamma P 33 ATP/tube; 50 μM ATP final concentration. Samples were incubated at 30° C. for 30 minutes and the reaction was stopped by adding 25 μl of ice cold 10% TCA . After samples were chilled on ice for 30 min, 20 μl of sample was transferred onto P 81 phosphocellulose filter paper or appropriate MTP with embedded P 81 filter. Filter papers or MTP were washed 2 times with a large volume of 1% acetic acid, then 2 times with water. The filters or MTP were briefly air dried before addition of scintillant and samples were counted in the appropriate scintillation counter set up for reading $^{33}P$ isotope. Samples included a positive control (activated enzyme plus substrate); a no enzyme control; a no substrate control; samples with different concentrations of putative inhibitor; and samples with reference inhibitors (other active compounds or non-specific inhibitors such as staurosporine or K252 B).

The raw data was captured as cpm. Sample replicates were averaged and corrected for background count. Mean cpm data was tabulated by group and % inhibition by a test compound was calculated as (corrected cpm control-corrected. cpm sample/control) X 100=% inhibition. If several concentrations of inhibitor were tested, $IC_{50}$ values (the concentration which gives 50% inhibition) were determined graphically from the dose response curve for % inhibition or by an appropriate computer program. The results obtained for representative compounds of this invention are listed in TABLE 2 where there may be separate entries for the same compound; this is an indication that the compound was evaluated more than one time.

TABLE 2

Inhibition of Kinase insert Domain containing Receptor (KDR), Epithelial Cell Kinase (Eck), and Mitogen Activated Protein Kinase (Mek-Erk)

| Example | VEGF μM | Eck μM | Mek and Erk μM | erbB2 % Inh 2 μg/mL |
|---|---|---|---|---|
| 72 | | >41.724 | >100 | 96 |
| 74 | | >42.982 | >100 | 95 |
| 75 | | >37.284 | 100 | |
| 76 | | >40.617 | >100 | 96 |
| 77 | | 42.162 | >100 | 105 |
| 78 | | >21.269 | 40 | 53 |
| 79 | | >38.610 | 80 | |
| 82 | >1.8315 | >1.832 | 30 | |
| 85 | | >21.584 | 10 | 87 |
| | | | 4 | |
| | | | 1.8 | |
| | | | 1.8 | |

Inhibition of Cancer Cell Growth as Measured by Cell Number

Human tumor cell lines were plated in 96-well plates (250 μl/well, 1-6×$10^4$ cells/ml) in RPMI 1640 medium, containing 5% FBS (Fetal Bovine Serum). Twenty four hours after plating, test compounds were added at five log concentrations (0.01-100 mg/ml) or at lower concentrations for the more potent compounds. After 48 hours exposure to test compounds, cells were fixed with trichloroacetic acid, and stained with Sulforhodamine B. After washing with trichloroacetic acid, bound dye was solubilized in 10 mM Tris base and optical density was determined using plate reader. Under conditions of the assay the optical density is proportional to the number of cells in the well. $IC_{50}$s (concentrations causing 50% inhibition of cell growth) were determined from the growth inhibition plots. The test procedure is described in details by Philip Skehan et. al, J.Natl. Canc. Inst., 82, 1107-1112 (1990). These data are shown below in TABLE 3. Information about some of the cell lines used in these test procedures is available from the American Type Tissue Collection: Cell Lines and Hybridomas, 1994 Reference Guide, 8th Edition.

TABLE 3

Inhibition of Cancer Cell Growth as Measured by Cell Number ($IC_{50}$ μg/mL)

| Example | MDAMB435 | SW620 | A431 | SKBR3 | 3T3 | Her2/3T3 |
|---|---|---|---|---|---|---|
| 85 | 27.6 | 17.98 | 4.91 | 1.74 | | |
| 75 | 0.2 | 0.5 | 0.1 | 0.04 | | |
| 74 | 3.9 | 0.6 | 0.9 | 1.0 | | |
| 72 | 3.5 | 0.4 | 0.9 | 0.8 | | |
| 77 | 0.1 | 0.1 | 0.03 | 0.02 | | |
| 79 | 0.3 | 0.1 | 0.04 | 0.01 | | |
| 76 | 0.284 | 0.239 | 0.050 | 0.031 | | |

TABLE 3-continued

Inhibition of Cancer Cell Growth as Measured by Cell Number ($IC_{50}$ μg/mL)

| Example | MDAMB435 | SW620 | A431 | SKBR3 | 3T3 | Her2/3T3 |
|---|---|---|---|---|---|---|
| 78 | 3.194 | >5 | 0.369 | 1.495 | | |
| 91 | 1.83 | 1.73 | 0.232 | 0.181 | 2.87 | 0.375 |
| 89 | 2.07 | 1.53 | 0.245 | 0.107 | 2.04 | 0.192 |
| 90 | 1.74 | 1.24 | 0.234 | 0.148 | 2.1 | 0.329 |
| 92 | 3.32 | 2.51 | 0.283 | 0.188 | 2.79 | 0.35 |

In Vivo Inhibition of the Growth of Human Epidermoid Tumors (A431)

BALB/c nu/nu female mice (Charles River, Wilmington, Mass.) were used in the in vivo standard pharmacological test procedures. Human epidermoid carcinoma cells A-431 (American Type Culture Collection, Rockville, Md. #CRL-155) were grown in vitro as described above. A unit of 5×$10^6$ cells were injected SC into mice. When tumors attained a mass of between 100 and 150 mg, the mice were randomized into treatment groups (day zero). Mice were treated IP or PO once a day either on days 1, 5, and 9 or on days 1 through 10 post staging with doses of either 80, 40 or 20, or 10 mg/kg/dose of the compound to be evaluated in 0.2% Klucel. Control animals received no drug. Tumor mass was determined every 7 days [(length×width$^2$)/2] for 28 days post staging. Relative tumor growth (Mean tumor mass on day 7, 14, 21, and 28 divided by the mean tumor mass on day zero) is determined for each treatment group. The % T/C (Tumor/Control) is determined by dividing the relative tumor growth of the treated group by the relative tumor growth of the placebo group and multiplying by 100. A compound is considered to be active if the % T/C is found to be significantly less than 100%.

The ability of the compound of Example 92 to inhibit the growth of human epidermoid tumors (A431) in vivo demonstrated below in TABLE 4 below.

TABLE 4

In Vivo Inhibition of the Growth of Human Epidermoid Tumors (A431) in Mice by the Compound of Example 92

| a | b | c,d | b | c,d | b | c,d | b | c,d | e |
|---|---|---|---|---|---|---|---|---|---|
| Drug Treatment mg/kg/dose | Day 7 | % T/C | Day 14 | % T/C | Day 20 | % T/C | Day 28 | % T/C | S/T |
| 0.5% Methocel 0.4% Tween 80 | 5.51 | | 10.43 | | 12.36 | | 14.18 | | 10/10 |
| Example 92 (40 PO) | 1.49 | 27* | 1.58 | 15* | 2.60 | 21* | 6.22 | 44 | 5/5 |
| Example 92 (10 PO) | 3.94 | 72 | 10.41 | 100 | 14.76 | 119 | 22.51 | 159 | 5/5 |

a compound administered on days 1 through 10 PO.

$$\text{b Relative Tumor Growth} = \frac{\text{Mean Tumor Mass on Day 7, 14, 21, 28}}{\text{Mean Tumor Mass on Day 0}}$$

$$\text{c \% T/C} = \frac{\text{Relative Tumor Growth of Treated Group}}{\text{Relative Tumor Growth of Placebo Group}} \times 100$$

d Statistical Analysis (Student's T-test) of Log Relative Tumor Growth.

*Indicates statistically ($p < 0.01$) significant reduction in Relative Tumor Growth of Treated Group compared to the Placebo Control.

e S/T = # of Survivors/# of Treated on Day +28 post tumor staging.

As indicated by the results presented in TABLE 4, the compound of Example 92 is an effective inhibitor of tumor growth in vivo when given orally at 40 mg/Kg.

The ability of the compound of Example 89 to inhibit the growth of human epidermoid tumors (A431) in vivo demonstrated below in TABLE 5 below.

TABLE 5

In Vivo Inhibition of the Growth of Human Epidermoid Tumors (A431) in Mice by the Compound of Example 89

| a | b | c,d | b | c,d | b | c,d | b | c,d | e |
|---|---|---|---|---|---|---|---|---|---|
| Drug Treatment mg/kg/dose | Day 7 | % T/C | Day 14 | % T/C | Day 21 | % T/C | Day 28 | % T/C | S/T |
| 0.5% Methocel 0.4% Tween 80 | 4.18 | | 10.44 | | 15.08 | | 28.23 | | 9/10 |
| Example 89 (40 PO) | 0.49 | 11* | 0.58 | 6* | 3.11 | 21* | 7.20 | 26* | 5/5 |
| Example 89 (10 PO) | 2.09 | 50* | 3.37 | 32* | 5.76 | 38* | 7.24 | 26* | 4/5 |

a compound administered on days 1 through 10 PO.

b Relative Tumor Growth = $\frac{\text{Mean Tumor Mass on Day 7, 14, 21, 28}}{\text{Mean Tumor Mass on Day 0}}$ c % T/C = $\frac{\text{Relative Tumor Growth of Treated Group}}{\text{Relative Tumor Growth of Placebo Group}} \times 100$ d Statistical Analysis (Student's T-test) of Log Relative Tumor Growth.

*Indicates statistically ($p < 0.01$) significant reduction in Relative Tumor Growth of Treated Group compared to the Placebo Control.

e S/T = # of Survivors/# of Treated on Day +28 post tumor staging.

As indicated by the results presented in TABLE 5, the compound of Example 89 is an effective inhibitor of tumor growth in vivo when given orally at 40 mg/Kg and 10 mg/Kg.

Based on the results obtained for representative compounds of this invention, the compounds of this invention are antineoplastic agents which are useful in treating, inhibiting the growth of, or eradicating neoplasms. In particular, the compounds of this invention are useful in treating, inhibiting the growth of, or eradicating neoplasms that express EGFR such as those of the breast, kidney, bladder, mouth, larynx, esophagus, stomach, colon, ovary, or lung. In addition, the compounds of this invention are useful in treating, inhibiting the growth of, or eradicating neoplasms of the breast that express the receptor protein produced by the erbB2 (Her2) oncogene. Based on the results obtained, the compounds of this invention are also useful in the treatment of polycystic kidney disease.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of body weight, optionally given in divided doses two to four times a day, or in sustained release form. The total daily dosage is projected to be from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention can be administered in combination with other antitumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, and antiestrogens such as tamoxifen.

The preparation of representative examples of the compounds of this invention is described below.

EXAMPLE 1

1,4-Dihydro-7-methoxy-4-oxo-quinoline-3-carbonitrile

A mixture of 30.2 g (245.2 mmol) of 3-methoxy aniline and 41.5 g (245.2 mmol) of ethyl(ethoxymethylene) cyanoacetate was heated in the absence of solvent to 140° C. for 30 minutes. To the resulting oil was added 1200 ml of Dowtherm. The solution was refluxed with stirring under nitrogen for 22 hours. The mixture was cooled to room temperature and solid was collected and washed with hexanes. The solid was recrystallized from acetic acid to give 17 g of 1,4-dihydro-7-methoxy-4-oxo-quinoline-3-carbonitrile: mass spectrum (electrospray, m/e): M+H 200.9.

EXAMPLE 2

1,4-Dihydro-7-methoxy-6-nitro-4-oxo-quinoline-3-carbonitrile

To a suspension of 10 g (49.6 mmol) of 1,4-dihydro-7-methoxy-4-oxo-quinoline-3-carbonitrile in 160 ml of trifluroacetic anhydride was added 6 g (74.9 mmol) of ammonium nitrate over a period of 3 hours. The mixture was stirred an additional two hours. Excess anhydride was removed at reduced pressure at 45° C. The residue was stirred with 500 ml of water. The solid was collected and washed with water. The solid was dissolved in 1000 ml of boiling acetic acid and the solution was treated with decolorizing charcoal. The mixture was filtered and concentrated to a volume of 300 ml. Cooling gave a solid which was collected giving 5.4 g of 1,4-dihydro-7-methoxy-6-nitro-4-oxo-quinoline-3-carbonitrile as a brown solid: mass spectrum (electrospray, m/e): M+H 246.

EXAMPLE 3

4-Chloro-7-methoxy-6-nitro -quinoline-3-carbonitrile

A mixture of 5.3 g (21.6 mmol) of 1,4-dihydro-7-methoxy-6-nitro-4-oxo-quinoline-3-carbonitrile and 9 g (43.2 mmol) of phosphorous pentachloride was heated at 165° C. for 2 hours. The mixture was diluted with hexanes and the solid was collected. The solid was dissolved in 700 ml ethyl acetate and washed with cold dilute sodium hydroxide solution. The solution was dried over magnesium sulfate and filtered through a pad of silica gel giving 5.2 g of 4-chloro-7-methoxy-6-nitro-quinoline-3-carbonitrile as a tan solid.

EXAMPLE 4

4-[(3-Bromophenyl)amino]-7-methoxy-6-nitro-quinoline-3-carbonitrile

A solution of 5.2 g (19.7 mmol) of 4-chloro-7-methoxy-6-nitro-quinoline-3-carbonitrile and 3.7 g (21.7 mmol) of 3-bromo aniline in 130 ml of methoxyethanol was refluxed under nitrogen for 4 hours. The reaction mixture was poured into dilute sodium bicarbonate solution. Solid was collected and washed with water and dried in air. The solid was chromatographed on silica gel eluting with chloroform-ethyl acetate 9:1. Solvent was removed from product fractions giving 1.2 g of 4-[(3-bromophenyl)amino]-7-methoxy-6-nitro-quinoline-3-carbonitrile as a yellow solid: mass spectrum (electrospray, m/e): M+H 399.0, 402.0.

EXAMPLE 5

6-Amino-4-[(3-bromophenyl)amino]-7-methoxy-quinoline-3-carbonitrile

A mixture of 2.05 g (5.1 mmol) of 4-[(3-bromophenyl) amino]-7-methoxy-6-nitro-quinoline-3-carbonitrile, 1.37 g (25.7 mmol) of ammonium chloride, and 0.86 g (15.4 mmol) of powdered iron was stirred at reflux in 26 ml water and 26 ml methanol for 2 hours. The mixture was diluted with ethyl acetate and the hot mixture was filtered. The organic layer was separated from the filtrate and dried over magnesium sulfate. The solvent was removed and the residue was chromatographed on silica gel eluting with mixtures of chloroform and ethyl acetate. Product fractions were combined to give 1.3 g of 6-amino-4-[(3-bromophenyl)amino]-7-methoxy-quinoline-3-carbonitrile as a yellow solid: mass spectrum (electrospray, m/e): M+H 369.1, 371.1.

EXAMPLE 6

2-Cyano-3-(4-nitrophenylamino)acrylic Acid Ethyl Ester

4-Nitroaniline (60.0 g, 0.435 mol) and ethyl (ethoxymethylene) cyanoacetate (73.5 g, 0.435 mol) were mixed mechanically in a flask. The mixture was heated at 100° C. for 0.5 h after it had melted and resolidified. A 114 g portion of the crude product was recrystallized from dimethylformamide to give 44.2 g of yellow crystals; mp 227-228.5° C.

EXAMPLE 7

1,4-Dihydroquinoline-6-nitro-4-oxo-3-carbonitrile

A slurry of 25.0 g (95.8 mmol) of 2-cyano-3-(4-nitrophenylamino)acrylic acid ethyl ester in 1.0 L of Dowtherm A was heated at 260° C. under $N_2$ for 12.5 h. The cooled reaction was poured into 1.5 L of hexane. The product was collected, washed with hexane and hot ethanol and dried in vacuo. There was obtained 18.7 g of brown solid. An analytical sample was obtained by recrystallization from dimethylformamide/ethanol: mass spectrum (electrospray, m/e): M+H 216.

EXAMPLE 8

4-Chloro-6-nitro-quinoline-3-carbonitrile

A mixture of 31.3 g (0.147 mol) of 6-nitro-4-oxo-1,4-dihydro-quinoline-3-carbonitrile and 160 mL of phosphorous oxychloride was refluxed for 5.5 h. The phosphorous oxychloride was removed in vacuo and the residue was poured over ice and neutralized with sodium bicarbonate. The product was collected, washed with water and dried in vacuo (50° C.). There was obtained 33.5 g of tan solid; solid: mass spectrum (electrospray, m/e): M+H 234.

EXAMPLE 9

4-[(3-Bromophenyl)amino]-6-nitro-quinoline-3-carbonitrile

A mixture of 17.0 g (73.1 mmol) of 4-chloro-6-nitro-quinoline-3-carbonitrile and 15.1 g (87.7 mmol) of 3-bromoaniline in 425 mL of ethanol was refluxed for 5 h. Saturated sodium bicarbonate was added and then all volatile material was removed in vacuo. The residue was slurried with hexane and the product was collected and washed with hexane. The crude product was washed with water and dried in vacuo(60° C.). There was obtained 22.5 g of yellow solid. An analytical sample was obtained by recrystallization from ethyl acetate; mp 258-259° C.

EXAMPLE 10

6-Amino-4-[(3-bromophenyl)amino]-quinoline-3-carbonitrile

A mixture of 4.00 g (10.8 mmol) of 4-[(3-bromophenyl)amino]-6-nitro-quinoline-3-carbonitrile and 12.2 g (54.2 mmol) of $SnCl_2$ dihydrate in 160 mL of ethanol was refluxed under $N_2$ for 1.3 h. After cooling to 25° C., ice water and sodium bicarbonate were added and the mixture was stirred for 2 h. Extraction with chloroform, treatment with Darco, drying (magnesium sulfate) and solvent removal gave 3.9 g of brown crystals: mass spectrum (electrospray, m/e): M+H 339.

EXAMPLE 11

4-[(3,4-Dibromophenyl)amino]-6-nitro-quinoline-3-carbonitrile

A mixture of 6.20 g (26.6 mmol) of 4-chloro-6-nitro-quinoline-3-carbonitrile and 8.00 g (31.9 mmol) of 3,4-dibromoaniline in 160 mL of ethanol was refluxed under $N_2$ for 5 h. Saturated sodium bicarbonate was added and volatile material was removed. The residue was slurried with hexane, collected, washed with hexane and water and dried. The insoluble material was repeatedly extracted with boiling ethyl acetate and the solution was then filtered through silica gel. The solvent was removed to give 3.80 g of green solid: mass spectrum (electrospray, m/e): M+H 449.

EXAMPLE 12

6-Amino-4-[(3,4-dibromophenyl)amino]-quinoline-3-carbonitrile

A mixture of 4.90 g (10.9 mmol) of 4-[(3,4-dibromophenyl)amino]-6-nitro-quinoline-3-carbonitrile and 12.4 g (54.7 mmol) of $SnCl_2$ dihydrate in 200 mL of ethanol was refluxed under $N_2$ for 1.5 h. After cooling to 25° C., the reaction was diluted with ice water, neutralized with sodium bicarbonate and stirred for 2 h. This solution was then extracted with chloroform, treated with Darco, dried (magnesium sulfate) and evaporated. After drying in vacuo (40° C.), there was obtained 1.25 g of brown solid: mass spectrum (electrospray, m/e): M+H 417, 419, 421.

EXAMPLE 13

6-Nitro-4-[(3-trifluoromethylphenyl)amino]-quinoline-3-carbonitrile

A mixture of 10.6 g (45.7 mmol) of 4-chloro-6-nitro-quinoline-3-carbonitrile and 8.82 g (54.8 mmol) of 3-(trifluoromethyl)aniline in 270 mL of ethanol was refluxed under $N_2$ for 5 h. The reaction was diluted with ethanol, neutralized with satd sodium bicarbonate and evaporated. The residue was slurried with hexane, collected, washed with hexane and water and dried in vacuo (60° C.) to give 10.9 g of yellow solid. A 2.00 g sample was recrystallized from ethanol to give 1.20 g of bright yellow solid; mp 260-261° C.

EXAMPLE 14

6-Amino-4-[(3-trifluoromethylphenyl)amino]-quinoline-3-carbonitrile

A slurry of 6.00 g (16.8 mmol) of 6-nitro-4-[(3-trifluoromethylphenyl)amino]quinoline-3-carbonitrile and 18.9 g (83.3 mmol) of $SnCl_2$ dihydrate in 240 mL of ethanol was refluxed under $N_2$ for 1 h. After cooling to 25° C., the reaction was diluted with ice water, neutralized with sodium bicarbonate and stirred for 2 h. The product was extracted with chloroform, treated with Darco, dried(magnesium sulfate) and evaporated. The residue was filtered through silica gel (10% methanol in chloroform), evaporated and dried in vacuo (40° C.) to give 4.87 g of brown solid: mass spectrum (electrospray, m/e): M+H 329.

EXAMPLE 15

4-Bromo-but-2-enoic Acid [4-(3-bromo-phenylamino)-3-cyano-quinolin-6-yl]-amide

A solution of 1.65 grams (0.01 mole) of 4-bromo crotonic acid (Giza Braun, J. Am. Chem. Soc. 52, 3167 1930) in 15ml of dichloromethane was treated with 1.74 ml (0.02 moles) of oxalyl chloride and 1 drop of N,N-dimethylformamide. After an hour the solvents were removed on the rotary evaporator. The 4-bromo crotonyl chloride was taken up in 25 ml of tetrahydrofuran, and 3.39 grams of 6-Amino-4-(3-bromophenylamino)-quinoline-3-carbonitrile in 25 ml of tetrahydrofuran was added dropwise. This was followed by the dropwise addition of 1.92 ml (0.011 moles) of diisopropylethylamine. After the addition of 25 ml of water and 50 ml of ethyl acetate, the layers were separated. The organic layer was dried over anhydrous sodium sulfate, and taken to a solid in vacuo. This solid was digested for an hour with refluxing ethyl acetate then filtered from the ethyl acetate while still hot. Thus was obtained 3.31 grams (68%) of 4-bromo-but-2-enoic acid [4-(3-bromo-phenylamino)-3-cyano-quinolin-6-yl]-amide.

EXAMPLE 16

2-Cyano-3-(2-methyl-4-nitrophenyl)acrylic Acid Ethyl Ester

A mixture of 2-methyl-4-nitroaniline (38.0 g, 250 mmol), ethyl (ethoxymethylene)cyanoacetate (50.8 g, 300 mmol), and 200 ml of toluene was refluxed for 24 h, cooled, diluted with 1:1 ether-hexane, and filtered. The resulting white solid was washed with hexane-ether and dried to give 63.9 g, mp 180-210° C.

EXAMPLE 17

1,4-Dihydroguinoline-8-methyl-6-nitro-3-carbonitrile

A stirred mixture of 64 g (230 mmol) of 2-cyano-3-(2-methyl-4-nitrophenyl)acrylic acid ethyl ester and 1.5 L of Dowtherm A was heated at 260° C. for 12 h, cooled, diluted with hexane, and filtered. The grey solid thus obtained was washed with hexane and dried to give 51.5 g, mp 295-305° C.

EXAMPLE 18

4-Chloro-8-methyl-6-nitro-quinoline-3-carbonitrile

A stirred mixture of 1,4-dihydroquinoline-8-methyl-6-nitro-3-carbonitrile (47 g, 200 mmol) and 200 ml of phosphorous oxychloride was refluxed for 4 h. The phosphorous oxychloride was removed in vacuo, and the residue was stirred with methylene chloride at 0° C. and treated with a slurry of ice and sodium carbonate. The organic layer was separated and washed with water. The solution was dried and concentrated to a volume of 700 ml. The product was precipitated by the addition of hexane and cooling to 0° C. The white solid was filtered off and dried to give 41.6 g, mp 210-212° C.

EXAMPLE 19

4-[(3-Bromophenyl)amino]-8-methyl-6-nitro-quinoline-3-carbonitrile

A stirred mixture of 4-chloro-8-methyl-6-nitro-quinoline-3-carbonitrile (14.8 g, 60 mmol), 3-bromoaniline (12.4 g, 72 mmol), pyridine hydrochloride (6.93 g, 60 mmol), and 180 ml of ethoxyethanol was refluxed for 1.5 h, cooled, poured into a stirred mixture of water and an amount of sodium carbonate to give a $_pH$ of 8-9. The resulting yellow solid was filtered, washed with water, dried, digested in boiling ether, filtered, and dried to give 22.6 g, mp 263-267° C.

EXAMPLE 20

4-[(3-Bromophenyl)-N-acetylamino]-8-methyl-6-nitro-quinoline-3-carbonitrile

A stirred mixture of 4-[(3-bromophenyl)amino]-8-methyl-6-nitro-quinoline-3-carbonitrile (15.3 g, 40 mmol), 0.37 g (3 mmol) of dimethylaminopyridine, 40 ml of acetic anhydride, and 80 ml of pyridine was refluxed for 3 h and concentrated at 50° C. under vacuum. The residue was stirred with methylene chloride and 0.1 N HCl. After filtration through Celite, the organic layer was washed with water, dried and concentrated. The residue was subjected to chromatography on silica gel with 1% acetic acid in methylene chloride to give 11.2 g of an amber glass, NMR ($CDCl_3$) d 2.29 (N-acetyl group).

EXAMPLE 21

8-Bromomethyl-4-[(3-bromophenyl)-N-acetylamino]-6-nitro-quinoline-3-carbonitrile A stirred mixture of 4-[(3-bromophenyl)-N-acetylamino]-8-methyl-6-nitro-quinoline-3-carbonitrile (10.6 g, 25 mmol), N-bromosuccinimide (6.68 g, 37.5 mmol), 0.30 g of dibenzoyl peroxide, and 200 ml of carbon tetrachloride was refluxed for 2 h, treated with an additional 0.30 g of dibenzoyl peroxide, and refluxed an additional 2.5 h, cooled, diluted with methylene chloride, and stirred with aqueous sodium bisulfite. The organic layer was separated and washed successively with water, sodium bicarbonate solution, and water. The solution was dried and evaporated to give 15 g of a white foam, NMR ($CDCl_3$) d 5.19 (dd, $CH_2Br$).

EXAMPLE 22

4-[(3-Bromophenyl)amino]-8-dimethylaminomethyl-6-nitro-quinoline-3-carbonitrile

To a stirred solution of dimethylamine in THF (2.0 M; 115 ml; 230 mmol) at 0° C. was added a solution of 8-bromomethyl 4-[(3-bromophenyl)-N-acetylamino]-6-nitro-quinoline-3-carbonitrile (11.6 g, 23 mmol) in 115 ml of THF during 15 m. After warming to 25° C. the mixture was stirred for 2 h. The THF was evaporated off, and the residue was refluxed in 230 ml of methanol with 12.7 g (92 mmol) of potassium carbonate for 1 h. The mixture was cooled, saturated with $CO_2$, and concentrated. The residue was partitioned with methylene chloride and water. The organic layer was washed with water, dried, and concentrated. The residue was subjected to chromatography on silica gel with methylene chloride-ethyl acetate-methanol-triethylamine to give 6.0 g yellow solid, mp 223-226° C.

EXAMPLE 23

6-Amino-4-[(3-bromophenyl)amino]-8-dimethylaminomethyl-quinoline-3-carbonitrile

A stirred mixture of 4-[(3-bromophenyl)amino]-8-dimethylaminomethyl-6-nitro-quinoline-3-carbonitrile (5.98 g, 14.1 mmol), iron powder (2.76 g, 49 mg-atoms), acetic acid (5.67 ml, 99 mmol), and 70 ml of methanol was refluxed for 2 h and then evaporated to remove methanol. The residue was stirred with water for 10 m, and the orange solid was filtered off and washed with 2% acetic acid. The total filtrate was basified to $_pH$ 10 with 5 N sodium hydroxide. The resulting precipitate was extracted with methylene chloride. The extract was washed with water, dried, and concentrated. The residue was subjected to chromatography on silica gel with ethyl acetate-methanol-triethylamine to give 3.34 g of amber solid; mass spectrum (electrospray, m/e) M+H 396.2, 398.1.

EXAMPLE 24

6-Amino-4-[(3-iodophenyl)amino]-quinoline-3-carbonitrile

A mixture of 6.70 g (16.1 mmol) 4-[(3-iodophenyl)amino]-6-nitro-quinoline-3-carbonitrile, 300 ml ethanol, and 18.2 g (80.5 mmol) $SnCl_2$ dihydrate was heated to reflux under $N_2$. Removed heat at 2 hours, added ice water. Added sodium bicarbonate until pH was basic, forming a thick yellow mixture. Stirred for 2½ hours. Extracted with chloroform, stirred organic portion with Darco and filtered through magnesium sulfate. Stripped solvent and dried in vacuo, giving 3.48 g of yellow-brown solid: mass spectrum (electrospray m/e): M+H=387.0.

EXAMPLE 25

4-[(3-Iodophenyl)amino]-6-nitro-quinoline-3-carbonitrile

A mixture of 3.10 ml (25.7 mmol) 3-iodoaniline, 200 ml ethanol, and 5.00 g (21.4 mmol) 4-chloro-6-nitro-quinoline-3-carbonitrile was heated to reflux under $N_2$ for 3½ hours. Cooled and made basic with a saturated sodium bicarbonate. Stripped solvents and azeotroped with ethanol. Slurried residue with hexane and collected. Air dried, washed solids with water, and dried in vacuo. Dissolved solids in 400 ml ethyl acetate, stirred with Darco, filtered and removed solvent. Dried solids in vacuo to give 7.38 g of yellow solid: mass spectrum (electrospray m/e): M+H=417.0.

EXAMPLE 26

6-Amino-4-[(3-methylphenyl)amino]-quinoline-3-carbonitrile

Added 253 mg 10% palladium on carbon to a round bottom flask under $N_2$ and covered catalyst with 140 ml ethanol. To this added 2.49 g (8.18 mmol) 6-nitro-4-[(3-methylphenyl) amino]-quinoline-3-carbonitrile and 640 μl (20.4 mmol) anhydrous hydrazine. The mixture was heated to reflux for 2 hours 15 minutes and filtered hot through celite. Stripped solvent and dried in vacuo, giving 2.455 g of yellow solid: mass spectrum (electrospray m/e): M+H=275.2.

EXAMPLE 27

6-Nitro-4-[(3-methylphenyl)amino]-quinoline-3-carbonitrile

A mixture of 5.00 g (21.5 mmol) 4-chloro-6-nitro-quinoline-3-carbonitrile, 200 ml ethanol, and 2.75 ml (25.7 mmol) 3-toluidine was heated to reflux for 4½ hours. Cooled and added a saturated sodium bicarbonate until pH was basic. Stripped solvents and azeotroped with ethanol. Slurried with hexane, collected, and air dried. Washed with water and dried in vacuo. Boiled in ethyl acetate, stirred with Darco and filtered. Stripped solvent and dried in vacuo to give 4.82 g of yellow-orange solid: mass spectrum (electrospray m/e): M+H=305.2.

EXAMPLE 28

6-Amino-4-[(3-chlorophenyl)amino]-quinoline-3-carbonitrile

A mixture of 6.30 g (19.4 mmol) 4-[(3-chlorophenyl) amino]-6-nitro-quinoline-3-carbonitrile, 300 ml ethanol, and 21.9 g (97 mmol) $SnCl_2$ dihydrate were heated to reflux under $N_2$. Removed heat at 2½ hours, added ice water and made basic with sodium bicarbonate. Stirred for 2 hours and extracted with chloroform. Dried organic layer with sodium sulfate, filtered, stripped solvent and dried residue in vacuo, giving 5.74 g of yellow-brown solid: mass spectrum (electrospray m/e): M+H=295.1, 297.1.

EXAMPLE 29

4-[(3-Chlorophenyl)amino]-6-nitro-quinoline-3-carbonitrile

A mixture of 10.0 g (42.9 mmol)) 4-chloro-6-nitro-quinoline-3-carbonitrile, 260 ml ethanol, and 5.40 ml 3-chloroaniline was heated to reflux under $N_2$. Removed heat at 4 hours, cooled to 25° C. and added saturated sodium bicarbonate until the pH was basic. Stripped solvents and azeotroped with ethanol. Slurried residue with hexane, collected solid, and air dried. Washed solids with water and dried in vacuo. Dissolved in boiling ethyl acetate, stirred with Darco, and filtered. Stripped solvent and dried residue in vacuo, giving 6.5 g of yellow solid: mass spectrum (electrospray m/e): M+H=325.0, 327.0.

EXAMPLE 30

6-Amino-4-[(3-methoxyphenyl)amino]-quinoline-3-carbonitrile 325 mg of 10% palladium on carbon was added to a round bottom flask under $N_2$ and covered with 165 ml ethanol. Added 3.29 g (10.3 mmol) 4-[(3-methoxyphenyl)amino]-6-nitro-quinoline-3-carbonitrile and 800 μl anhydrous hydrazine and heated mixture to reflux. At 1½ hours, filtered hot through celite, stripped solvent and dried in vacuo, giving 2.876 g of yellow solid: mass spectrum (electrospray m/e): M+H=291.2.

EXAMPLE 31

4-[(3-Methoxyphenyl)amino]-6-nitro-quinoline-3-carbonitrile

A mixture of 5.00 g (21.5 mmol) 4-chloro-6-nitro-quinoline-3-carbonitrile, 200 ml ethanol, and 3.0 ml (26.0 mmol) m-anisidine was heated to reflux under $N_2$. Removed heat at 4½ hours and made basic with saturated sodium bicarbonate. Stripped solvents and azeotroped with ethanol. Slurried with hexane and collected crystals. Washed with water, dried in vacuo. Dissolved 5.94 g of crude product in 320 ml boiling ethyl acetate, stirred with Darco, filtered, stripped solvent, and dried in vacuo, giving about 5 g of yellow-orange solid: mass spectrum (electrospray m/e): M+H=291.1.

EXAMPLE 32

6-Amino-4-[(3-chloro-4-fluorophenyl)amino]-quinoline-3-carbonitrile

A mixture of 5.360 g (15.6 mmol) 4-[(3-chloro-4-fluorophenyl)amino]-6-nitro-quinoline-3-carbonitrile, 250 ml ethanol, and 17.67 g (78.2 mmol) $SnCl_2$ dihydrate was heated to reflux under $N_2$. Removed heat at 1½ hours and added ice water. Made basic with sodium bicarbonate. Stirred for 2 hours extracted with chloroform. Added brine to the separatory funnel to help separate layers. Stirred organic layer with Darco and dried with sodium sulfate. Filtered, stripped solvent and dried in vacuo, giving 4.460 g of yellow-brown solid: mass spectrum (electrospray m/e): M+H=312.9, 315.0.

EXAMPLE 33

4-[(3-Chloro-4-fluorophenyl)amino]-6-nitro-quinoline-3-carbonitrile

A mixture of 5.00 g (21.5 mmol) 4-chloro-6-nitro-quinoline-3-carbonitrile, 200 ml ethanol, and 3.75 g (25.8 mmol) 3-chloro-4-fluoroaniline was heated to reflux under $N_2$. Removed heat at 3½ hours and added a solution of saturated sodium bicarbonate until mixture was basic. Stripped solvents and azeotroped with ethanol. Slurried residue with hexane, collected solids, washed with water and dried in vacuo. Dissolved solids in 250 ml boiling ethyl acetate, stirred with Darco, and filtered. Stripped solvent and dried in vacuo, giving 6.036 g of yellow solid: mass spectrum (electrospray m/e): M+H=343.1, 345.1.

EXAMPLE 34

6-Amino-4-[(4-bromophenyl)amino]-quinoline-3-carbonitrile

A mixture of 3.10 g (8.40 mmol) 4-[(4-bromophenyl) amino]-6-nitro-quinoline-3-carbonitrile, 155 ml ethanol, and 9.47 g (42.0 mmol) $SnCl_2$ dehydrate was heated to reflux under $N_2$. After 4 hours, removed heat and added ice water. Made basic with sodium bicarbonate and stirred for 2 hours. With mixture still basic, extracted with chloroform, stirred organic layer with Darco and dried with sodium sulfate. Filtered, stripped solvent and dried in vacuo, giving 2.265 g of brown-yellow solid: mass spectrum (electrospray m/e): M+H=339.0, 341.0.

EXAMPLE 35

4-[(4-Bromophenyl)amino]-6-nitro-quinoline-3-carbonitrile

A mixture of 5.00 g (21.5 mmol) 4-chloro-6-nitro-quinoline-3-carbonitrile, 200 ml ethanol, and 4.42 g (25.8 mmol) p-bromoaniline was heated to reflux under $N_2$ for 3 hours. Removed heat and added saturated sodium bicarbonate until basic. Stripped solvents and azeotroped with ethanol. Slurried residue with hexane, collected solids, and air dried. Washed with water and dried in vacuo. Boiled in 1.4 liters ethyl acetate, and without completely dissolving all solids, stirred with Darco, and filtered. Stripped solvent and dried in vacuo, giving 3.524 g of yellow solid: mass spectrum (electrospray m/e): M+H=369, 370.9.

EXAMPLE 36

6-Amino-4-[(3.4-difluorophenyl)amino]-quinoline-3-carbonitrile

A mixture of 4.53 g (13.9 mmol) 4-[(3,4-difluorophenyl) amino]-6-nitro-quinoline-3-carbonitrile, 200 ml ethanol and 15.72 g (69.4 mmol) $SnCl_2$ dihydrate was heated to reflux under $N_2$. Removed heat at 1½ hours, added ice water and made basic with sodium bicarbonate. Stirred for 2 hours and extracted with chloroform. Stirred organic layer with Darco, dried with sodium sulfate and filtered. Stripped solvent and dried in vacuo, giving 3.660 g of yellow-green solid: mass spectrum (electrospray m/e): M+H=297.1.

EXAMPLE 37

4-[(3,4-Difluorophenyl)amino]-6-nitro-quinoline-3-carbonitrile

A mixture of 5.00 g (21.5 mmol) 4-chloro-6-nitro-quinoline-3-carbonitrile, 250 ml ethanol and 2.55 ml (25.8 mmol) 3,4-difluoroaniline was heated to reflux under $N_2$. Removed heat at 3½ hours and made basic with saturated sodium bicarbonate. Stripped solvents and azeotroped with ethanol. Slurried residue with hexane, collected solids and air dried. Washed with water and dried in vacuo. Dissolved in ethyl acetate, stirred with Darco, filtered, stripped solvent and dried in vacuo, giving 5.02 g of yellow solid: mass spectrum (electrospray m/e): M+H=327.1.

EXAMPLE 38

6-Amino-4-[(3-chloro-4-thiophenoxyphenyl)amino]-quinoline-3-carbonitrile

A mixture of 6.753 g (15.6 mmol) 4-[(3-chloro-4-thiophenoxyphenyl)amino]-6-nitro-quinoline-3-carbonitrile, 250 ml ethanol, and 17.66 g (78.0 mmol) $SnCl_2$ dihydrate was heated to reflux under $N_2$. Removed heat at 2 hours, added large volume of ice water, and made basic with sodium bicarbonate. Stirred for 2 hours and with mixture still basic, extracted with chloroform. Stirred organic layer with Darco, dried with sodium sulfate, filtered, stripped solvent and dried in vacuo, giving 5.996 g of yellow-brown solid: mass spectrum (electrospray m/e): M+H=403.1, 405.1.

EXAMPLE 39

4-[(3-Chloro-4-thiophenoxyphenyl)amino]-6-nitro-quinoline-3-carbonitrile

A mixture of 5.00 g (21.5 mmol) 4-chloro-6-nitro-quinoline-3-carbonitrile, 250 ml ethanol, and 6.07 g (25.6 mmol) 3-chloro-4-thiophenoxyaniline was heated to reflux under $N_2$. Removed heat at about 8 hours, made basic with saturated sodium bicarbonate, stripped solvents and azeotroped with ethanol. Slurried residue with hexane and collected solids. Washed with water and dried in vacuo. Dissolved nearly completely in 400 ml ethyl acetate, stirred with Darco and filtered. Stripped solvent and boiled in hexane to remove last of the excess aniline. Dried in vacuo, giving 6.90 g of red solid: mass spectrum (electrospray m/e): M+H=433.1, 435.1.

EXAMPLE 40

6-Amino-4-[(3-cyanophenyl)amino]-quinoline-3-carbonitrile

Added 100 mg of 10% palladium on carbon to a round bottom flask under $N_2$ and covered with 50 ml ethanol. Added 1.00 g (3.17 mmol) 4-[(3-cyanophenyl)amino]-6-nitro-quinoline-3-carbonitrile and 250 μl (7.39 mmol) anhydrous hydrazine and heated to reflux. Removed heat at 2 hours and filtered hot through celite. Stripped solvent and dried in vacuo, giving 887 mg of yellow solid: mass spectrum (electrospray m/e): M+H=286.2.

EXAMPLE 41

4-[(3-Cyanophenyl)amino]-6-nitro-quinoline-3-carbonitrile

A mixture of 5.00 g (21.5 mmol) 4-chloro-6-nitro-quinoline-3-carbonitrile, 200 ml ethanol, and 3.04 g (25.8 mmol) 3-aminobenzonitrile was heated to reflux. Removed heat at 3½ hours and made basic with saturated sodium bicarbonate. Stripped solvents and air dried. Slurried residue with hexane and collected solids. Washed with water and dried in vacuo. Boiled in large volume ethyl acetate, collected solids and dried in vacuo, giving 5.15 g of yellow-brown solid: mass spectrum (electrospray m/e): 316.0.

EXAMPLE 42

6-Amino-4-[(3-ethynylphenyl)amino)-quinoline-3-carbonitrile

A mixture of 2.00 g (6.36 mmol) 4-[(3-ethynylphenyl) amino]-6-nitro-quinoline-3-carbonitrile, 100 ml ethanol, and 7.19 g (31.8 mmol) $SnCl_2$ dihydrate was heated to reflux under $N_2$. Removed heat at 3½ hours and added ice water. Made basic with sodium bicarbonate and stirred for 2 hours. Extracted with chloroform, stirred organic layer with Darco, dried with sodium sulfate, filtered, stripped solvent, and dried in vacuo, giving 1.737 g of yellow-brown solid: mass spectrum (electrospray m/e): M+H=285.2.

EXAMPLE 43

4-[(3-Ethynylphenyl)amino]-6-nitro-quinoline-3-carbonitrile

A mixture of 5.00 g (21.5 mmol) 4-chloro-6-nitro-quinoline-3-carbonitrile, 200 ml ethanol, and 3.82 g (32.6 mmol) 3-ethynylaniline was heated to reflux under N2. Removed heat at 3½ hours and added a solution of saturated sodium bicarbonate until basic. Stripped solvents and azeotroped with ethanol. Slurried residue with hexane and collected solids. Washed with water and dried in vacuo. Dissolved in ethyl acetate, stirred with Darco, filtered, stripped solvent and dried in vacuo, giving 4.544 g of yellow solid: mass spectrum (electrospray m/e): M+H=315.1.

EXAMPLE 44

4-[(3-Bromo-4-fluorophenyl)amino]-6-nitro-quinoline-3-carbonitrile

A mixture of 3.8 g (16.33 mmol) of 4-chloro-6-nitro-quinoline-3-carbonitrile and 3.7 g (20 mmol) of 3-bromo-4-fluoroaniline in 200 mL of ethanol was refluxed for 3 hr. After the solvent was removed, the residue as dissolved in ethyl acetate and washed with sodium bicarbonate. The product was collected as a pale yellow solid, 6.5 g (71%); ESMS m/z 387.3, 389.2, mp 269-270° C. (dec).

EXAMPLE 45

6-Amino-4-[(3-Bromo-4-fluorophenyl)amino]-quinoline-3-carbonitrile

A mixture of 8 g (20.67 mmol) of 4-[(3-chloro-4-fluorophenyl)amino]-6-nitro-quinoline-3-carbonitrile, 4 g (72.35 mmol) of iron dust and 8.9 g (165.36 mmol) of ammonium chloride in 240 mL of methanol and water (2:1 ratio) was refluxed for 4 hr. The mixture was filtered hot and washed with methanol and water. The product precipitated from the filtrate upon cooling. The solid was collected and dried in vacuo to give 5.8 g (79%) yellowish brown solid; ESMS m/z 356.8, 358.8, mp 210-212° C.

EXAMPLE 46

4-(3-Chloro-4-fluoro-phenylamino)-7-methoxy-6-nitro-quinoline-3-carbonitrile

A mixture of 4.4 g (16.7 mmol) of 4-chloro-7-methoxy-6-nitro-quinoline-3-carbonitrile and 2.67 g (18.3 mmol) of 3-chloro-4-fluoro aniline in 110 ml of methoxyethanol was refluxed under nitrogen for 4 hours. The reaction mixture was diluted with ethyl acetate and wash with sodium bicarbonate solution and sodium chloride solution. The organic layer was dried over sodium sulfate and then the solvent was removed under vacuum. The residue was chromatographed on silica gel eluting with mixture of ethyl acetate and methanol to give 3 g yellow solid: mass spectrum (electrospray, m/e): 372.9.

EXAMPLE 47

6-Amino-4-(3-chloro-4-fluoro-phenylamino)-7-methoxy-quinoline-3-carbonitrile

A mixture of 4.88 g (13 mmol) of 4-[(3-chloro-4-fluorophenyl)amino]-7-methoxy-6-nitro-quinoline-3-carbonitrile, 5.2 g (97.5 mmol) of ammonium chloride, and 3.3 g (58.5 mmol) iron was stirred at reflux in 60 ml of water and 60 ml of methanol for 4.5 hours. The mixture was diluted with 500 ml of hot ethyl acetate and the hot mixture was filtered. The filtration was washed with saturated sodium chloride solution and then the organic layer was dried over sodium sulfate. The solvent was removed and the residue was chromatographed on silica gel eluting with mixture of ethyl acetate and methanol to give 3.38 g of yellow solid: mass spectrum (electrospray, m/e): M+H 343.4.

EXAMPLE 48

4-(3-Bromo-4-fluoro-phenylamino)-7-methoxy-6-nitro-quinoline-3-carbonitrile

A mixture of 3.52 g (9.7 mmol) of 4-chloro-7-methoxy-6-nitro-quinoline-3-carbonitrile and 2.0 g (10.7 mmol) of 3-bromo-4-fluoro aniline in 150 ml of methoxyethanol was refluxed under nitrogen for 5.5 hours. The reaction mixture was diluted with ethyl acetate and wash with sodium bicarbonate solution and sodium chloride solution. The organic layer was dried with sodium sulfate and then solvent was removed under vacuum. The residue was chromatographed on silica gel eluting with mixture of ethyl acetate and hexane to give the title compound.

EXAMPLE 49

6-Amino-4-(3-bromo-4-fluoro-phenylamino)-7-methoxy-quinoline-3-carbonitrile

A mixture o f 2.9 g (6.95 mmol) of 4-[(3-bromo-4-fluorophenyl)amino]7-methoxy-6-nitro-quinoline-3-carbonitrile, 6.5 g (121.6 mmol) of ammonium chloride and 4.05 g (73 mmol) of iron in 50 ml of water and 50 ml of methanol for 6 hours. The mixture was diluted with hot ethyl acetate and the hot mixture was filtered. The filtration was washed with saturated sodium chloride solution then the organic layer was dried over sodium sulfate. The solvent was removed and the residue was chromatographed on silica gel eluting with mixture of ethyl acetate and methanol to give 2.11 g of light yellow solid: mass spectrum (electrospray, m/e): M+H 386.7 and 388.8.

EXAMPLE 50

7-Ethoxy-4-hydroxy-quinoline-3-carbonitrile

A mixture of 10 g (73 mmol) of 3-ethoxy aniline and 12.3 g (73 mmol) of ethyl (ethoxymethylene) cyanoacetate was heated in 90 ml of Dowther at 140° C. for 7 hours. To this mixture was added 250 ml of Dowther. The solution was stirred and refluxed under nitrogen for 12 hours with periodically distilling out the eliminated ethanol. The mixture was cooled to room temperature and the solid was collected and washed with hexane. The crude solid was treated with boiling ethanol and then filtered to give 9.86 g of brown solid: mass spectrum (electrospray, m/e): M+H 214.7.

EXAMPLE 51

7-Ethoxy-4-hydroxy-6-nitro-quinoline-3-carbonitrile

To a suspension of 5 g (23 mmol) of 7-Ethoxy-4-hydroxy-quinoline-3-carbonitrile in 75 ml of trifluroacetic anhydride was added 5.5 g (69 mmol) of ammonium nitrate over a period of 6 hours at room temperature. Excess anhydride was removed at reduced pressure at 45° C. The residue was stirred with 300 ml of water. The solid was collected and treated with boiling ethanol to give 3.68 g of tin solid: mass spectrum (electrospray, m/e) M+H 259.8.

EXAMPLE 52

4-Chloro-7-ethoxy-6-nitro-quinoline-3-carbonitrile

A mixture of 3.45 g (13 mmol) of 7-Ethoxy-4-hydroxy-6-nitro-quinoline-3-carbonitrile, 5.55 g (26 mmol) of phosphorous pentachloride, and 10 ml of phosphorous oxychloride was refluxed for 3 hours. The mixture was diluted with hexane and the solid was collected. The solid was dissolved in 500 ml of ethyl acetate and washed with cold diluted sodium hydroxide solution. The solution was dried over magnesium sulfate and filtered through a pad of silica gel. The solvent was removed giving 2.1 g of beige solid: mass spectrum (electrospray, m/e) M+H 277.7.

EXAMPLE 53

4-(3-Bromo-phenylamino)-7-ethoxy-6-nitro-quinoline-3-carbonitrile

A mixture of 2.1 g (7.6 mmol) of 4-chloro-7-ethoxy-6-nitro-quinoline-3-carbonitrile and 0.91 ml (8.3 mmol) of 3-bromo aniline in 100 ml ethanol was refluxed under nitrogen for 4.5 hours. The reaction mixture was poured into diluted sodium bicarbonate solution. Ethanol was removed under vacuum. The mixture was diluted with ethyl acetate and the organic layer was separated and dried over sodium sulfate. The solution was concentrated and solid was collected and then washed with hexane. Upon drying, 2.6 g of yellow solid obtained: mass spectrum (electrospray, m/e) M+H 412.8 and 414.9.

EXAMPLE 54

6-Amino-4-(3-bromo-phenylamino)-7-ethoxy-quinoline-3-carbonitrile

A mixture of 2.5 g (6 mmol) of 4-[(3-bromophenyl) amino]-7-ethoxy-6-nitro-quinolinec-3-carbonitrile, 2.4 g (45 mmol) of ammonium chloride, and 1.5 g (27 mmol) iron was stirred at reflux in 40 ml of water and 40 ml of methanol for 4 hours. The mixture was diluted with 500 ml of hot ethyl acetate and the hot mixture was filtered. The filtration was washed with saturated sodium chloride solution and then the organic layer was dried over sodium sulfate. The solution was concentrated and 1.5 of beige solid was collected: mass spectrum (electrospray, m/e): M+H 382.8 and 384.8.

EXAMPLE 55

8-Methoxy-4-hydroxy-6-nitro-quinoline-3-carbonitrile

A mixture of 12.6 g (75 mmol) of 2-methoxy-4-nitro aniline and 12.7 g (75 mmol) of ethyl (ethoxymethylene) cyanoacetate was heated in 100 ml of Dowther at 120° C. for overnight and 180° C. for 20 hours. To this mixture was added 300 ml of Dowther. The solution was stirred and refluxed under nitrogen for 12 hours with periodically distilling out the eliminated ethanol. The mixture was cooled to room temperature and the solid was collected and washed with hexane. The crude solid was treated with boiling ethanol and then filtered to give 12 g of brown solid: mass spectrum (electrospray, m/e): M+H 245.8.

EXAMPLE 56

4-Chloro-8-methoxy-6-nitro-quinoline-3-carbonitrile

A mixture of 4 g (16 mmol) of 8-Methoxy-4-hydroxy-6-nitro-quinoline-3-carbonitrile, 6.66 g (32 mmol) of phosphorous pentachloride, and 15 ml of phosphorous oxychloride was refluxed for 2.5 hours. The mixture was diluted with hexane and the solid was collected. The solid was dissolved in 500 ml of ethyl acetate and washed with cold diluted sodium hydroxide solution. The solution was dried over magnesium sulfate and filtered through a pad of silica gel. The solvent was removed giving 2.05 g of tan solid: mass spectrum (electrospray, m/e) M+H 263.7.

EXAMPLE 57

6-Nitro-4-(3-bromo-phenylamino)-8-methoxy-quinoline-3-carbonitrile

A mixture of 1.9 g (7.6 mmol) of 4-chloro-8-methoxy-6-nitro-quinoline-3-carbonitrile and 0.86 ml (8.3 mmol) of 3-bromo aniline in 95 ml ethanol was refluxed under nitrogen for 5 hours. The reaction mixture was poured into diluted sodium bicarbonate solution. Ethanol was removed under vacuum. The mixture was diluted with ethyl acetate and the organic layer was separated and dried over sodium chloride. The solution was concentrated and solid was collected and then washed with hexane. Upon drying, 2.3 g of yellow solid obtained: mass spectrum (electrospray, m/e) M+H 398.8 and 400.8.

EXAMPLE 58

6-Amino-4-(3-bromo-phenylamino)-8-methoxy-quinoline-3-carbonitrile

A mixture of 2.15 g (5 mmol) of 4-[(3-bromophenyl) amino]-8-methoxy-6-nitro-quinoline-3-carbonitrile, 1.95 g (37.5 mmol) of ammonium chloride, and 1.26 g (22.5 mmol) iron was stirred at reflux in 40 ml of water and 40 ml of methanol for 3 hours. The mixture was diluted with 500 ml of hot ethyl acetate and the hot mixture was filtered. The filtration was washed with saturated sodium chloride solution and then the organic layer was dried over sodium sulfate. The solution was concentrated and 0.43 of dark yellow solid was collected: mass spectrum (electrospray, m/e): M+H 368.9 and 370.9.

EXAMPLE 59

4-Chloro-but-2-yanoic Acid

Propargyl chloride (2 mL, 26.84 mmol) was dissolved in 40 mL of tetrahydrofuran under nitrogen and cooled to -78° C. After addition of n-butyllithium (5.4 mL, 13.42 mmol, 2.5 M in n-hexane) and stirred for 15 min, a stream of dry carbon dioxide was passed through it at −78° C. for two hours. The reaction solution was filtered and neutralized with 3.5 mL of 10% sulfuric acid. After evaporation of the solution, the residue was extracted with ether. The ether solution was washed with saturated brine solution, and dried over sodium sulfate. After evaporation of the dry ether solution, 0.957 g (60%) of an oil product was obtained: ESMS m/z 116.6 ($M-H^+$).

EXAMPLE 60

4-Dimethylamino-but-2-ynoic Acid n-Butyl lithium in hexane (96 mL, 2.5 M in n-hexane) was slowly added to 1-dimethylamino-2-propyne (20 g, 240 mmol) in 100 mL of tetrahydrofuran under nitrogen. The mixture was stirred for 1 h at −78° C., then dry carbon dioxide was pass through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 15.6 g of 4-dimethylamino-but-2-ynoic acid: mass spectrum (m/e): M−H 126.

EXAMPLE 61

Bis-(2-methoxy-ethyl)-prop-2-ynyl-amine

Propargyl bromide (17.8 g, 150 mmol) was added dropwise to a mixture of bis(2-methoxy-ethyl)amine (20 g, 150 mmol) and cesium carbonate (49 g, 150 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 20 g of bis-(2-methoxy-ethyl)-prop-2-ynyl-amine: mass spectrum (m/e): M+H 172.

EXAMPLE 62

4-[Bis-(2-methoxy-ethyl)-amino]-but-2-ynoic Acid n-Butyl lithium in hexane (42 mL, 2.5M in n-hexane) was slowly added to bis-(2-methoxy-ethyl)-prop-2-ynyl-amine (18 g, 105 mmol) in 80 mL of tetrahydrofuran under nitrogen. The mixture was stirred for 1 h at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 18 g of 4-[bis-(2-methoxy-ethyl)-amino]-but-2-ynoic acid: mass spectrum (m/e): M−H 214.

EXAMPLE 63

1-Methyl-4-prop-2-ynyl-piperazine

Propargyl bromide (23.8 g, 200 mmol) was added dropwise to a mixture of 1-methyl-piperazine (20 g, 200 mmol) and cesium carbonate (65 g, 200 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 7.5 g of 1-methyl-4-prop-2-ynyl-piperazine: mass spectrum (m/e): M+H 139.

EXAMPLE 64

4-(4-Methyl-piperazin-1-yl)-but-2-ynoic Acid n-Butyl lithium in hexane (17.2 mL, 2.5M in n-hexane) was slowly added to 1-methyl-4-prop-2-ynyl-piperazine (6.0 g, 43.5 mmol) in 40 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 7 g of 4-(4-methyl-piperazin-1-yl)-but-2-ynoic acid: mass spectrum (m/e): M−H 181.

EXAMPLE 65

(2-Methoxy-ethyl)-methyl-prop-2-ynyl-amine

Propargyl bromide (26.8 g, 225 mmol) was added dropwise to a mixture of N-(2-methoxyethyl)methyl amine (20 g, 225 mmol) and cesium carbonate (73 g, 225 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 14 g of (2-methoxy-ethyl)-methyl-prop-2-ynyl-amine: mass spectrum (m/e): M+H 127.

EXAMPLE 66

4-[(2-Methoxy-ethyl)-methyl-amino]-but-2-ynoic Acid n-Butyl lithium in hexane (37.8 mL, 2.5 M in n-hexane) was slowly added to (2-methoxy-ethyl)-methyl-prop-2-ynyl-amine (12.0 g, 94.5 mmol) in 90 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 15 g of 4-[(2-methoxy-ethyl)-methyl-amino]-but-2-ynoic acid: mass spectrum (m/e): M−H 170.

EXAMPLE 67

Allyl-methyl-prop-2-ynyl-amine

Propargyl bromide (33.4 g, 281 mmol) was added dropwise to a mixture of isopropyl-methyl-amine (20 g, 281 mmol) and cesium carbonate (90 g, 281 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 4.6 g of allyl-methyl-prop-2-ynyl-amine: mass spectrum (m/e): M+H 110.

EXAMPLE 68

4-(Allyl-methyl-amino)-but-2-ynoic Acid n-Butyl lithium in hexane (16.4 mL, 2.5M in n-hexane) was slowly added to allyl-methyl-prop-2-ynyl-amine (4.5 g, 46 mmol) in 50 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 4.1 g of 4-(allyl-methyl-amino)-but-2-ynoic acid: mass spectrum (m/e): M−H 152.

EXAMPLE 69

4-Methoxymethoxy-but-2-ynoic Acid

To a suspension of 8.2 g of 60% sodium hydride in mineral oil in 271 mL of tetrahydrofuran at 0° C. with stirring under nitrogen was added dropwise 10 g of propargyl alcohol over 15 min. The mixture was stirred an additional 30 min. To the stirred mixture at 0° C. was added 15.8 g of chloromethylmethyl ether. Stirring was continued at room temperature over night. The mixture was filtered and the solvent was removed from the filtrate. The residue was distilled (35-38° C., 4 mm) giving 8.5 g of a liquid. The distillate was dissolved in 200 mL of ether. The solution was stirred under nitrogen and cooled to −78° C. as 34.1 mL of 2.5 molar n-butyl lithium in hexanes was added over 15 min. Stirring was continued for another 1.5 hr. Dry carbon dioxide was allowed to pass over the surface of the stirring reaction mixture as it warmed from −78° C. to room temperature. The mixture was stirred under a carbon dioxide atmosphere over night. The mixture was poured into a mixture of 14 mL of hydrochloric acid and 24 mL of water. The organic layer was separated and dried over magnesium sulfate. The solvent was removed and the residue was maintained at 100° C. at 4 mm for 1 hr giving 10.4 g 4-Methoxymethoxy-but-2-ynoic acid.

EXAMPLE 70

4-Bromo Crotonic Acid

After the method of Braun [Giza Braun, J. Am. Chem. Soc. 52, 3167 (1930)], 11.76 mL (17.9 grams 0.1 moles) of methyl 4-bromo crotonate in 32 mL of ethanol and 93 mL of water was cooled to −11° C. The reaction was stirred vigorously, and 15.77 g (0.05 moles) of finely powdered barium hydroxide was added portionwise over a period of about an hour. Cooling and vigorous stirring were continued for about 16 hours. The reaction mixture was then extracted with 100 mL of ether. The aqueous layer was treated with 2.67 mL (4.91 g; 0.05 moles) of concentrated sulfuric acid. The resulting mixture was extracted with 3-100 mL portions of ether. The combined ethereal extracts were washed with 50 mL of brine, then dried over sodium sulfate. The solution was taken to an oil in vacuo. This oil was taken up in about 400 mL of boiling heptane, leaving a gum. The heptane solution was separated and boiled down to about 50 mL. Cooling gave 3.46 g of product.

EXAMPLE 71

4-(2-Methoxy-ethoxy)-but-2-ynoic Acid

To a suspension of 6.04 g (151 mmol) of 60% sodium hydride in 200 ml of tetrahydrofuran at 0° C. was add 10 g (131.4 mmol) of 2-methoxyethanol dropwise over 15 min. After 1 hr, 19.54 g (131.4 mmol) of 80% propargyl bromide was added dropwise. After stirring 17 hr at room temperature, the mixture was filtered and the solvent was remove. The residue was distilled (48-51° C., 4 mm) to give 11.4 g of a colorless liquid. This was dissolved in 250 ml of ether and cooled to −78° C. with stirring under nitrogen. To this solution was added 39.95 ml (99.9 mmol) of 2.5M n-butyl lithium solution in hexanes dropwise over 15 min. After 1.5 hr, dry carbon dioxide was bubbled in as the mixture slowly warmed to room temperature. The mixture was maintained in a carbon dioxide atmosphere overnight. To the mixture was added 100 ml of 3N hydrochloric acid and solid sodium chloride. The organic layer was separated and dried over magnesium sulfate. The solvent was removed and the residue was maintained under vacuum giving 11.4 g of the title compound.: mass spectrum (electrospray, m/e, negative mode): M−H 156.8.

EXAMPLE 72

4-(2-Methoxy-ethoxy)-but-2-ynoic Acid[4-(3-bromo-phenylamino)-3-cyano-quinolin-6-yl]-amide To a solution of 0.56 g (3.54 mmol) of 4-(2-methoxy-ethoxy)-but-2-ynoic acid and 0.46 g (3.4 mmol) of isobutyl chloroformate in 12 ml of tetrahydrofuran was added at 0° C. with stirring 0.36 g (3.54 mmol) of N-methylmorpholine. After 15 min, 1.0 g (2.95 mmol) of 6-amino-4-[(3-bromophenyl)amino]-quinoline-3-carbonitrile was added. After stirring 3 hr at 0° C. and 17 hr at room temperature, the mixture was poured into a saturated solution of sodium bicarbonate. The mixture was extracted with ethyl acetate and the organic layer was dries over magnesium sulfate. The solvent was remove and the residue was purified by chromatography on silica gel eluting with chloroform-ethyl acetate mixtures to give 0.53 g of 4-(2-Methoxy-ethoxy)-but-2-ynoic acid[4-(3-bromo-phenylamino)-3-cyano-quinolin-6-yl]-amide as a yellow powder: mass spectrum (electrospray, m/e,): M+H 480.9.

EXAMPLE 73

4-(Methoxymethoxy)-but-2-ynoic Acid

To a suspension of 8.2 g (205 mmol) of 60% sodium hydride in 271 ml of tetrahydrofuran was added dropwise at 0° C. with stirring 10.0 g (178.4 mmol) of propargyl alcohol. After 30 min, 15.8 g (196.2 mmol) of chloromethylmethyl ether was added. After stirring over the weekend at room temperature, the mixture was filtered and the solvent was remove. The residue was distilled (35-38° C., 4 mm) to give 8.54 g of a colorless liquid. This was dissolved in 200 ml of ether and cooled to −78° C. with stirring under nitrogen. To this solution was added 34.1 ml (85.3 mmol) of 2.5M n-butyl lithium solution in hexanes dropwise over 15 min. After 1.5 hr, dry carbon dioxide was bubbled in as the mixture slowly warmed to room temperature. The mixture was maintained in a carbon dioxide atmosphere overnight. To the mixture was added 14 ml of hydrochloric acid in 24 ml water. The organic layer was separated and dried over magnesium sulfate. The solvent was removed and the residue was maintained under vacuum giving 10.4 g of the title compound as a liquid.

EXAMPLE 74

4-Methoxymethoxy-but-2-ynoic Acid[4-(3-bromo-phenylamino)-3-cyano-quinolin-6-yl]-amide To a solution of 0.51 g (3.54 mmol) of 4-(methoxymethoxy)-but-2-ynoic acid and 0.46 g (3.4 mmol) of isobutyl chloroformate in 12 ml of tetrahydrofuran was added at 0° C. with stirring 0.36 g (3.54 mmol) of N-methylmorpholine. After 15 min, 1.0 g (2.95 mmol) of 6-amino-4-[(3-bromophenyl)amino]-quinoline-3-carbonitrile was added. After stirring 3 hr at room temperature, the mixture was poured into a saturated solution of sodium bicarbonate. The mixture was extracted with ethyl acetate and the organic layer was dries over magnesium sulfate. The solvent was remove and the residue was purified by chromatography on silica gel eluting with chloroform-ethyl acetate mixtures to give 0.66 g of 4-methoxymethoxy-but-2-ynoic acid[4-(3-bromophenylamino)-3-cyano-quinolin-6-yl]-amide as a yellow powder: ma of 6-amino-4-[(3-bromophenyl)amino]-quinoline-3-carbonitrile: mass spectrum (electrospray, m/e,): M+H 465.1, 467.0.

EXAMPLE 75

N-[4-[(3-Bromophenyl)amino]-3-cyano-6-quinolinyl]-4-(bis-(2-methoxyethyl)amino)-2-butynamide Isobutyl chloroformate (0.785 g, 5.75 mmol) was dropwise added into an ice cold solution of 4-(bis-methoxyethylamino)-2-butynoic acid (1.9 g, 8.85 mmol) and N-methylmorpholine (0.9386 g, 9.28 mmol) in 50 mL of tetrahydrofuan under $N_2$. After stirring for 30 min, a solution of 1.5 g (4.42 mmol) of 6-amino-4-[(3-bromophenyl)amino]-quinoline-3-carbonitrile in 10 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 0.82 (35%) of light brown solid; ESMS m/z 536.1, 538.1 ($M+H^+$); mp 98-101° C.

EXAMPLE 76

N-[4-[(3-Bromophenyl)amino]-3-cyano-6-quinolinyl]-4-(N-methoxyethyl-N-methylamino)-2-butynamide Isobutyl chloroformate (0.785 g, 5.75 mmol) was dropwise added into an ice cold solution of 4-(N-methoxyethyl-N-methylamino)-2-butynoic acid (1.5 g, 8.84 mmol) and N-methylmorpholine (1.36 g, 13.3 mmol) in 60 mL of tetrahydrofuan under $N_2$. After stirring for 30 min, a solution of 1.5 g (4.42 mmol) of 6-amino-4-[(3-bromophenyl)amino]-quinoline-3-carbonitrile in 15 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 0.32 (15%) of reddish brown solid; ESMS m/z 492.0, 494.0 ($M+H^+$); mp 95° C. (dec).

EXAMPLE 77

N-[4-[(3-Bromophenyl)amino]-3-cyano-6-quinolinyl]-4-(N-allyl-N-methylamino)-2-butynamide Isobutyl chloroformate (0.785 g, 5.75 mmol) was dropwise added into an ice cold solution of 4-(N-allyl-N-methylamino)-2-butynoic acid (1.4 g, 8.84 mmol) and N-methylmorpholine (0.94 g, 9.3 mmol) in 80 mL of tetrahydrofuan under $N_2$. After stirring for 30 min, a solution of 1.5 g (4.42 mmol) of 6-amino-4-[(3-bromophenyl)amino]-quinoline-3-carbonitrile in 15 mL of pyridine was added dropwise and the mixture was stirred at 0° C. for 2 hr. The reaction was quenched with ice water, poured into saturated sodium bicarbonate anid brine, and extracted with ethyl acetate. The ethyl acetate layer was concentrated and purified by flash column chromatography. The product fractions were collected, and dried in vacuo to give 0.60 (29%) of brown solid; ESMS m/z 474.4, 476.4 ($M+H^+$); mp 133-135° C.

EXAMPLE 78

1-Methyl-1,2,5,6-tetrahydro-pyridine-3-carboxylic Acid[4-(3-bromo-phenylamino)-3-cyano-quinolin-6-yl]-amide To a solution of 1 g (2.95 mmol) of 6-amino-4-[(3-bromophenyl)amino]-quinoline-3-carbonitrile and 1.9 g (14.7 mmol) of dissopropylethylamine was strirred in 19 ml of tetrahydrofuran and solid N-methyl-1,2,5,6-tetrahydronicotinyl chloride hydrochloride was added portionwise at 0° C. After stirring 1 hr at 0° C. and 2 hr at room temperature, the mixture was poured into saturated sodium bicarbonate and extracted with ethylacetate. The solution was dried over magnesium sulfate. Sovent was removed and the residue was recrystalized from methanol-ethylacetate giving 0.92 g of a yellow powder: mass spectrum (electrospray, m/e,): M+H 462.4, 464.4.

EXAMPLE 79

4-((2S)-2-Methoxymethylpyrrolidin-1-yl)but-2-ynoic Acid[4-(3-bromophenylamino)-3-cyanoquinolin-6-yl]amide To an ice cold solution of 1.46 g (7.40 mmol) of 4-((2S)-2-methoxymethylpyrrolidin-1-yl)but-2-ynoic acid in 85 mL of THF under $N_2$ was added 0.897 g (8.88 mmol) of N-methylmorpholine and 0.811 g (5.92 mmol) of isobutyl chloroformate. After stirring in the cold for 30 min, a solution of 1.00 g (2.96 mmol) of 6-amino-4-[(3-bromophenyl)amino]-quinoline-3-carbonitrile in 8 mL of pyridine was added dropwise. The reaction was slowly warmed to 25° C. over 3 h. The reaction was poured into ice water, satd $NaHCO_3$ was added and the product was extracted with ethyl acetate. After drying and solvent evaporation, the residue was chromatographed on silica gel (10% methanol in ethyl acetate). The yield was 0.560 g of 4-((2S)-2-methoxymethylpyrrolidinyl-1-yl)but-2-ynoic acid [4-(3-bromophenylamino)-3-cyanoquinolin-6-yl] amide as a brown foam: mass spectrum (electrospray, m/e): M+H 518.0, 520.0.

EXAMPLE 80

4-((2S)-2-Methoxymethylpyrrolidin-1-yl)butynoic Acid n-Butyllithium solution in hexane (35.9 mmol) was added over 10 min to a solution of 5.49 g (35.9 mmol) of (2S)-2-methoxymethyl-1-prop-2-ynylpyrrolidine in 100 mL of THF at −78° C. under $N_2$. After stirring cold for 1 h, $CO_2$ was bubbled into the solution as it slowly came to 25° C. After stirring overnight, 100 mL of water was added, the reaction was extracted with ethyl acetate and the extracts were discarded. The reaction was adjusted to pH 7 with 20% $H_2SO_4$ and solvent was removed. The residue was slurried with methanol and filtered. The filtrate was evaporated and dried in vacuo to give 7.06 g of 4-((2S)-2-methoxymethylpyrrolidin-1-yl)butynoic acid as a brown foam: mass spectrum (electrospray, m/e): M+H 198.0.

EXAMPLE 81

(2S)-2-Methoxymethyl-l-prop-2-ynylpyrrolidine

A mixture of 4.82 g (41.9 mmol) of S-2-(methoxymethyl) pyrrolidine, 13.7 g (41.9 mmol) of cesium carbonate and 5.00 g (41.9 mmol) of propargyl bromide in 80 mL of acetone was stirred at 25° C. overnight. The reaction was filtered and solvent was removed from the filtrate. The residue was diluted with a small amount of water and satd $NaHCO_3$ and extracted with ether. The extract was treated with Darco, dried and evaporated to give 5.93 g of (2S)-2-methoxymethyl-1-prop-2-ynylpyrrolidine as a yellow orange oil: mass spectrum (electrospray, m/e): 153.8.

EXAMPLE 82

4-(1,4-Dioxa-8-azaspiro[4,5]dec-8-yl)but-2-ynoic Acid[4-(3-Bromophenylamino)-3-cyanoquinolin-6-yl]amide To an ice cold solution of 1.75 g (7.78 mmol) of 4-(1,4-dioxa-8-azaspiro[4,5]dec-8-yl)but-2-ynoic acid in 100 mL of THF under $N_2$ was added 0.942 g (9.33 mmol) of N-methylmorpholine followed by 0.852 g (6.22 mmol) of isobutyl chloroformate. After stirring in the cold for 30 min, a solution of 1.05 g (3.11 mmol) of 6-amino-4-[(3-bromophenyl) amino]-quinoline-3-carbonitrile in 8 mL of pyridine was added dropwise. After stirring in the cold for 5 h, the reaction was poured into ice water and satd $NaHCO_3$ was added. The mixture was extracted with ethyl acetate and the extracts were dried and evaporated. Chromatography of the residue on silica gel (20% methanol in ethyl acetate) gave 0.590 g of 4-(1,4-dioxa-8-azaspiro[4,5]dec-8-yl)but-2-ynoic acid[4-(3-bromophenylamino)-3-cyanoquinol-6-yl]amide as a brown foam: mass spectrum (electrospray, m/e): M+H 546.0, 548.1.

EXAMPLE 83

4-(1,4-Dioxa-8-azaspiro[4,5]dec-8-yl)but-2-ynoic Acid n-Butyllithium in hexane (55.8 mmol) was added dropwise to a solution of 10.1 g (55.8 mmol) of 3-(1,4-dioxa-8-azaspiro [4,5]dec-8-yl)but-2-yne in 185 mL of THF at −78° C. under $N_2$. After stirring at −78° C. for 1 h, $CO_2$ was bubbled into the solution as it slowly came to 25° C. After stirring overnight, the reaction was diluted with 150 mL of water, extracted with ethyl acetate and the extracts were discarded. The solution was adjusted to pH 6 with 2 M sulfuric acid and evaporated. The residue was slurried with methanol and filtered. The filtrate was evaporated and dried in vacuo to give 4.5 g of 4-(1,4-dioxa-8-azaspiro[4,5]dec-8-yl)but-2-ynoic acid as a brown amorphous solid: mass spectrum electrospray, m/e): M+H 225.8.

EXAMPLE 84

3-(1,4-Dioxa-8-azaspiro[4,5]dec-8-yl)but-2-yne

A mixture of 10.0 g (69.9 mmol) of 1,4-dioxa-8-azaspiro [4,5]decane, 22.8 g (69.9 mmol) of cesium carbonate and 8.32 g (69.9 mmol) of propargyl bromide in 165 mL of acetone was stirred overnight at 25° C. The reaction was filtered and the filtrate was evaporated to dryness. A small amount of water and satd $NAHCO_3$ was added to the residue and it was extracted with ether. The ethereal extracts were treated with Darco, dried and evaporated to give 10.8 g of 3-(1,4-dioxa-8-azaspiro[4,5]dec-8-yl)but-2-yne as a yellow orange oil: mass spectrum (electrospray, m/e): M+H 181.8.

EXAMPLE 85

4-(3-Bromo-phenylamino)-6-(2-ethoxy-3,4-dioxo-cyclobut-1-enylamino)-quinoline-3-carbonitrile A mixture of 1.00 g (2.95 mmol) 6-amino-4-(3-chloro-phenylamino)-quinoline-3-carbonitrile, 20 mL ethanol, and 0.873 mL (5.90 mmol) 3,4-diethoxy-3-cyclobutene-1,2-dione was heated to reflux under N2. At 4 hours removed heat, cooled to 25° C. and stirred overnight. Decanted off solution and stripped solvent. Added ether to crystallize, collected solids and dried. Boiled in ethyl acetate to remove cyclobutene starting material. Dried in vacuo, giving 249 mg of yellow solid: mass spectrum (electrospray m/e): M+H=463.2.

EXAMPLE 86

4-(4-Chloro-2-fluoro-phenylamino)-6,7-dimethoxy-quinoline-3-carbonitrile

A mixture of 2.0 g of 4-chloro-6,7-dimethoxy-quinoline-3-carbonitrile, 1.46 g of 4-chloro-2-fluoroaniline, 0.925 g of pyridine hydrochloride, and 125 ml of ethoxyethanol was stirred under nitrogen, at reflux temperature for 1 h. The mixture was cooled and added to 1000 ml of water. To this mixture was added sodium carbonate to pH 9. The product was collected, washed with water, and dried to give 2.61 g of 4-(4-chloro-2-fluoro-phenylamino)-6,7-dimethoxy-quinoline-3-carbonitrile as a solid, mp 139-141° C.; mass spectrum (electrospray, m/e): M+H 357.9.

EXAMPLE 87

4-(4-Chloro-2-fluoro-phenylamino)-6,7-dihydroxy-quinoline-3-carbonitrile

A mixture of 0.358 g of 4-(4-chloro-2-fluoro-phenylamino)-6,7-dimethoxy-quinoline-3-carbonitrile and 3 g of pyridine hydrochloride was stirred under nitrogen at 210-220° C. for 20 minutes. The mixture was cooled and added to 50 ml of 3% ammonium hydroxide solution. The product was collected, washed with water, and dried to give 0.302 g of 4-(4-chloro-2-fluoro-phenylamino)-6,7-dihydroxy-quinoline-3-carbonitrile as a solid, mp 270-272° C.; mass spectrum (EI, m/e): M 329.0363.

EXAMPLE 88

4-(4-Chloro-2-fluoro-phenylamino)-6-methoxy-7-(2-pyridin-4-yl-ethoxy)-quinoline-3-carbonitrile To a solution of 0.655 g of triphenylphosphine in 20 ml of tetrahydrofuran was added dropwise 0.348 mg of diethyl azodicarboxylate. The solution was stirred for one minute and added to a mixture of 0.330 g of 4-(4-chloro-2-fluoro-phenylamino)-6,7-dihydroxy-quinoline-3-carbonitrile and 0.500 g of 2-(4-pyridyl)ethanol in 100 ml of tetrahydrofuran. The mixture was stirred at room temperature for 4 hours, and 10 ml of methanol was added.

To a solution of 0.655 g of triphenylphosphine in 20 ml of tetrahydrofuran was added dropwise 0.348 mg of diethyl azodicarboxylate. The solution was stirred for one minute and added to the above mixture. The mixture was stirred overnight and concentrated in vacuo. The residue was chromatographed on silica gel eluting with 5% methanol in dichloromethane. Solvent was removed from product fractions giving 0.034 g of 4-(4-Chloro-2-fluoro-phenylamino)-6-methoxy-7-(2-pyridin-4-yl-ethoxy)-quinoline-3-carbonitrile as a white wax: mass spectrum (EI, m/e): M 448.1104. The regiochemistry was assigned unequivocally by NMR analysis (Proton, DQF-COSY, NOESY, $\{^{1}H-^{13}C\}$-HMQC, $\{^{1}H-^{13}C\}$-HMBC, $\{^{1}H-^{15}N\}$-HMBC.

EXAMPLE 89

4-[(2-Methoxy-ethyl)-methyl-amino]-but-2-enoic Acid[4-(3-chloro-4-fluoro-phenylamino)-3-cyano-7-methoxy-quinolin-6-$_{yl}$]-amide Dihydrochloride To a stirring solution of 1.2 g (3.5 mmol) of 6-amino-4-(3-chloro-4-fluoro-phenylamino)-7-methoxy-quinoline-3-carbonitrile and 0.52 g (4.0 mmol) of diisopropylethylamine in 40 ml of tetrahydrofuran at 0° C. was added a solution of 4-bromo crotonyl chloride in 10 ml of tetrahydrofuran. After 45 min, 1.87 (21 mmol) of 2-methoxyethyl methyl amine was added. After 1 hr at room temperature, the mixture was poured into a solution of sodium bicarbonate and extracted with ethyl acetate. The organic solution was dried over magnesium sulfate. The solvent was removed and the residue was purified by chromatography on silica gel. Product eluted with ethyl acetate-methanol-triethylamine 40:8:1 giving 0.87 g of the free base. This was dissolved in 20 ml of ethyl acetate and 10 ml of a solution of hydrogen chloride in ether was added. The solid was collected giving 1.02 g of the title compound as a yellow powder: mass spectrum (electrospray, m/e): M+H 498.0, $(M+2H)^{+2}$248.5.

EXAMPLE 90

(S)-4-(2-Methoxymethyl-pyrrolidin-1-yl)-but-2-enoic Acid[4-(3-chloro-4-fluoro-phenylamino)-3-cyano-7-methoxy-quinolin-6-yl]-amide dihydrochloride By using the method of Example 89, 1.2 g (3.5 mmol) of 6-amino-4-(3-chloro-4-fluoro-phenylamino)-7-methoxy-quinoline-3-carbonitrile and 2.4 g (21 mmol) of (S)-(+)-2-(methoxymethy) pyrrolidine were converted to 1.5 g the title compound, obtained as a yellow powder: mass spectrum (electrospray, m/e): M+H 524.0, $(M+2H)^{+2}$ 262.4. This reaction can also be done with (R)-(−)-2-(methoxymethy) pyrrolidine or racemic 2-(methoxymethy) pyrrolidine giving the R-entaniomer or the racemate, respectively.

EXAMPLE 91

4-(3-Hydroxymethyl-piperidin-1-yl)-but-2-enoic Acid[4-(3-chloro-4-fluoro-phenylamino)-3-cyano-7-methoxy-quinolin-6-yl]-amide Hydrochloride By using the method of Example 89, 1.1 g (3.2 mmol) of 6-amino-4-(3-chloro-4-fluoro-phenylamino)-7-methoxy-quinoline-3-carbonitrile and 2.2 g (19.2 mmol) of 3-hydroxymethyl-piperidine were converted to 0.76 g the title compound, obtained as a yellow powder: mass spectrum (electrospray, m/e): M+H 524.0, $(M+2H)^{+2}$262.3.

EXAMPLE 92

4-(1,4-Dioxa-8-aza-spiro[4.5]dec-8-yl)-but-2-enoic Acid[4-(3-chloro-4-fluoro-phenylamino)-3-cyano-7-methoxy-quinolin-6-yl]-amide By using the method of Example 89, 1.05 g (3.06 mmol) of 6-amino-4-(3-chloro-4-fluoro-phenylamino)-7-methoxy-quinoline-3-carbonitrile and 2.6 g (18.4 mmol) of 1,4-dioxa-8-azaspiro[4.5]decane were converted to 0.62 g the title compound. The free base obtained as a yellow foam: mass spectrum (electrospray, m/e): M+H 552.0, $(M+2H)^{+2}$270.5.

EXAMPLE 93

4-(2-Hydroxymethyl-piperidin-1-yl)-but-2-enoic Acid[4-(3-chloro-4-fluoro-phenylamino)-3-cyano-7-methoxy-quinolin-6-yl]-amide By using the method of Example 89, 1.05 g (3.06 mmol) of 6-amino-4-(3-chloro-4-fluoro-phenylamino)-7-methoxy-quinoline-3-carbonitrile and 2.1 g (18.4 mmol) of 2-hydroxymethyl-piperidine were converted to 0.67 g the title compound. The free base was obtained as an off-white powder: mass spectrum (electrospray, m/e): M+H 524.3, $(M+2H)^{+2}$267.7.

EXAMPLE 94

4-Bromo-but-2-enoic Acid[4-(3-chloro-4-fluoro-phenylamino)-3-cyano-7-methoxy-quinolin-6-yl]-amide By using the method of Example 15, 4-bromo crotonyl chloride and 6-amino-4-(3-chloro-4-fluoro-phenylamino)-7-methoxy-quinoline-3-carbonitrile was converted to the title compound which was obtained as a solid that could be purified with boiling methanol.

EXAMPLE 95

3-{3-[4-(3-Chloro-4-fluoro-phenylamino)-3-cyano-7-methoxy-quinolin-6-ylcarbamoyl]-allyl}-5-methyl-thiazol-3-ium Bromide A solution of 0.5 g (1 mmol) of 4-bromo-but-2-enoic acid [4-(3-chloro-4-fluoro-phenylamino)-3-cyano-7-methoxy-quinolin-6-yl]-amide and 0.6 g (6.1 mmol) of 5-methyl thiazole was refluxed for 4 hr. The mixture was diluted with ethyl acetate and cooled. Solid was collected and recrystallized from methanol-acetone-ethyl acetate to give 0.2 g of the title compound as a yellow powder: mass spectrum (electrospray, m/e): $M^+$508.0, 509.9, $(M+H)^+_2$254.4, 255.1.

EXAMPLE 96

3-{3-[4-(3-Chloro-4-fluoro-phenylamino)-3-cyano-7-methoxy-quinolin-6-ylcarbamoyl]-allyl}-4-methyl-thiazol-3-ium Bromide A solution of 0.7 g (1.4 mmol) of 4-bromo-but-2-enoic acid[4-(3-chloro-4-fluoro-phenylamino)-3-cyano-7-methoxy-quinolin-6-yl]-amide and 0.85 g (8.6 mmol) of 4-methyl thiazole was refluxed for 17 hr. The mixture was diluted with ethyl acetate and cooled. Solid was collected and recrystallized from methanol-acetone-ethyl acetate to give 0.3 g of the title compound as a yellow powder: mass spectrum (electrospray, m/e): $M^+$507.9, 509.8, $(M_+H)^+_2$2254.4, 255.1.

EXAMPLE 97

Methyl 4-benzyloxy-2-(dimethylaminomethylene-amino)-5-methoxybenzoate

A stirred mixture of 70.0 g (244 mmol) of methyl 2-amino-4-benzyloxy-5-methoxybenzoate (Phytochemistry 1976, 15, 1095) and 52 ml of dimethylformamide dimethyl acetal was heated at 100° C. for 1.5 h, cooled, and evaporated directly under high vacuum to give 81.3 g of off-white solid, mp 134-140° C.; NMR ($CDCl_3$) d 3.01 (s, $Me_2N$).

EXAMPLE 98

7-Benzyloxy-4-hydroxy-6-methoxy-quinoline-3-carbonitrile

To a stirred solution of 26.9 ml of n-butyllithium (2.5 M in hexane) in 50 ml of THF at −78° C. was added a 3.51 ml of acetonitrile in 20 ml of THF during 10 min. After stirring at −78° C. for 30 min, the mixture was treated with 10 g of methyl 4-benzyloxy-2-(dimethylaminomethyleneamino)-5-methoxybenzoate in 20 ml of THF during 5 min. After 15 min at −78° C. the stirred mixture was warmed to 0° C. for a further 30 min. It was then treated with 5 ml of acetic acid, warmed to 25° C. and stirred for 30 min. The mixture was evaporated to dryness, and diluted with aqueous sodium bicarbonate. The resulting off-white solid was filtered, washed with water, ethyl acetate and ether. After drying, 4.5 g of 7-benzyloxy-4-hydroxy-6-methoxy-quinoline-3-carbonitrile was obtained as an off-white solid, dec >255° C.; mass spectrum (electrospray, m/e) M+H 307.

EXAMPLE 99

7-Benzyloxy-4-chloro-6-methoxy-quinoline-3-carbonitrile

To a stirred suspension of 1 g of 7-benzyloxy-4-hydroxy-6-methoxy-quinoline-3-carbonitrile in 10 ml of methylene chloride was added 5 ml of oxalyl chloride (2M in methylene chloride), and 2 drops of N,N-dimethylformamide. The mixture was refluxed for 20 min and to it was slowly added aqueous sodium bicarbonate until the bubbling ceased. Following separation of the layers, the organic layer was evaporated to a small volume, then passed through a plug of magnesol. Elution with 50 ml methylene chloride, followed by evaporation provided 0.6 g of 7-benzyloxy-4-chloro-6-methoxy-quinoline-3-carbonitrile as a pale yellow solid, mp 282-284° C.; mass spectrum (electrospray, m/e) M+H 325.

EXAMPLE 100

4-Chloro-7-hydroxy-6-methoxy-quinoline-3-carbonitrile

A stirred suspension of 0.54 g of 7-benzyloxy-4-chloro-6-methoxy-quinoline-3-carbonitrile in 10 ml of methylene chloride was cooled to 0° C. To this was added 10 ml of boron trichloride (1M in methylene chloride). The mixture darkened as it warmed to room temperature and a solid precipitated out. After stirring for 1 hour, no further reaction was observed. The solid (unreacted starting material) was filtered off, the remaining solution was cooled to 0° C. and quenched by the dropwise addition of methanol. Following evaporation of the solvent, the residue was dissolved in methylene chloride/methanol/acetone. Purification of this residue was carried out using silica gel chromatography, eluting with a solvent gradient of 1 to 5 percent methanol/methylene chloride, to provide 0.075 g of 4-chloro-7-hydroxy-6-methoxy-quinoline-3-carbonitrile as a yellow solid, dec >245° C.; mass spectrum (electrospray, m/e) M+H 235.2.

EXAMPLE 101

4-Chloro-6-methoxy-7-(3-pyridin-4-yl-propoxy)-quinoline-3-carbonitrile

A mixture of 0.070 g of 4-chloro-7-hydroxy-6-methoxy-quinoline-3-carbonitrile, 0.062 g of 3-(4-pyridyl)-1-propanol and 0.235 g of triphenylphosphine in 3 ml of methylene chloride under nitrogen was cooled to 0° C. To this was added 0.14 ml of diethyl azodicarboxylate dropwise. After 30 minutes, the reaction mixture was warmed to room temperature and further stirred for 2 hours. The mixture was concentrated down to 1 ml and purified by silica gel chromatography, eluting with a solvent gradient of 1 to 2 percent methanol/methylene chloride, to provide 0.090 g of 4-chloro-6-methoxy-7-(3-pyridin-4-yl-propoxy)-quinoline-3-carbonitrile as an off-white gum.

EXAMPLE 102

4-(3-Hydroxy-4-methyl-phenylamino)-6-methoxy-7-(3-pyridin-4-yl-propoxy)-quinoline-3-carbonitrile A mixture of 0.090 g of 4-chloro-6-methoxy-7-(3-pyridin-4-yl-propoxy)-quinoline-3-carbonitrile, 0.050 g of 3-hydroxy-4-methylaniline, 0.039 g of pyridine hydrochloride and 3 ml of ethoxyethanol was stirred under nitrogen at reflux temperature for 20 minutes. The mixture was cooled and filtered. The product was washed with saturated sodium bicarbonate, water, then dried to give 0.080 g of 4-(3-hydroxy-4-methyl-phenylamino)-6-methoxy-7-(3-pyridin-4-yl-propoxy)-quinoline-3-carbonitrile hydrochloride as a solid, dec >153° C.; mass spectrum (electrospray, m/e): M+H 440.9.

EXAMPLE 103

4-Diallylamino-but-2-enoic Acid[4-(3-chloro-4-fluoro-phenylamino)-3-cyano-7-methoxy-quinolin-6-yl]-amide A solution of 0.24 g (0.5 mmol) of 4-bromo-but-2-enoic acid[4-(3-chloro-4-fluoro-phenylamino)-3-cyano-7-methoxy-quinolin-6-yl]-amide in 1 ml of N,N-dimethylformamide and 4 ml of tetrahydrofuran was stirred with 0.49 ml (4 mmol) of diallylamine for 3 hr. The reaction was quenched with 10 ml of saturated sodium bicarbonate and 10 ml of ethyl acetate. The insoluble precipitate was collected and washed with water to give 23.7 mg of the title compound (free base); mass spectrum (electrospray, m/e): M+H 506.0. The ethyl acetate layer was washed with water. After the solvent was removed, the crude product was purified by preparative HPLC (C18 column, Gradient from 2% acetonitrile containing 0.05% trifluoroacetic acid to 100% acetonitrile containing 0.05% trifluoroacetic acid in 12 min) to yield 97.9 mg of the product as the bis-trifluoroacetate salt; mass spectrum (electrospray, m/e): M+H 506.0.

EXAMPLE 104

4-[Bis-(2-methoxy-ethyl)-amino]-but-2-enoic Acid [4-(3-chloro-4-fluoro-phenylamino)-3-cyano-7-methoxy-quinolin-6-yl]-amide In the mamner of Example 103, 4-bromo-but-2-enoic acid [4-(3-chloro-4-fluoro-phenylamino)-3-cyano-7-methoxy-quinolin-6-yl]-amide and bis-(2-methoxy-ethyl)-amine was converted to 52.3 mg of the title compound as the bis-trifluoroacetate salt mass spectrum (electrospray, m/e): M+H 542.0.

EXAMPLE 105

4-([1,3]Dioxolan-2-ylmethyl-methyl-amino)-but-2-enoic Acid3-cyano-7-methoxy-quinolin-6-yl]-amide In the mamner of Example 103, 4-bromo-but-2-enoic acid [4-(3-chloro-4-fluoro-phenylamino)-3-cyano-7-methoxy-quinolin-6-yl]-amide and [1,3]dioxolan-2-ylmethyl-methylamine was converted to 116.2 mg of the title compound as the bis-trifluoroacetate salt); mass spectrum (electrospray, m/e): M+H 526.0.

EXAMPLE 106

4-[Bis-(2-hydroxy-ethyl)-amino]-but-2-enoic Acid [4-(3-chloro-4-fluoro-phenylamino)-3-cyano-7-methoxy-quinolin-6-yl]-amide In the mamner of Example 103, 4-bromo-but-2-enoic acid [4-(3-chloro-4-fluoro-phenylamino)-3-cyano-7-methoxy-quinolin-6-yl]-amide and bis-(2-hydroxy-ethyl) amine was converted to 22.2 mg of the title compound (free base), mass spectrum (electrospray, m/e): M+H 514.0 and 60.7 mg of the title compound as the bis-trifluoroacetate salt); mass spectrum (electrospray, m/e): M+H 514.0.

EXAMPLE 107

4-Thiomorpholin-4-yl-but-2-enoic Acid[4-(3-chloro-4-fluoro-phenylamino)-3-cyano-7-methoxy-quinolin-6-yl]-amide In the mamner of Example 103, 4-bromo-but-2-enoic acid [4-(3-chloro-4-fluoro-phenylamino)-3-cyano-7-methoxy-quinolin-6-yl]-amide and thiomorpholine was converted to 48.1 mg of the title compound (free base), mass spectrum (electrospray, m/e): M+H 512.0 and 33.2 mg of the title compound as the bis-trifluoroacetate salt); mass spectrum (electrospray, m/e): M+H 512.0.

EXAMPLE 108

4-[4-(2-Hydroxy-ethyl)-piperazin-1-yl]-but-2-enoic Acid[4-(3-chloro-4-fluoro-phenylamino)-3-cyano-7-methoxy-quinolin-6-yl]-amide In the mamner of Example 103, 4-bromo-but-2-enoic acid [4-(3-chloro-4-fluoro-phenylamino)-3-cyano-7-methoxy-quinolin-6-yl]-amide and 4-(2-hydroxy-ethyl) piperazine was converted to 32.3 mg of the title compound (free base) and mass spectrum (electrospray, m/e): M+H 539.1, 42.2 mg of the title compound as the bis-trifluoroacetate salt); mass spectrum (electrospray, m/e): M+H 539.1.

EXAMPLE 109

4-(1,4,7-Trioxa-10-aza-cyclododec-10-yl)-but-2-enoic Acid[4-(3-chloro-4-fluoro-phenylamino)-3-cyano-7-methoxy-quinolin-6-yl]-amide In the mamner of Example 103, 4-bromo-but-2-enoic acid [4-(3-chloro-4-fluoro-phenylamino)-3-cyano-7-methoxy-quinolin-6-yl]-amide and 1,4,7-trioxa-10-aza cyclododecane was converted to 37.5 mg of the title compound(free base) and mass spectrum (electrospray, m/e): M+H 584.1, 17.1 mg of the title compound as the bis-trifluoroacetate salt); mass spectrum (electrospray, m/e): M+H 584.1.

EXAMPLE 110

4-(Methoxy-methyl-amino)-but-2-enoic Acid[4-(3-chloro-4-fluoro-phenylamino)-3-cyano-7-methoxy-quinolin-6-yl]-amide A mixture of 1 g of the 4-bromo-but-2-enoic acid[4-(3-chloro-4-fluoro-phenylamino)-3-cyano-7-methoxy-quinolin-6-yl]-amide (2.04 mmol, 1 equiv.), 1.2 g of N,O-Dimethylhydroxylamine hydrochloride (12.25 mmol, 9 equiv.), and 1.5 g of sodium bicarbonate (18.38 mmol, 9 equiv.) in DMF (10 ml) was stirred at room temperature for 24 hours. Ethyl acetate was added to the reaction mixture, and the crude product was filtered. After flash chromatography (ethyl acetate:methanol:triethylamine 40:4:1), 0.486 g of the title compound was isolated (50.7% yield); mp 210-217° C.

EXAMPLE 111

4-(4-Hydroxy-piperidin-1-yl)-but-2-enoic Acid[4-(3-chloro-4-fluoro-phenylamino)-3-cyano-7-methoxy-quinolin-6-yl]-amide A mixture of 250 mg (0.51 mmol) of the 4-bromo-but-2-enoic acid[4-(3-chloro-4-fluoro-phenylamino)-3-cyano-7-methoxy-quinolin-6-yl]-amide, and 103.2 mg (1.02 mmol) of 4-hydroxypiperidine in 2.25 ml dimethylformamide was stirred at room temperature for 3 hr. Saturated sodium bicarbonate was added and the precipitate was filtered and washed with hexane to give the first crop of product. The filtrate was extracted with ethyl acetate and the organic layer with purified by preparative TLC to yield the second crop. The two crops were combined to give 105.8 mg (41%) tan solid: mp >215° C.

EXAMPLE 112

4-[1,4']Bipiperidinyl-1'-yl-but-2-enoic Acid[4-(3-chloro-4-fluoro-phenylamino)-3-cyano-7-methoxy-quinolin-6-yl]-amide A mixture of 250 mg (0.51 mmol) of 4-bromo-but-2-enoic acid[4-(3-chloro-4-fluoro-phenylamino)-3-cyano-7-methoxy-quinolin-6-yl]-amide, and 172 mg (1.02 mmol) of 4-piperidinopiperidine in 5.0 ml dimethylformamide was stirred at room temperature for 4 hr and at 60° C. for 1 hr. After the mixture was cooled, the suspension was diluted with saturated sodium bicarbonate solution and extracted with ethyl acetate. The extracts were evaporated to an oil and purified by preparative TLC to yield 100 mg (40%) yellow solid: mp 140-144° C.

EXAMPLE 113

4-Thiazolidin-3-yl-but-2-enoic Acid[4-(3-chloro-4-fluoro-phenylamino)-3-cyano-7-methoxy-quinolin-6-yl]-amide A mixture of 250 mg (0.51 mmol) of 4-bromo-but-2-enoic acid[4-(3-chloro-4-fluoro-phenylamino)-3-cyano-7-methoxy-quinolin-6-yl]-amide, and 80 μL (1.02 mmol) of thiazolidine in 2.25 ml dimethylformamide was stirred at room temperature for 19.5 hr. After the mixture was cooled, the suspension was diluted with saturated sodium bicarbonate solution and extracted with ethyl acetate. The extracts were evaporated to an oil and purified by preparative TLC to yield 95.6 mg (38%) yellow solid: mp 135-138° C.

EXAMPLE 114

4-(2,6-Dimethyl-piperidin-1-yl)-but-2-enoic Acid[4-(3-chloro-4-fluoro-phenylamino)-3-cyano-7-methoxy-quinolin-6-yl]-amide A mixture of 250 mg (0.51 mmol) of 4-bromo-but-2-enoic acid[4-(3-chloro-4-fluoro-phenylamino)-3-cyano-7-methoxy-quinolin-6-yl]-amide, and 137 μL (1.02 mmol) of cis-2,6-dimethylpiperidine in 2.25 ml dimethylformamide was stirred at room temperature for 3 hr. The reaction mixture was diluted with saturated sodium bicarbonate solution and extracted with ethyl acetate. The extracts were evaporated to an oil, washed with hexane and dried under reduced pressure to yield 170.4 mg (64%) tan solid: mp 120-122° C.

EXAMPLE 115

4-[Bis-(2-hydroxy-propyl)-amino]-but-2-enoic Acid [4-(3-chloro-4-fluoro-phenylamino)-3-cyano-7-methoxy-quinolin-6-yl ]-amide A mixture of 250 mg (0.51 mmol) of 4-bromo-but-2-enoic acid[4-(3-chloro-4-fluoro-phenylamino)-3-cyano-7-methoxy-quinolin-6-yl]-amide, and 136 mg (1.02 mmol) of 1,1'-iminodi-2-propanol in 2.25 ml dimethylformamide was stirred at room temperature for 3 hr and at 60° C. for 2 hr. After the mixture was cooled, saturated sodium bicarbonate solution was added and the solution was subsequently extracted with ethyl acetate. The extracts were evaporated to an oil, washed with hexane and dried under reduced pressure. Yield 240.1 mg (87%) tan solid: mp 122-125° C.

EXAMPLE 116

4-(3-Hydroxy-pyrrolidin-1-yl)-but-2-enoic Acid[4-(3-chloro-4-fluoro-phenylamino)-3-cyano-7-methoxy-quinolin-6-yl]-amide A mixture of 250 mg (0.51 mmol) of 4-bromo-but-2-enoic acid[4-(3-chloro-4-fluoro-phenylamino)-3-cyano-7-methoxy-quinolin-6-yl]-amide, and 85 μL (1.02 mmol) of R-(+)-3-pyrrolidinol in 5.0 ml dimethylformamide was stirred at room temperature for 4 hr and at 60° C. for 1 hr. After the mixture was cooled, saturated sodium bicarbonate solution was added and the solution was subsequently extracted with ethyl acetate. The extracts were evaporated to an oil, and purified by preparative TLC. Yield 84.2 mg (33%) yellow solid: mp 215-220° C.

EXAMPLE 117

4-[(2-Hydroxy-ethyl)-methyl-amino]-but-2-enoic Acid[4-(3-chloro-4-fluoro-phenylamino)-3-cyano-7-methoxy-quinolin-6-yl]-amide 4-bromo-but-2-enoic acid[4-(3-chloro-4-fluoro-phenylamino)-3-cyano-7-methoxy-quinolin-6-yl]-amide (250 mg, 0.51 mmol.) and 2-(methylamino)-ethanol(97 mg, 1.02 mmol.) were dissolved with stirring, under nitrogen, in 9 ml anhydrous dimethylformamide. After 48 hours, the mixture was partitioned between saturated sodium bicarbonate solution, and ethyl acetate. The organic phase was seperated, dried over magnesium sulfate, filtered, and evaporated to give a gum. It was chromatographed on silica gel, and eluted with 40/4/1 (ethyl acetate/methanol/triethylamine) producing 183 mg (74%) of the purified product as a yellow solid: mp 210-214° C.

EXAMPLE 118

4-(2,5-Dimethyl-pyrrolidin-1-yl)-but-2-enoic Acid [4-(3-chloro-4-fluoro-phenylamino)-3-cyano-7-methoxy-quinolin-6-yl]-amide In the same manner as Example 117, 4-bromo-but-2-enoic acid[4-(3-chloro-4-fluoro-phenylamino)-3-cyano-7-methoxy-quinolin-6-yl]-amide. (0.51 mmol.) was reacted with 2,5-dimethylpyrrolidine (1.02 mmol., 101 mg.) in dimethylformamide. The crude product was also purified via chromatography as Example 117, leaving 214 mg. (82%) of the yellow product: mp 110-113° C.

EXAMPLE 119

4-(4,4-Dihydroxy-piperidin-l-yl)-but-2-enoic Acid [4-(3-chloro-4-fluoro-phenylamino)-3-cyano-7-methoxy-quinolin-6-yl]-amide After the procedure of Example 117, 4-bromo-but-2-enoic acid[4-(3-chloro-4-fluoro-phenylamino)-3-cyano-7-methoxy-quinolin-6-yl]-amide. (0.51 mmol.) was stirred in dimethylformamide with 4-piperidone monohydrate hydrochloride (470 mg., 3.06 mmol.), and sodium bicarbonate (386 mg., 4.59 mmol.), for 24 hours. The crude product was purified in the same manner as Example 117 and produced 192 mg. (72%) of the product as a yellow solid: mp 225-30° C.

EXAMPLE 120

6-(4-Chlorobutylamino)-4-(3-chloro-4-fluorophenyamino)-7-methoxy-3-quinolinecarbonitrile To a solution of 1.12 g of 4-chlorobutanal and 5.3 ml of 3M sulfuric acid in 11 ml of tetrahydrofuran, at 0° C., was added an solution of 2.0 g of 6-amino-4-(3-chloro-4-fluoro-phenylamino)-7-methoxy-3-quinolinecarbonitrile in 40 ml of dimethylforamide. To this was added portionwise 0.4 g of sodium borohydride. After 1 hr another 1.0 g of aldehyde, 10 ml of dimethylforamide, and 5 ml of 3M sulfuric acid was added followed by the portionwise addition of 0.8 g of sodium borohydride. After 2 hrs, the mixture was poured into water and the Ph was adjusted to 9. The mixture was extracted with ethyl acetate several times. The organic solution was dried over magnesium sulfate and the solvent was removed giving the title compound as an oil which was used without additional purification.

EXAMPLE 121

4-(3-Chloro-4-fluoro-phenylamino)-7-methoxy-6-(4-morpholin-4-yl-butylamino)-quinoline-3-carbonitrile

EXAMPLE 122

4-(3-Chloro-4-fluoro-phenylamino)-7-methoxy-6-pyrrolidin-1-yl-quinoline-3-carbonitrile A mixture of 2.5 g of 6-(4-chlorobutylamino)-4-(3-chloro-4-fluorophenyamino)-7-methoxy-3-quinolinecarbonitrile, 7.54 g of morpholine, and 0.17 g of sodium iodide in 30 ml of dimethylformamide was stirred at 750° C. for 7 hrs. The mixture was poured into dilute sodium bicarbonate and solid was collected. This material was dissolved in ethylacetate. The solution was dried over magnesium sulfate. The solvent was removed and the residue was chromatographed on silica gel using ethyl acetate-methanol-triethylamine mixtures. A more polar component (0.54 g) was 4-(3-chloro-4-fluorophenylamino)-7-methoxy-6-(4-morpholin-4-yl-butylamino)-quinoline-3-carbonitrile; a less polar component (0.28 g) is the compound of this invention, 4-(3-chloro-4-fluoro-phenylamino)-7-methoxy-6-pyrrolidin-l-yl-quinoline-3-carbonitrile, obtained as a yellow solid: mass spectrum electrospray, m/e): M+H 397.4.

EXAMPLE 123

4-(3-Chloro-4-fluroanilino)-7-methoxy-6-(1H-pyrrol-1-yl)-3-quinolinecarbonitrile A dimethylformamide (4.5 ml) suspension of 6-amino-4-[(3-chloro-4-fluoroanilino)-7-methoxy-3-quinolinecarbonitrile (0.2 g, 0.5839 mmol), 2,5-dimethoxytetrahydrofuran (0.1 ml, 0.77 mmol) and 4-chloropyridinium chloride (0.05 g, 0.333 mmol) was heated at 108° C. overnight. The reaction solution was mixed with saturated sodium bicarbonated solution, brine and ethyl acetate. The ethyl acetate layer was separated, filtered through silica gel, and dried up to give 119 mg of 4-(3-Chloro-4-fluroanilino)-7-methoxy-6-(1H-pyrrol-1-yl)-3-quinolinecarbonitrile as a cream-colored solid, mp 192.5-193.5° C.: high resolution mass spectrometry (electrospray, m/e): M+H 393.0913.

EXAMPLE 124

6-[(2-chloroethyl)amino]-4-(3-chloro-4-fluoroanilino)-7-methoxy-3-quinolinecarbonitrile To a solution of 1 g of 6-amino-4-[(3-chloro-4-fluoroanilino)-7-methoxy-3-quinolinecarbonitrile (2.92 mmol) in 20 ml of dimethylformamide at 0° C., was added a solution of 50% aqueous chloroformaldehyde (0.75 ml, 5.84 mmol) and 3 M sulfuric acid (2.92 ml, 8.76 mmol) in 5.3 ml of tetrahydrofuran, followed by portionwise addition of 1.1 g of sodium borohydride powder (29.68 mmol). After the reaction mixture was stirred overnight at room temperature, the precipitated product was collected and partitioned between ethyl acetate and 10 N sodium hydroxide solution. The organic layer was washed with brine and dried over sodium sulfate. The solvent was removed to yield 0.7648 g of a yellow solid. After recrystallization from acetonitrile, 0.5831 g of bright needle crystals were obtained; mp 207.2-207.8° C.; high resolution mass spectrometry (EI, m/e): 404.060. The filtrate was treated with 10 N sodium hydroxide and ethyl acetate, and worked up as above to afford additional 0.38 g of crude product.

EXAMPLE 125

6-(1-Aziridinyl)-4-(3-chloro-4-fluoroanilino)-7-methoxy-3-quinolinecarbonitrile

To a solution of 0.202 g (0.5 mmol) of 6-[(2-chloroethyl) amino]-4-(3-chloro-4-fluoroanilino)-7-methoxy-3-quinolinecarbonitrile in 4 ml of dimethylformamide, were added 0.075 g of sodium iodide (0.5 mmol) and 0.069 g of potassium carbonate (0.5 mmol). After the reaction solution was heated at 75° C. overnight, it was decanted into cold saturated sodium bicarbonate solution. The organic layer was separated and dried over sodium sulfate. The solvent was removed to yield 0.19 g of a light brown solid. The crude product was washed with hexane to give 0.1 g of a yellow solid, mp 197-199° C.; high resolution mass spectrometry (EI, m/e): M 368.0888.

EXAMPLE 126

1-(Dimethylaminomethyleneamino)-3-chlorobenzene

A mixture of 3-chloroaniline (63.8 g, 0.50 mol) and dimethylformamide dimethyl acetal (106 ml, 0.75 mol) was heated at 100° for 2 h and evaporated at 60° at 0.5 mm Hg to give 91.8 g amber oil; ms 183.0 $(M+H)^+$.

EXAMPLE 127

1-(Dimethylaminomethyleneamino)-3-chloro-4-nitrobenzene

To a stirred solution of 1-(dimethylaminomethyleneamino)-3-chlorobenzene (67.5 g, 0.37 mol) in 148 ml of gl HOAc was added 70% nitric acid (70 ml, 1.11 mol) during 15 m with cooling at 10° . To the resulting solution was added $Ac_2O$ (222 ml, 2.58 mol) during 30 m with cooling to maintain 15-20° . The solution was heated to 65° during 20 m. The resulting exothermic reaction was moderated with cool water at 65-68° for 45 m and then the reaction was heated at 65° for 90 m. The reaction mixture was cooled to 10°, stirred with DCM, and quenched with ice and 10 N NaOH (850 ml). The organic layer was separated, washed thoroughly with water, dried, filtered through Magnesol, and concentrated to give 62.2 g red gummy solid. Flash chromatography of the residue on silica gel with 20:4:1 DCM-EtOAc-MeOH gave an amber solid, mp 78-90°; ms 228.1 $(M+H)^+$.

EXAMPLE 128

(E/Z)-2-Cyano-3-(3-chloro-4-nitrophenylamino) acrylic Acid, Ethyl Ester

To a stirred mixture of 1-(dimethylaminomethylene-amino)-3-chloro-4-nitrobenzene (7.9 g, 35 mmol) and 17.4 ml of HOAc at 250 was added ethyl cyanoacetate (5.2 g, 46 mmol). The resulting mixture was refluxed for 1.5 h, cooled, and stirred in water for 45 m. The resulting amber solid was filtered off, washed with water followed by 5:1 hexane-EtOAc, and dried; mp 195-205°; ms 294.1 (M−H).

EXAMPLE 129

1,4-Dihydroquinoline-7-chloro-6-nitro-4-oxo-3-carbonitrile

A stirred mixture of (E/Z)-2-cyano-3-(3-chloro-4-nitrophenylamino)acrylic acid, ethyl ester (2.36 g, 8.0 mmol) and 240 ml of Dowtherm A was heated at 260° C. for 2 h, cooled, diluted with hexane, and filtered. The tan solid thus obtained was digested with boiling EtOAc, filtered, and dried to give 1.47 g, mp 320-330° (dec); ms 248.1 $(M-H)^-$.

EXAMPLE 130

4,7-Dichloro-6-nitro-3-quinolinecarbonitrile

A stirred mixture of 1,4-dihydroquinoline-7-chloro-6-nitro-4-oxo-3-carbonitrile (14.7 g, 58.9 mmol) and 59 ml of phosphorous oxychloride was refluxed for 3 h. The phosphorous oxychloride was removed in vacuo, and the residue was stirred with methylene chloride at 0° C. and treated with a slurry of ice and potassium carbonate. The mixture was filtered through Celite, and the organic layer of the filtrate was separated, washed with water, dried, and concentrated to give 10.7 g of tan solid. Recrystallization from hexane-DCM gave mp 143-153°; ms 266.7 $(M-H)^-$.

EXAMPLE 131

4-(3-Chloro-4-fluoroanilino)-7-chloro-6-nitro-3-quinolinecarbonitrile

A stirred mixture of 4,7-dichloro-6-nitro-3-quinolinecarbonitrile (10.7 g, 40 mmol), 3-chloro-4-fluoroaniline (7.0 g, 48 mmol), pyridine hydrochloride (4.6 g, 40 mmol), and 200 ml of 2-propanol was heated to reflux temperature and maintained for 1 h. The 2-propanol was evaporated off, and the residue was stirred in water with potassium bicarbonate (pH~8). The resulting solid was filtered, washed with water and 5:1 hexane-DCM, and dried. Recrystallization from EtOH gave 11.3 g of yellow solid, mp 259-263°; ms 377.1 $(M+H)^+$.

EXAMPLE 132

4-(3-Chloro-4-fluoroanilino)-7-(4-methyl-1-piperazinyl)-6-nitro-3-quinolinecarbonitrile A stirred mixture of 4-(3-chloro-4-fluoroanilino)-7-chloro-6-nitro-3-quinolinecarbonitrile (1.88 g, 5.0 mmol), N-methylpiperazine (5 ml, 45 mmol), and 10 ml of toluene was refluxed for 45 m, evaporated to remove volatile matter, and stirred in water with potassium carbonate (2.75 g). The resulting solid was filtered, washed with water, and dried to give 2.26 g. An acetone solution was passed onto a pad of silica gel; elution with 50:2:1 acetone-MeOH-TEA and evaporation gave a red solid, mp 240-246°; ms 441.2 $(M+H)^+$, 221.2 $(M+2H)^{+2}$.

EXAMPLE 133

6-Amino-4-(3-chloro-4-fluroanilino)-7-(4-methyl-1-piperazinyl)-3-quinolinecarbonitrile In the manner of Example 23 4-(3-chloro-4-fluoroanilino)-7-(4-methyl-1-piperazinyl)-6-nitro-3-quinolinecarbonitrile was reduced with iron powder and acetic acid in MeOH to give the title compound as an amorphous solid; ms 411.2 $(M+H)^+$, 206.2 $(M+2H)^{+2}$.

EXAMPLE 134

N-[4-(3-Chloro-4-fluoroanilino)-3-cyano-7-(4-methyl-1-piperazinyl)-6-quinolinyl]-2-butynamide To a stirred solution of 2-butynoic acid (0.25 g, 3.0 mmol) in 1.5 ml of DCM at 0° was added DCC (0.21 g, 1.0 mmol). After 15 m the mixture was warmed to 25°, recooled to 0°, and treated with 6-amino-4-(3-chloro-4-fluroanilino)-7-(4-methyl-1-piperazinyl)-3-quinolinecarbonitrile (0.21 g, 0.50 mmol) followed by 0.5 ml DCM rinse. The resulting mixture was stirred at 25° for 18 h and filtered to remove dicyclohexyl urea. The filtrate was partitioned with water which contained potassium carbonate (0.4 g, 3 mmol). The organic layer was washed with water, dried, and concentrated. The residue was passed as a solution in DCM onto a pad of silica gel. The product was eluted with 50:2:1 acetone-MeOH-TEA and concentrated to give 0.165 g amorphous solid; ms 477.2 $(M+H)^+$, 239.1 $(M+2H)^{+2}$.

EXAMPLE 135

3-Chloro-N-[4-(3-chloro-4-fluoroanilino)-3-cyano-7-(4-morpholinyl)-6-quinolinyl]propanamide To a stirred solution of 3-chloropropionic acid (0.65 g, 6.0 mmol)in 3 ml of DCM at 0° was added DCC (0.41 g, 2.0 mmol). After 15 m the mixture was warmed to 25°, recooled to 0°, and treated with 6-amino-4-(3-chloro-4-fluroanilino)-7-(4-morpholinyl)-3-quinolinecarbonitrile (0.40 g, 1.0 mmol) followed by 1 ml DCM rinse. The resulting mixture was stirred at 25° for 20 h, diluted with DCM, and stirred with aqueous sodium bicarbonate. The mixture was filtered to remove dicyclohexyl urea. The organic layer of the filtrate was washed with water, dried, and concentrated. The residue was passed as a solution in DCM onto a pad of silica gel. The product was eluted with 25:25:2:1 DCM-EtOAc-MeOH-TEA and concentrated to give 0.38 g amorphous solid; ms 488.1$(M+H)^+$.

EXAMPLE 136

N-[4-(3-Chloro-4-fluoroanilino)-3-cyano-7-(4-morpholinyl)-6-quinolinyl]acrylamide To a stirred solution of 3-chloro-N-[4-(3-chloro-4-fluoroanilino)-3-cyano-7-(4-morpholinyl)-6-quinolinyl]propanamide (0.30 g, 0.61 mmol) in 1.2 ml of THF at 0° was added 1.2 ml of 1.0 M KOtBu/tBuOH dropwise during 1 m. After 2 h at 0° the reaction was quenched with solid $CO_2$ and partitioned with DCM-water. The organic layer was washed with water, dried, and evaporated to give 0.28 g of the title compound as a white amorphous solid; ms 452.2 $(M+H)^+$.

By using the methods described in Examples 1-136 above and the methods described in the patent applications WO-9843960 and WO-9909016, the compounds of this invention listed in Table 6 were prepared.

TABLE 6

| Example | Compound | m.p. (° C.) | mass spectrum |
|---|---|---|---|
| 137 | 4-[(2-Methoxy-ethyl)-methyl-amino]-but-2-enoic acid [4-(3-bromo-phenylamino)-3-cyano-7-ethoxy-quinolin-6-yl]-amide | amorphous | 538.0 (M + H) |
| 138 | 4-(2,4-Dichloro-5-methoxy-phenylamino)-7-[3-(4-hydroxy-piperidin-1-yl)-propoxy]-6-methoxy-quinoline-3-carbonitrile | 122-125 | 531.0 (M + H) |
| 139 | 4-(2,4-Dichloro-5-methoxy-phenylamino)-7-{3-[4-(2-hydroxy-ethyl)-piperazin-1-yl]-propoxy}-6-methoxy-quinoline-3-carbonitrile | 133-137 | 560.1 (M + H) |
| 140 | 4-(2-Bromo-4-chloro-phenylamino)-7-{2-[(2-hydroxy-ethyl-methyl-amino]-ethoxy}-6-methoxy-quinoline-3-carbonitrile | 186-188 | 597.0 (M + H), 254.2 $(M + 2H)^{+2}$ |
| 141 | 4-(2,4-Dichloro-5-methoxy-phenylamino)-7-{3-[(2-hydroxy-ethyl)-methyl-amino]-propoxy}-6-methoxy-quinoline-3-carbonitrile | 129-131 | 533.0 (M + H) |
| 142 | 4-(2,4-Dichloro-5-methoxy-phenylamino)-6-methoxy-7-(3-thiomorpholin-4-yl-propoxy)-quinoline-3-carbonitrile | 116-118 | 505.2 (M + H) |
| 143 | 4-(2,4-Dichloro-5-methoxy-phenylamino)-6-methoxy-7-[3-(2-methoxy-ethylamino)-propoxy]-quinoline-3-carbonitrile | 98-102 | 529.2 (M + H) |
| 144 | 4-(2,4-Dichloro-5-methoxy-phenylamino)-6-methoxy-7-[3-(4-methyl-piperidin-1-yl)-propoxy]-quinoline-3-carbonitrile | 114-117 | 587.2 (M + H) |
| 145 | 4-(2,4-Dichloro-5-methoxy-phenylamino)-7-[3-(2,6-dimethyl-morpholin-4-yl)-propoxy]-6-methoxy-quinoline-3-carbonitrile | 155-157 | 545.3 (M + H) |
| 146 | 4-(2-Bromo-4-chloro-phenylamino)-7-{2-[4-(2-hydroxy-ethyl)-piperazin-1-yl]-ethoxy}-6-methoxy-quinoline-3-carbonitrile | 156-158 | 562.1 (M + H) 281.7 $(M + 2H)^{+2}$ |
| 147 | 4-(2-Bromo-4-chloro-phenylamino)-7-[2-(4-hydroxy-piperidin-1-yl)-ethoxy]-6-methoxy-quinoline-3-carbonitrile | 165-167 | 533.1 (M + H) 267.1 $(M + 2H)^{+2}$ |
| 148 | 4-(2-Bromo-4-chloro-phenylamino)-6-methoxy-7-(2-thiomorpholin-4-yl-ethoxy)-quinoline-3-carbonitrile | 164-166 | 533.0 (M + H) 268.1 $(M + 2H)^{+2}$ |
| 149 | 4-(2,4-Dichloro-5-methoxy-phenylamino)-7-[3-(2,5-dimethyl-pyrrolidin-1-yl)-propoxy]-6-methoxy-quinoline-3-carbonitrile | 115-120 | 529.2 (M + H) |

TABLE 6-continued

| Example | Compound | m.p. (° C.) | mass spectrum |
|---|---|---|---|
| 150 | 4-(2,4-Dichloro-5-methoxy-phenylamino)-7-[3-(3-hydroxy-propylamino)-propoxy]-6-methoxy-quinoline-3-carbonitrile | 142-147 | 505.2 (M + H) |
| 151 | 1-{3[3-Cyano-4-(2,4-dichloro-5-methoxy-phenylamino)-6-methoxy-quinolin-7-yloxy]-propyl}-piperidine-4-carboxylic acid ethyl ester | 95-101 | 587.2 (M + H) |
| 152 | 7-[3-(4-acetyl-1-piperazinyl)propoxy]-4-[(2,4-dichloro-5-methoxyphenyl)amino]-6-methoxy-3-quinolinecarbonitrile | 115-118 | 558.2 (M + H) |
| 153 | 4-(3-chloro-4-fluoroanilino)-7-methyoxy-6(4-morpholinyl)-3-quinolinecarbonitrile | | 413.2 (M + H) |
| 154 | 7-[3-(4-Benzyl-piperazin-1-yl)-propoxy]-4-(2,4-dichloro-5-methoxy-phenylamino)-6-methoxy-quinoline-3-carbonitrile | 140-142 | 606.2 (M + H) |
| 155 | 4-(2,4-Dichloro-5-methoxy-phenylamino)-7-[3-(2-hydroxy-ethylamino)-propoxy]-6-methoxy-quinoline-3-carbonitrile | 161-164 | 491.1 (M + H) |
| 156 | 4-(2,4-Dichloro-5-methoxy-phenylamino)-7-{3-[ethyl-(2-hydroxy-ethyl)-amino]-propoxy}-6-methoxy-quinoline-3-carbonitrile | 162-165 | 519.2 (M + H) |
| 157 | 7-{3-[Bis(2-methoxy-ethyl)-amino]-propoxy}-4-(2,4-dichloro-5-methoxy-phenylamino)-6-methoxy-quinoline-3-carbonitrile | 112-113 | 563.1 (M + H) |
| 158 | 7-{3-[Bis(2-hydroxy-ethyl)-amino]-propoxy}-4-(2,4-dichloro-5-methoxy-phenylamino)-6-methoxy-quinoline-3-carbonitrile | 156-159 | 535.1 (M + H) |
| 159 | 4-(3-chloro-4-fluoroanilino)-7-(4-morpholinyl)-6-nitro-3-quinoline-carbonitrile | 235-239 | 428.1 (M + H) |
| 160 | N-[4-(3-chloro-4-fluoroanilino)-3-cyano-7-(4-morpholinyl)-6-quinolinyl]-2-butynamide | 260-266d | 464.1 (M + H) |
| 161 | 6-amino-4-(3-chloro-4-fluoroanilino)-7-(4-morpholiny1)-3-quinolinecarbonitrile | amorphous | 398.2 (M + H) |
| 162 | 4-(2,4-dichloro-5-methoxyanilino)-6-methoxy-7-(3-{[2-(4-morpholinyl)ethyl] amino}propoxy)-3-quinolinecarbonitrile | 75-80 | 560.2 (M + H) |
| 163 | 7-{3-[(2-anilinoethyl)amino]propoxy}4-(2,4-dichloro-5-methoxyanilino)-6-methoxy-3-quinolinecarbonitrile | 90-94 | 566.2 (M + H) |
| 164 | N-[4-(3-chloro-4-fluoroanilino)-3-cyano-7-(4-morpholinyl)-6-quinolinyl]acrylamide | amorphous | |
| 165 | 4-(3-chloro-4-fluoroanilino)-7-{4-[2-(dimethylamino)ethyl]-1-piperazinyl)-6-nitro-3-quinolinecarbonitrile | | 467.2 (M + H) |
| 166 | 6-amino-4-(3-chloro-4-fluoroanilino)-7-{4-[2-(dimethylamino)ethyl]-1-piperazinyl}-3-quinolinecarbonitrile | | 468.2 (M + H), 234.7 $(M + 2H)^{+2}$ |
| 167 | N-(4-(3-chloro-4-fluoroanilino)-3-cyano-7-{4-[2-(dimethylamino)ethyl]-1-piperazinyl}-6-quinolinyl)acrylamide | | 522.2 (M + H) 261.7 $(M + 2H)^{+2}$ |
| 168 | 4-(2,4-dichloro-5-methoxyanilino)-6-methoxy-7-({2-[4-(2-methoxyethyl)-1-piperazinyl]ethyl}amino)-3-quinolinecarbonitrile | 53-55 | 559.3 (M + H) 280.2 $(M + 2H)^{+2}$ |
| 169 | 4-(2,4-dichloro-5-methoxyanilino)-6-methoxy-7-[3-(2H-1,2,3-triazol-2-yl)propoxy]-3-quinolinecarbonitrile | 190-191 | 499.4 (M + H) |
| 170 | 4-(2,4-dichloro-5-methoxyanilino)-6-methoxy-7-[3-(1H-1,2,3-triazol-1-yl)propoxy]-3-quinolinecarbonitrile | 188-190 | 499.4 (M + H) |
| 171 | 4-(2,4-dichloro-5-methoxyanilino)-6-methoxy-7-(3-thienyl)-3-quinolinecarbonitrile | 215-218 | 456.3 (M + H) |

TABLE 6-continued

| Example | Compound | m.p. (° C.) | mass spectrum |
|---|---|---|---|
| 173 | 4-(2,4-dichloro-5-methoxyanilino)-6-methoxy-7-{[2-(2H-1,2,3-triazol-2-yl)ethyl]amino}-3-quinolinecarbonitrile | 210-211 | 484.1 (M + H) |
| 174 | 4-(2,4-dichloro-5-methoxyanilino)-6-methoxy-7-{[2-(1H-1,2,3-triazol-1-yl)ethyl]amino}-3-quinolinecarbonitrile | 225-228 | 484.1 (M + H) |
| 175 | 4-(2,4-dichloro-5-methoxyanilino)-7-(3-thienyl)-3-quinolinecarbonitrile | 211-212 | 426.0 (M + H) |
| 176 | 4-(2,4-dichloro-5-methoxyanilino)-6-methoxy-7-[3-(1H-1,2,4-triazol-1-yl)propoxy]-3-quinolinecarbonitrile | 206-208 | 499.1 (M + H) |
| 177 | 4-(2,4-dichloro-5-methoxyanilino)-7-[3-(1H-imidazol-1-yl)propoxy]-6-methoxy-3-quinolinecarbonitrile | 155-170 | 498.1 (M + H), 249.6 $(M + 2H)^{+2}$ |
| 178 | 4-(2,4-dichloro-5-methoxyanilino)-6-methoxy-7-[3-(1H-pyrazol-1-yl)propoxy]-3-quinolinecarbonitrile | 187-188 | 498.1 (M + H) |
| 179 | N-[3-cyano-4-(2,4-dichloro-5-methoxyanilino)-6-methoxy-7-quinolinyl]-N-[4-(4-ethyl-1-piperazinyl)butyl]acetamide | 57 | 599.2 (M + H), 300.3 $(M + 2H)^{+2}$ |
| 180 | N-[3-cyano-4-(2,4-dichloro-5-methoxyanilino)-6-methoxy-7-quinolinyl]-N-(3-(4-ethyl-1-piperazinyl)propyl)acetamide | 58.5-59 | 585.1 (M + H) 293.2 $(M + 2H)^{+2}$ |
| 181 | 4-(2,4-dichloro-5-methoxyanilino)-6-methoxy-7-{3-[4-(2-methoxyethyl)-1-piperazinyl]propoxy}-3-quinolinecarbonitrile | 118-120 | 574.1 (M + H) |
| 182 | 4-(2,4-dichloro-5-methoxyanilino)-6-methoxy-7-(1H-pyrrol-1-yl)-3-quinolinecarbonitrile | 229-230 | 439.1 (M + H) |
| 183 | 4-(4-bromo-2-fluoroanilino)-6-methoxy-7-[2-(1H-1,2,3-triazol-1-yl)ethoxy]-3-quinolinecarbonitrile | 180-182 | 483.0 (M + H) |
| 184 | 4-(4-bromo-2-fluoroanilino)-6-methoxy-7-[2-(2H-1,2,3-triazol-2-yl)ethoxy]-3-quinolinecarbonitrile | 93-103 | 483.0 (M + H) |
| 185 | '4-(2,4-dichloro-5-methoxyanilino)-6-methoxy-7-[3-(1H-tetraazol-1-yl)propoxy]-3-quinolinecarbonitrile | 210-214 | 500.1 (M + H) |
| 186 | 4-(2,4-dichloro-5-methoxyanilino)-6-methoxy-7-[3-(2H-tetraazol-2-yl)propoxy]-3-quinolinecarbonitrile | 228-230 | 500.0 (M + H) |
| 187 | 4-(4-bromo-2-fluoroanilino)-6-methoxy-7-[2-(1H-1,2,3-triazol-1-yl)ethoxy]-3-quinolinecarbonitrile | 180-184 | 483.0 (M + H) |
| 188 | 4-(4-bromo-2-fluoroanilino)-6-methoxy-7-[2-(2H-1,2,3-triazol-2-yl)ethoxy]-3-quinolinecarbonitrile | 95-103 | 483.0 (M + H) |
| 189 | 4-(2,4-dichloro-5-methoxyanilino)-7{3-[[2-(dimethylamino)ethyl](methyl)amino]propoxy}-6-methoxy-3-quinolinecarbonitrile | 85-90 | 532.1 (M + H), 266.7 $(M + 2H)^{+2}$ |

What is claimed is:

[1. A compound of Formula 1 having the structure:

1

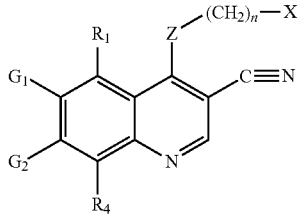

wherein:

X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalky of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, methylmercapto, and benzoylamino;

Z is —NH—, —O—, —S—, or —NR—;

R is alkyl of 1-6 carbon atoms, or carboalkyl of 2-7 carbon atoms;

$G_1$, $G_2$, $R_1$, and $R_4$ are each, independently, hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,

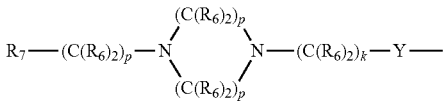

$R_8R_9$—CH—M—$(C(R_6)_2)_k$—Y—, $R_7$—$(C(R_6)_2)_g$—Y—, $R_7$—$(C(R_6)_2)_p$M—$(C(R_6)_2)_k$—Y—, or Het-$(C(R_6)_2)_q$—W—$(C(R_6)_2)_k$—Y— with the proviso that either $G_1$ or $G_2$ or both $G_1$ and $G_2$ must be a radical selected from the group

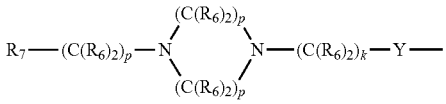

$R_8R_9$—CH—M—$(C(R_6)_2)_k$—Y—, $R'_7$—$C(R_6)_2)_g$—Y—, $R_7$—$(C(R_6)_2)_p$—M—$(C(R_6)_2)_k$—Y—, Het-$(C(R_6)_2)_q$—W—$(C(R_6)_2)_k$—Y—, or $R_2$—$\overset{H}{N}$—;

Y is a divalent radical selected from the group consisting of

—$(CH_2)_a$—, —O—, and —$\underset{R_6}{N}$—;

$R_7$ is —$NR_6R_6$, —J, —$OR_6$, —$N(R_6)_3^+$, or —$NR_6(OR_6)$;

$R'_7$ is —$N(OR_6)$, —$N(R_6)_3^+$, alkenoxy of 1-6 carbon atoms, alkynoxy of 1-6 carbon atoms, N-alkyl-N-alkenylamino of 4 to 12 carbon atoms, N,N-dialkenylamino of 6-12 carbon atoms, N-alkyl-N-alkynylamino of 4 to 12 carbon atoms, N-alkenyl-N-alkynylamino of 4 to 12 carbon atoms, or N,N-dialkynylamino of 6-12 carbon atoms with the proviso that the alkenyl or alkynyl moiety is bound to a nitrogen or oxygen atom through a saturated carbon atom;

M is >$NR_6$, —O—, >N—$(C(R_6)_2)_pNR_6R_6$, or >N—$(C(R_6)_2)_p$—$OR_6$;

W is >$NR_6$, —O— or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

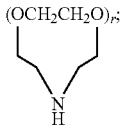

wherein the heterocycle is optionally mono- or di-substituted on carbon or nitrogen with $R_6$, optionally mono- or di-substituted on carbon with hydroxy, —$N(R_6)_2$, or —$OR_6$, optionally mono or di-substituted on carbon with the mono-valent radicals —$(C(R_6)_2)_SOR_6$ or —$(C(R_6)_2)_SN(R_6)_2$, or optionally mono or di-substituted on a saturated carbon with divalent radicals —O— or —O$(C(R_6)_2)_SO$—;

$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;

$R_2$, is selected from the group consisting of

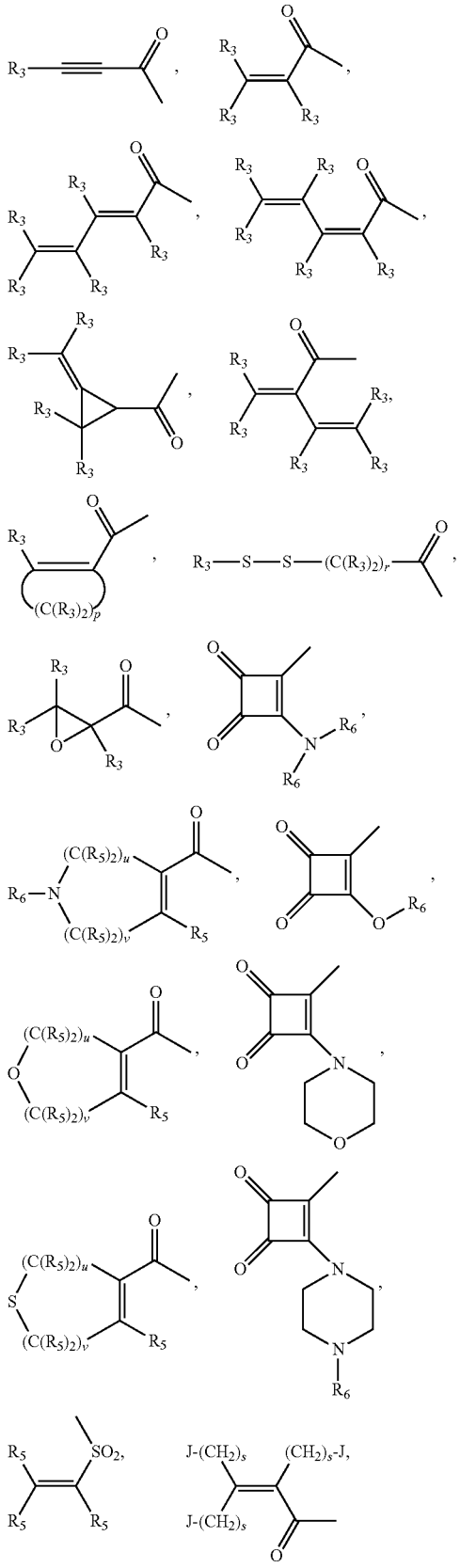

-continued

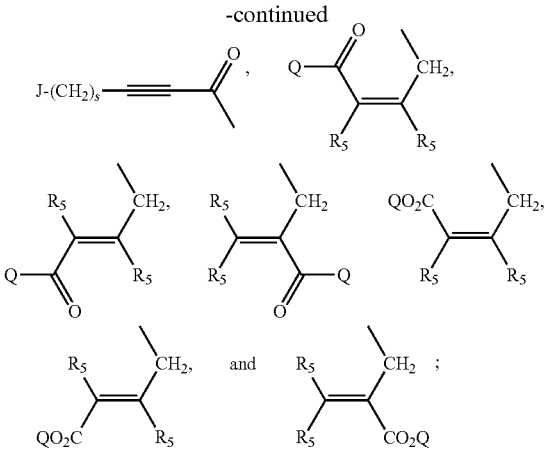

$R_3$ is independently hydrogen, alkyl of 1-6 carbon atoms, carboxy, carboalkoxy of 1-6 carbon atoms, phenyl, carboalkyl of 2-7 carbon atoms,

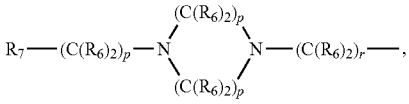

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$, or Het-$(C(R_6)_2)_q$—W—$(C(R_6)_2)_r$—;

with the proviso that at least one of the $R_3$ groups is selected from the group

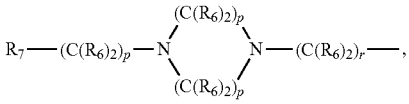

$R'_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

with the proviso that for said at least one $R_3$ group the moiety Het-$(C(R_6)_2)_q$—W—$(C(R_6)_2)$r— cannot be morpholino-N-alkyl wherein the alkyl group is 1-6 carbon atoms, piperidino-N-alkyl wherein the alkyl group is 1-6 carbon atoms, N-alkyl piperidino-N-alkyl wherein either alkyl group is 1-6 carbon atoms, or azacycloalkyl-N-alkyl of 3-11 carbon atoms;

$R_5$ is independently hydrogen, alkyl of 1-6 carbon atoms, carboxy, carboalkoxy of 1-6 carbon atoms, phenyl, carboalkyl of 2-7 carbon atoms,

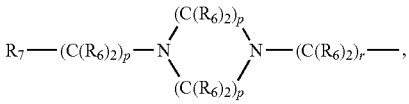

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_rNR_6R_6$, or —$(C(R_6)_2)_rOR_6$;

J is independently hydrogen, chlorine, fluorine, or bromine;

Q is alkyl of 1-6 carbon atoms or hydrogen;

a=0 or 1;

g=1-6;

k=0-4;

n is 0-1;

p=2-4;

q=0-4;

r=1-4;

s=1-6;

u 0-4 and v=0-4, wherein the sum of u+v is 2-4;

or a pharmaceutically acceptable salt thereof, provided that when $R_6$ is alkenyl of 2-7 carbon atoms or alkynyl of 2-7 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^+$, or —$NR_6(OR_6)$, then g 2-6;

when M is —O— and $R_7$ is —$OR_6$, then p=1-4;

when Y is —$NR_6$—, then k=2-4;

when Y is —O— and M or W is —O—, then k=1-4;

when W is not a bond with Het bonded through a nitrogen atom, then q=2-4;

and when W is a bond with Het bonded through a nitrogen atom and Y is —O— or —$NR_6$—, then k=2-4.]

[2. The compound according to claim 1 wherein Z is —NH— and n=0 or a pharmaceutically acceptable salt thereof.]

[3. The compound according to claim 2 wherein X is optionally substituted phenyl or a pharmaceutically acceptable salt thereof.]

[4. The compound according to claim 3 wherein $R_1$ and $R_4$ are hydrogen or a pharmaceutically acceptable salt thereof.]

5. [The] *A* compound [according to claim 1], which is:

a) 1-Methyl-1,2,5,6-tetrahydro-pyridine-3-carboxylic acid[4-(3-bromo-phenylamino)-3-cyano-quinolin-6-yl]-amide or a pharmaceutically acceptable salt thereof;

b) N-[4-[(3-Bromophenyl)amino]-3-cyano-6-quinolinyl]-4-(N-allyl-N-methylamino)-2-butynamide or a pharmaceutically acceptable salt thereof;

c) N-[4-[(3-Bromophenyl)amino]-3-cyano-6-quinolinyl]-4-(N-methoxyethyl-N-methylamino)-2-butynamide or a pharmaceutically acceptable salt thereof;

d) N-[4-[(3-Bromophenyl)amino]-3-cyano-6-quinolinyl]-4-(bis-(2-methoxyethyl)amino)-2-butynamide or a pharmaceutically acceptable salt thereof;

e) 4-Methoxymethoxy-but-2-ynoic acid[4-(3-bromo-phenylamino)-3-cyano-quinolin-6-yl]-amide or a pharmaceutically acceptable salt thereof;

f) 4-(4-Chloro-2-fluoro-phenylamino)-6-methoxy-7-(2-pyridin-4-yl-ethoxy)-1-quinoline-3-carbonitrile or a pharmaceutically acceptable salt thereof;

g) 4-(2-Methoxy-ethoxy)-but-2-ynoic acid[4-(3-bromo-phenylamino)-3-cyano-quinolin-6-yl]-amide or a pharmaceutically acceptable salt thereof;

h) [4-((2S)-2-Methoxymethylpyrrolidin-1-yl)but-2-ynoic Acid[4-(3-bromophenylamino)-3-cyanoquinolin-6-yl] amide] *4-((2S)-2-Methoxymethylpyrrolidin-1-yl)but-2-ynoic acid[4-(3-bromophenylamino)-3-cyanoquinolin-6-yl]-amide* or a pharmaceutically acceptable salt thereof;

i) [4-(1,4-Dioxa-8-azaspiro[4,5]dec-8-yl)but-2-ynoic Acid [4-(3-Bromophenylamino)-3-cyanoquinolin-6-yl] amide] *4-(1,4-Dioxa-8-azaspiro[4,5]dec-8-yl)but-2-*

*ynoic acid[4-(3-Bromophenylamino)-3-cyanoquinolin-6-yl]-amide* or a pharmaceutically acceptable salt thereof;

j) [4-(3-Bromo-phenylamino)-6-(2-ethoxy-3,4-dioxo-cyclobut-1-enylamino)-quinoline-3-carbonitrile] *4-(3-Bromo-phenylamino)-6-[(2-ethoxy-3,4-dioxo-cyclobut-1-enyl]amino)-quinoline-3-carbonitrile* or a pharmaceutically acceptable salt thereof;

k) [4-[(2-Methoxy-ethyl)-methyl-amino]-but-2-enoic acid [4-(3-chloro-4-fluoro-phenylamino)-3-cyano-7-methoxy-quinolin-6-yl]-amide] *4-[(2-Methoxyethyl)(methyl)amino]-but-2-enoic acid[4-(3-chloro-4-fluoro-phenylamino)-3-cyano-7-methoxy-quinolin-6-yl]-amide* or a pharmaceutically acceptable salt thereof;

l) (S)-4-(2-Methoxymethyl-pyrrolidin-1-yl)-but-2-enoic acid[4-(3-chloro-4-fluoro-phenylamino)-3-cyano-7-methoxy-quinolin-6-yl]-amide dihydrochloride or a pharmaceutically acceptable salt thereof;

m) 4-(3-Hydroxymethyl-piperidin-1-yl)-but-2-enoic acid [4-(3-chloro-4-fluoro-phenylamino)-3-cyano-7-methoxy-quinolin-6-yl]-amide or a pharmaceutically acceptable salt thereof;

n) 4-(1,4-Dioxa-8-aza-spiro[4.5]dec-8-yl)-but-2-enoic acid[4-(3-chloro-4-fluoro-phenylamino)-3-cyano-7-methoxy-quinolin-6-yl]-amide or a pharmaceutically acceptable salt thereof;

o) 4-(2-Hydroxymethyl-piperidin-1-yl)-but-2-enoic acid [4-(3-chloro-4-fluoro-phenylamino)-3-cyano-7-methoxy-quinolin-6-yl]-amide or a pharmaceutically acceptable salt thereof;

p) 4-Bromo-but-2-enoic acid[4-(3-chloro-4-fluoro-phenylamino)-3-cyano-7-methoxy-quinolin-6-yl]-amide or a pharmaceutically acceptable salt thereof;

q) 4-(3-hydroxy-4-methyl-phenylamino)-6-methoxy-7-(3-pyridin-4-yl-propoxy)-quinoline-3-carbonitrile or a pharmaceutically acceptable salt thereof;

r) [4-Diallylamino-but-2-enoic acid[4-(3-chloro-4-fluoro-phenylamino)-3cyano-7-methoxy-quinolin-6-yl]-amide] *4-Diallylamino-but-2-enoic acid[4-(3-chloro-4-fluoro-phenylamino)-3-cyano-7-methoxy-quinolin-6-yl]-amide* or a pharmaceutically acceptable salt thereof;

s) 4-[Bis-(2-methoxy-ethyl)-amino]-but-2-enoic acid[4-(3-chloro-4-fluoro-phenylamino)-3-cyano-7-methoxy-quinolin-6-yl]-amide or a pharmaceutically acceptable salt thereof;

t) [4-([1,3]Dioxolan-2-ylmethyl-methyl-amino)-but-2-enoic acid3-cyano-7-methoxy-quinolin-6-yl]-amide] *4-[([1,3]Dioxolan-2-yl-methyl)(methyl)amino]-but-2-enoic acid[3-cyano-7-methoxy-quinolin-6-yl]-amide* or a pharmaceutically acceptable salt thereof;

u) 4-[Bis-(2-hydroxy-ethyl)-amino]-but-2-enoic acid[4-(3-chloro-4-fluoro-phenylamino)-3-cyano-7-methoxy-quinolin-6-yl]-amide or a pharmaceutically acceptable salt thereof;

v) 4-Thiomorpholin-4-yl-but-2-enoic acid[4-(3-chloro-4-fluoro-phenylamino)-3-cyano-7-methoxy-quinolin-6-yl]-amide or a pharmaceutically acceptable salt thereof;

w) 4-[4-(2-Hydroxy-ethyl)-piperazin-1-yl]-but-2-enoic acid[4-(3-chloro-4-fluoro-phenylamino)-3-cyano-7-methoxy-quinolin-6-yl]-amide or a pharmaceutically acceptable salt thereof;

x) 4-(1,4,7-Trioxa-10-aza-cyclododec-10-yl)-but-2-enoic acid[4-(3-chloro-4-fluoro-phenylamino)-3-cyano-7-methoxy-quinolin-6-yl]-amide or a pharmaceutically acceptable salt thereof;

y) [4-(Methoxy-methyl-amino)-but-2-enoic acid[4-(3-chloro-4-fluoro-phenylamino)-3-cyano-7-methoxy-quinolin-6-yl]-amide] *4-[(Methoxy)(methyl)amino]-but-2-enoic acid[4-(3-chloro-4-fluoro-phenylamino)-3-cyano-7-methoxy-quinolin-6-yl]-amide* or a pharmaceutically acceptable salt thereof;

z) 4-(4-Hydroxy-piperidin-1-yl)-but-2-enoic acid[4-(3-chloro-4-fluoro-phenylamino)-3-cyano-7-methoxy-quinolin-6-yl]-amide or a pharmaceutically acceptable salt thereof;

aa) 4-[1,4']Bipiperidinyl-1'-yl-but-2-enoic acid[4-(3-chloro-4-fluoro-phenylamino)-3-cyano-7-methoxy-quinolin-6-yl]-amide or a pharmaceutically acceptable salt thereof;

bb) 4-Thiazolidin-3-yl-but-2-enoic acid[4-(3-chloro-4-fluoro-phenylamino)-3-cyano-7-methoxy-quinolin-6-yl]-amide or a pharmaceutically acceptable salt thereof;

cc) 3-{3-[4-(3-Chloro-4-fluoro-phenylamino)-3-cyano-7-methoxy-quinolin-6-ylcarbamoyl]-allyl}-4-methyl-thiazol-3-ium bromide or a pharmaceutically acceptable salt thereof;

dd) 4-(2,6-Dimethyl-piperidin-1-yl)-but-2-enoic acid[4-(3-chloro-4-fluoro-phenylamino)-3-cyano-7-methoxy-quinolin-6-yl]-amide or a pharmaceutically acceptable salt thereof;

ee) 4-[Bis-(2-hydroxy-propyl)-amino]-but-2-enoic acid [4-(3-chloro-4-fluoro-phenylamino)-3-cyano-7-methoxy-quinolin-6-yl]-amide or a pharmaceutically acceptable salt thereof;

ff) 4-(3-Hydroxy-pyrrolidin-1-yl)-but-2-enoic acid[4-(3-chloro-4-fluoro-phenylamino)-3-cyano-7-methoxy-quinolin-6-yl]-amide or a pharmaceutically acceptable salt thereof;

gg) [4-[(2-Hydroxy-ethyl)-methyl-amino]-but-2-enoic acid[4-(3-chloro-4-fluoro-phenylamino)-3-cyano-7-methoxy-quinolin-6-yl]-amide] *4-[(2-Hydroxyethyl)(methyl)amino]-but-2-enoic acid[4-(3-chloro-4-fluoro-phenylamino)-3-cyano-7-methoxy-quinolin-6-yl]-amide* or a pharmaceutically acceptable salt thereof;

hh) 4-(2,5-Dimethyl-pyrrolidin-1-yl)-but-2-enoic acid[4-(3-chloro-4-fluoro-phenylamino)-3-cyano-7-methoxy-quinolin-6-yl]-amide or a pharmaceutically acceptable salt thereof;

ii) 4-(4,4-Dihydroxy-piperidin-1-yl)-but-2-enoic acid[4-(3-chloro-4-fluoro-phenylamino)-3-cyano-7-methoxy-quinolin-6-yl]-amide or a pharmaceutically acceptable salt thereof;

jj) 4-(3-Chloro-4-fluoro-phenylamino)-7-methoxy-6-pyrrolidin-1-yl-quinoline-3-carbonitrile or a pharmaceutically acceptable salt thereof;

kk) 4-(3-Chloro-4-fluroanilino)-7-methoxy-6-(1H-pyrrol-1-yl)-3-quinolinecarbonitrile or a pharmaceutically acceptable salt thereof;

ll) 6-(1-Aziridinyl)-4-(3-chloro-4-fluoroanilino)-7-methoxy-3-quinolinecarbonitrile or a pharmaceutically acceptable salt thereof;

mm) [4-[(2-Methoxy-ethyl)-methyl-amino]-but-2-enoic acid[4-(3-bromo-phenylamino)-3-cyano-7-ethoxy-quinolin-6-yl]-amide] *4-[(2-Methoxyethyl)(methyl)amino]-but-2-enoic acid[4-(3-bromo-phenylamino)-3-cyano-7-ethoxy-quinolin-6-yl]-amide* or a pharmaceutically acceptable salt thereof;

nn) 4-(2,4-Dichloro-5-methoxy-phenylamino)-7-[3-(4-hydroxy-piperidin-1-yl)-propoxy]-6-methoxy-quinoline-3-carbonitrile or a pharmaceutically acceptable salt thereof;

oo) 4-(2,4-Dichloro-5-methoxy-phenylamino)-7-{3-[4-(2-hydroxy-ethyl)-piperazin-1-yl]-propoxy}-6-methoxy-quinoline-3-carbonitrile or a pharmaceutically acceptable salt thereof;

pp) [4-(2-Bromo-4-chloro-phenylamino)-7-{2-[(2-hydroxy-ethyl)-methyl-amino]-ethoxy}-6-methoxy-quinoline-3-carbonitrile] *4-(2-Bromo-4-chloro-phenylamino)-7-{2-[(2-hydroxyethyl)(methyl)amino]-ethoxy}-6-methoxy-quinoline-3-carbonitrile* or a pharmaceutically acceptable salt thereof;

qq) [4-(2,4-Dichloro-5-methoxy-phenylamino)-7-{3-[(2-hydroxy-ethyl)-methyl-amino]-propoxy}-6-methoxy-quinoline-3-carbonitrile] *4-(2,4-Dichloro-5-methoxy-phenylamino)-7-{3-[(2-hydroxyethyl)(methyl)amino]-propoxy}-6-methoxy-quinoline-3-carbonitrile* or a pharmaceutically acceptable salt thereof;

rr) 4-(2,4-Dichloro-5-methoxy-phenylamino)-6-methoxy-7-(3-thiomorpholin-4-yl-propoxy)-quinoline-3-carbonitrile or a pharmaceutically acceptable salt thereof;

ss) 4-(2,4-Dichloro-5-methoxy-phenylamino)-6-methoxy-7-[3-(2-methoxy-ethylamino)-propoxy]-quinoline-3-carbonitrile or a pharmaceutically acceptable salt thereof;

tt) 4-(2,4-Dichloro-5-methoxy-phenylamino)-6-methoxy-7-[3-(4-methyl-piperidin-1-yl)-propoxy]-quinoline-3-carbonitrile or a pharmaceutically acceptable salt thereof;

uu) 4-(2,4-Dichloro-5-methoxy-phenylamino)-7-[3-(2,6-dimethyl-morpholin-4-yl)-propoxy]-6-methoxy-quinoline-3-carbonitrile or a pharmaceutically acceptable salt thereof;

vv) 4-(2-Bromo-4-chloro-phenylamino)-7-{2-[4-(2-hydroxy-ethyl)-piperazin-1-yl]-ethoxy}-6-methoxy-quinoline-3-carbonitrile or a pharmaceutically acceptable salt thereof;

ww) 4-(2-Bromo-4-chloro-phenylamino)-7-[2-(4-hydroxy-piperidin-1-yl)-ethoxy]-6-methoxy-quinoline-3-carbonitrile or a pharmaceutically acceptable salt thereof;

xx) 4-(2-Bromo-4-chloro-phenylamino)-6-methoxy-7-(2-thiomorpholin-4-yl-ethoxy)-quinoline-3-carbonitrile or a pharmaceutically acceptable salt thereof;

yy) 4-(2,4-Dichloro-5-methoxy-phenylamino)-7-[3-(2,5-dimethyl-pyrrolidin-1-yl)-propoxy]-6-methoxy-quinoline-3-carbonitrile or a pharmaceutically acceptable salt thereof;

zz) 4-(2,4-Dichloro-5-methoxy-phenylamino)-7-[3-(3-hydroxy-propylamino)-propoxy]-6-methoxy-quinoline-3-carbonitrile or a pharmaceutically acceptable salt thereof;

aaa) [1-{3-[3-Cyano-4-(2,4-dichloro-5-methoxy-phenylamino)-6-methoxy-quinolin-7-yloxy]-propyl}-piperidine-4-carboxylic acid ethyl ester] *1-{3-[3-Cyano-4-(2,4-dichloro-5-methoxy-phenylamino)-6-methoxy-quinolin-7-yl-oxy]-propyl}-piperidine-4-carboxylic acid ethyl ester* or a pharmaceutically acceptable salt thereof;

bbb) 7-[3-(4-acetyl-1-piperazinyl)propoxy]-4-[(2,4-dichloro-5-methoxyphenyl)amino]-6-methoxy-3-quinolinecarbonitrile or a pharmaceutically acceptable salt thereof;

ccc) [4-(3-chloro-4-fluoroanilino)-7-methyoxy-6(4-morpholinyl)-3-quinolinecarbonitrile] *4-(3-Chloro-4-fluoroanilino)-7-methoxy-6-(4-morpholinyl)-3-quinolinecarbonitrile* or a pharmaceutically acceptable salt thereof;

ddd) 7-[3-(4-Benzyl-piperazin-1-yl)-propoxy]-4-(2,4-dichloro-5-methoxy-phenylamino)-6-methoxy-quinoline-3-carbonitrile or a pharmaceutically acceptable salt thereof;

eee) 4-(2,4-Dichloro-5-methoxy-phenylamino)-7-[3-(2-hydroxy-ethylamino)-propoxy]-6-methoxy-quinoline-3-carbonitrile or a pharmaceutically acceptable salt thereof;

fff) 4-(2,4-Dichloro-5-methoxy-phenylamino)-7-{3-[ethyl-(2-hydroxy-ethyl)-amino]-propoxy}-6-methoxy-quinoline-3-carbonitrile or a pharmaceutically acceptable salt thereof;

ggg) 7-{3-[Bis-(2-methoxy-ethyl)-amino]-propoxy}-4-(2,4-dichloro-5-methoxy-phenylamino)-6-methoxy-quinoline-3-carbonitrile or a pharmaceutically acceptable salt thereof;

hhh) 7-{3-[Bis-(2-hydroxy-ethyl)-amino]-propoxy}-4-(2,4-dichloro-5-methoxy-phenylamino)-6-methoxy-quinoline-3-carbonitrile or a pharmaceutically acceptable salt thereof;

iii) 4-(3-chloro-4-fluoroanilino)-7-(4-morpholinyl)-6-nitro-3-quinolinecarbonitrile or a pharmaceutically acceptable salt thereof;

jjj) N-[4-(3-chloro-4-fluoroanilino)-3-cyano-7-(4-morpholinyl)-6-quinolinyl]-2-butynamide or a pharmaceutically acceptable salt thereof;

kkk) 6-amino-4-(3-chloro-4-fluoroanilino)-7-(4-morpholinyl)-3-quinolinecarbonitrile or a pharmaceutically acceptable salt thereof;

lll) 4-(2,4-dichloro-5-methoxyanilino)-6-methoxy-7-(3-{[2-(4-morpholinyl)ethyl]amino}propoxy)-3-quinolinecarbonitrile or a pharmaceutically acceptable salt thereof;

mmm) 7-{3-[(2-anilinoethyl)amino]propoxy}-4-(2,4-dichloro-5-methoxyanilino)-6-methoxy-3-quinolinecarbonitrile or a pharmaceutically acceptable salt thereof;

nnn) N-[4-(3-chloro-4-fluoroanilino)-3-cyano-7-(4-morpholinyl)-6-quinolinyl]acrylamide or a pharmaceutically acceptable salt thereof;

ooo) 4-(3-chloro-4-fluoroanilino)-7-{4-[2-(dimethylamino)ethyl]-1-piperazinyl}-6-nitro-3-quinolinecarbonitrile or a pharmaceutically acceptable salt thereof;

ppp) 6-amino-4-(3-chloro-4-fluoroanilino)-7-{4-[2-(dimethylamino)ethyl]-1-piperazinyl}-3-quinolinecarbonitrile or a pharmaceutically acceptable salt thereof;

qqq) N-(4-(3-chloro-4-fluoroanilino)-3-cyano-7-{4-[2-(dimethylamino)ethyl]-1-piperazinyl}-6-quinolinyl) acrylamide or a pharmaceutically acceptable salt thereof;

rrr) 4-(2,4-dichloro-5-methoxyanilino)-6-methoxy-7-({2-[4-(2-methoxyethyl)-1-piperazinyl]ethyl}amino)-3-quinolinecarbonitrile or a pharmaceutically acceptable salt thereof;

sss) 4-(2,4-dichloro-5-methoxyanilino)-6-methoxy-7-[3-(2H-1,2,3-triazol-2-yl)propoxy]-3-quinolinecarbonitrile or a pharmaceutically acceptable salt thereof;

ttt) 4-(2,4-dichloro-5-methoxyanilino)-6-methoxy-7-[3-(1H-1,2,3-triazol-1-yl)propoxy]-3-quinolinecarbonitrile or a pharmaceutically acceptable salt thereof;

uuu) 4-(2,4-dichloro-5-methoxyanilino)-6-methoxy-7-(3-thienyl)-3-quinolinecarbonitrile or a pharmaceutically acceptable salt thereof;

vvv) 4-[(E)-2-(2-quinolinyl)ethenyl]aniline or a pharmaceutically acceptable salt thereof;

www) 4-(2,4-dichloro-5-methoxyanilino)-6-methoxy-7-{[2-(2H-1,2,3-triazol-2-yl)ethyl]amino}-3-quinolinecarbonitrile or a pharmaceutically acceptable salt thereof;

xxx) 4-(2,4-dichloro-5-methoxyanilino)-6-methoxy-7-{[2-(1H-1,2,3-triazol-1-yl)ethyl]amino}-3-quinolinecarbonitrile or a pharmaceutically acceptable salt thereof;

yyy) 4-(2,4-dichloro-5-methoxyanilino)-7-(3-thienyl)-3-quinolinecarbonitrile or a pharmaceutically acceptable salt thereof;

zzz) 4-(2,4-dichloro-5-methoxyanilino)-6-methoxy-7-[3-(1H,1,2,4-triazol-1-yl)propoxy]-3-quinolinecarbonitrile or a pharmaceutically acceptable salt thereof;

aaaa) 4-(2,4-dichloro-5-methoxyanilino)-7-[3-(1H-imidazol-1-yl)propoxy]-6-methoxy-3-quinolinecarbonitrile or a pharmaceutically acceptable salt thereof;

bbbb) 4-(2,4-dichloro-5-methoxyanilino)-6-methoxy-7-[3-(1H-pyrazol-1-yl)propoxy]-3-quinolinecarbonitrile or a pharmaceutically acceptable salt thereof;

cccc) N-[3-cyano-4-(2,4-dichloro-5-methoxyanilino)-6-methoxy-7-quinolinyl]-N-[4-ethyl-1-piperazinyl)butyl]acetamide or a pharmaceutically acceptable salt thereof;

dddd) N-[3-cyano-4-(2,4-dichloro-5-methoxyanilino)-6-methoxy-7-quinolinyl]-N-(3-(4-ethyl-1-piperazinyl)propyl)acetamide or a pharmaceutically acceptable salt thereof;

eeee) 4-(2,4-dichloro-5-methoxyanilino)-6-methoxy-7-{3-[4-(2-methoxyethyl)-1-piperazinyl]propoxy}-3-quinolinecarbonitrile or a pharmaceutically acceptable salt thereof;

ffff) 4-(2,4-dichloro-5-methoxyanilino)-6-methoxy-7-(1H-pyrrol-1-yl)-3-quinolinecarbonitrile or a pharmaceutically acceptable salt thereof;

gggg) 4-(4-bromo-2-fluoroanilino)-6-methoxy-7-[2-(1H-1,2,3-triazol-1-yl)ethoxy]-3-quinolinecarbonitrile or a pharmaceutically acceptable salt thereof;

hhhh) 4-(4-bromo-2-fluoroanilino)-6-methoxy-7-[2-(2H-1,2,3-triazol-2-yl)ethoxy]-3-quinolinecarbonitrile or a pharmaceutically acceptable salt thereof;

iiii) 4-(2,4-dichloro-5-methoxyanilino)-6-methoxy-7-[3-(1H-tetraazol-1-yl)propoxy]-3-quinolinecarbonitrile or a pharmaceutically acceptable salt thereof;

jjjj) 4-(2,4-dichloro-5-methoxyanilino)-6-methoxy-7-[3-(2H-tetraazol-2-yl)propoxy]-3-quinolinecarbonitrile or a pharmaceutically acceptable salt thereof;

kkkk) 4-(4-bromo-2-fluoroanilino)-6-methoxy-7-[2-(1H-1,2,3-triazol-1-yl)ethoxy]-3-quinolinecarbonitrile or a pharmaceutically acceptable salt thereof;

llll) 4-(4-bromo-2-fluoroanilino)-6-methoxy-7-[2-(2H-1,2,3-triazol-2-yl)ethoxy]-3-quinolinecarbonitrile or a pharmaceutically acceptable salt thereof; or mmmm) 4-(2,4-dichloro-5-methoxyanilino)-7-{3-[[2-(dimethylamino)ethyl](methyl)amino]propoxy}-6-methoxy-3-quinolinecarbonitrile or a pharmaceutically acceptable salt thereof.

[6. A method of treating, inhibiting the growth of, or eradicating a neoplasm in a mammal in need thereof which comprises administering to said mammal an effective amount of a compound of Formula 1 having the structure

1

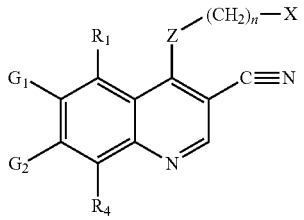

wherein:

X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalky of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, methylmercapto, and benzoylamino;

Z is —NH—, —O—, —S—, or —NR—;

R is alkyl of 1-6 carbon atoms, or carboalkyl of 2-7 carbon atoms;

$G_1$, $G_2$, $R_1$, and $R_4$ are each, independently, hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,

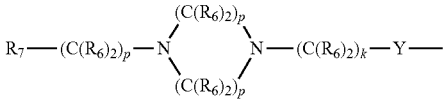

$R_8R_9$—CH—M—$(C(R_6)_2)_k$—Y—, $R_7$—$(C(R_6)_2)_g$—Y—, $R_7$—$(C(R_6)_2)_p$—M—$(C(R_6)_2)_p$—M—$(C(R_6)_2)_k$—Y—, or Het-$(C(R_6)_2)_q$—W—$(C(R_6)_2)_k$—Y— with the proviso that either $G_1$ or $G_2$ or both $G_1$ and $G_2$ must be a radical selected from the group

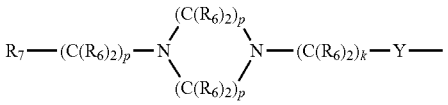

$R_8R_9$—CH—M—$(C(R_6)_2)_k$—Y—, $R'_7$—$(C(R_6)_2)_g$—Y—, $R_7$—$(C(R_6)_2)_p$—M—$(C(R_6)_2)_k$—Y—, Het-$(C(R_6)_2)_q$—W—$(C(R_6)_2)_k$—Y—, or $R_2$—$\overset{H}{N}$—;

Y is a divalent radical selected from the group consisting of

—$(CH_2)_a$—, —O—, and —$\underset{R_6}{N}$—;

$R_7$ is —$NR_6R_6$, -J, —$OR_6$, —$N(R_6)_3^+$, or —$NR_6(OR_6)$;

$R'_7$ is —$NR_6(OR_6)$, —$N(R_6)_3^+$, alkenoxy of 1-6 carbon atoms, alkynoxy of 1-6 carbon atoms, N-alkyl-N-alkenylamino of 4 to 12 carbon atoms, N,N-dialkenylamino of 6-12 carbon atoms, N-alkyl-N-alkynylamino of 4 to 12 carbon atoms, N-alkenyl-N-alkynylamino of 4 to 12 carbon atoms, or N,N-dialkynylamino of 6-12 carbon atoms with the proviso that the alkenyl or alkynyl moiety is bound to a nitrogen or oxygen atom through a saturated carbon atom;

M is >$NR_6$, —O—, >N—$(C(R_6)_2)_pNR_6R_6$, or >N—$(C(R_6)_2)_p$—$OR_6$;

W is >$NR_6$, —O— or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

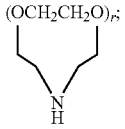

wherein the heterocycle is optionally mono- or di-substituted on carbon or nitrogen with $R_6$, optionally mono- or di-substituted on carbon with hydroxy, —$N(R_6)_2$, or —$OR_6$, optionally mono or di-substituted on carbon with the mono-valent radicals —$(C(R_6)_2)_sOR_6$ or —$(C(R_6)_2)_sN(R_6)_2$, or optionally mono or di-substituted on a saturated carbon with divalent radicals —O— or —O$(C(R_6)_2)_s$O—;

$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;

$R_2$, is selected from the group consisting of

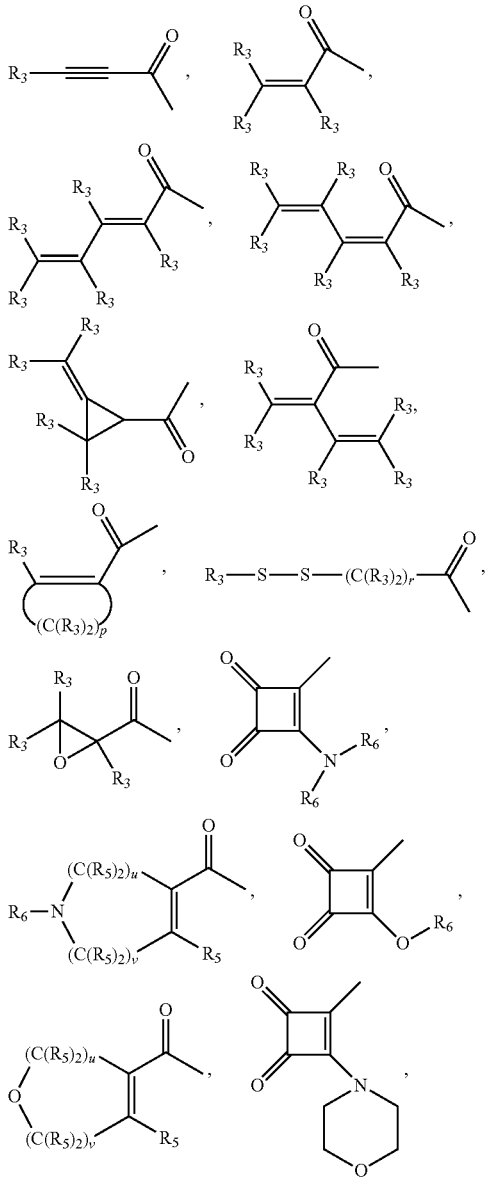

-continued

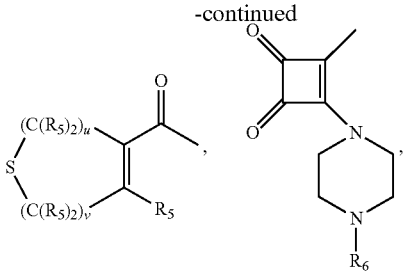

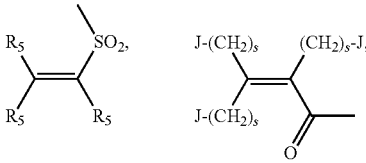

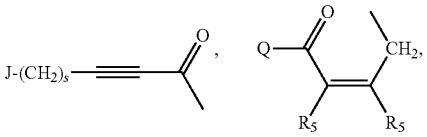

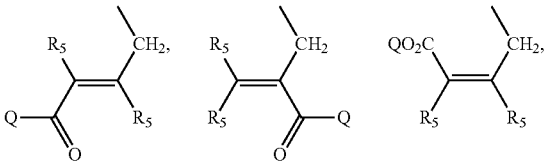

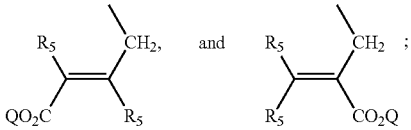

$R_3$ is independently hydrogen, alkyl of 1-6 carbon atoms, carboxy, carboalkoxy of 1-6 carbon atoms, phenyl, carboalkyl of 2-7 carbon atoms,

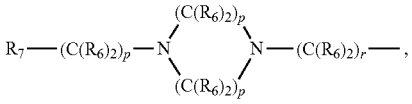

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

with the proviso that at least one of the $R_3$ groups is selected from the group

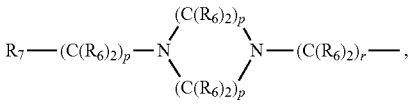

$R'_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

with the proviso that for said at least one $R_3$ group the moiety Het-$(C(R_6)_2)_q$—W—$(C(R_6)_2)_r$— cannot be morpholino-N-alkyl wherein the alkyl group is 1-6 carbon atoms, piperidino-N-alkyl wherein the alkyl group is 1-6 carbon atoms, N-alkyl piperidino-N-alkyl wherein either alkyl group is 1-6 carbon atoms, or azacycloalkyl-N-alkyl of 3-11 carbon atoms;

$R_5$ is independently hydrogen, alkyl of 1-6 carbon atoms, carboxy, carboalkoxy of 1-6 carbon atoms, phenyl, carboalkyl of 2-7 carbon atoms,

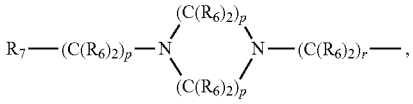

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_rNR_6R_6$, or —$(C(R_6)_2)_rOR_6$;

J is independently hydrogen, chlorine, fluorine, or bromine;

Q is alkyl of 1-6 carbon atoms or hydrogen;

a=0 or 1;

g=1-6;

k=0-4;

n is 0-1;

p=2-4;

q=0-4;

r=1-4;

s=1-6;

u 0-4 and v=0-4, wherein the sum of u+v is 2-4;

or a pharmaceutically acceptable salt thereof, provided that when $R_6$ is alkenyl of 2-7 carbon atoms or alkynyl of 2-7 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^+$, or —$NR_6(OR_6)$, then g=2-6;

when M is —O— and $R_7$ is -$OR_6$, then p=1-4;

when Y is —$NR_6$—, then k=2-4;

when Y is —O— and M or W is —O—, then k=1-4;

when W is not a bond with Het bonded through a nitrogen atom, then q=2-4;

and when W is a bond with Het bonded through a nitrogen atom and Y is —O— or —$NR_6$—, then k=2-4.]

[7. The method according to claim 6 wherein the neoplasm is selected from the group consisting of breast, kidney, bladder, mouth, larynx, esophagus, stomach, colon, ovary, and lung.]

[8. A method of treating, inhibiting the progression of, or eradicating polycystic kidney disease in a mammal in need thereof which comprises administering to said mammal an effective amount of a compound of formula 1 having the structure

1

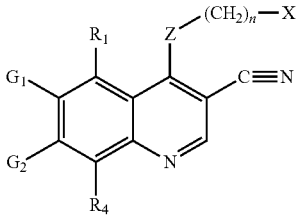

wherein:

X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalky of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, methylmercapto, and benzoylamino;

Z is —NH—, —O—, —S—, or —NR—;

R is alkyl of 1-6 carbon atoms, or carboalkyl of 2-7 carbon atoms;

$G_1$, $G_2$, $R_1$, and $R_4$ are each, independently, hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,

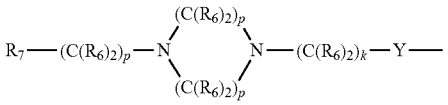

$R_8R_9$—CH—M—$(C(R_6)_2)_k$—Y—, $R_7$—$(C(R_6)_2)_g$—Y—, $R_7$—$(C(R_6)_2)_p$—M—$(C(R_6)_2)_k$—Y—, or Het-$(C(R_6)_2)_q$—W—$(C(R_6)_2)_k$—Y— with the proviso that either $G_1$ or $G_2$ or both $G_1$ and $G_2$ must be a radical selected from the group

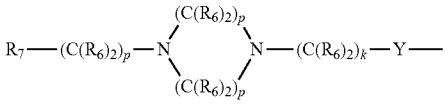

$R_8R_9$—CH—M—$(C(R_6)_2)_k$—Y—, $R'_7$—$(C(R_6)_2)_g$—Y—, $R_7$—$(C(R_6)_2)_p$—M—$(C(R_6)_2)_k$—Y—, Het-$(C(R_6)_2)_q$—W—$(C(R_6)_2)_k$—Y—, or $R_2$—$N^{H}$—;

Y is a divalent radical selected from the group consisting of

—$(CH_2)_a$—, —O—, and —N($R_6$)—;

$R_7$ is —$NR_6R_6$, —J, —$OR_6$, —$N(R_6)_3^+$, or —$NR_6(OR_6)$, $R'_7$ is —$NR_6(OR_6)$, —$N(R_6)_3^+$, alkenoxy of 1-6 carbon atoms, alkynoxy of 1-6 carbon atoms, N-alkyl-N-alkenylamino of 4 to 12 carbon atoms, N,N-dialkenylamino of 6-12 carbon atoms, N-alkyl-N-alkynylamino of 4 to 12 carbon atoms, N-alkenyl-N-alkynylamino of 4 to 12 carbon atoms, or N,N-dialkynylamino of 6-12 carbon atoms with the proviso that the alkenyl or alkynyl moiety is bound to a nitrogen or oxygen atom through a saturated carbon atom;

M is >$NR_6$, —O—, >N—$(C(R_6)_2)_pNR_6R_6$, or >N—$(C(R_6)_2)_p$—$OR_6$;

W is >$NR_6$, —O— or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

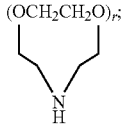

wherein the heterocycle is optionally mono- or di-substituted on carbon or nitrogen with $R_6$, optionally mono- or di-substituted on carbon with hydroxy, —$N(R_6)_2$, or —$OR_6$, optionally mono or di-substituted on carbon with the mono-valent radicals —$(C(R_6)_2)_sOR_6$ or —$(C(R_6)_2)_sN(R_6)_2$, or optionally mono or di-substituted on a saturated carbon with divalent radicals —O— or —O$(C(R_6)_2)_s$O—;

$R_6$ is hydrogen, alkyl of 1-6 carbon atoms, alkenyl of 2-6 carbon atoms, alkynyl of 2-6 carbon atoms, cycloalkyl 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;

$R_2$, is selected from the group consisting of

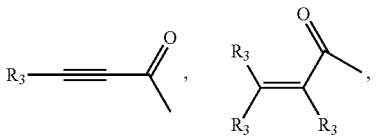

-continued

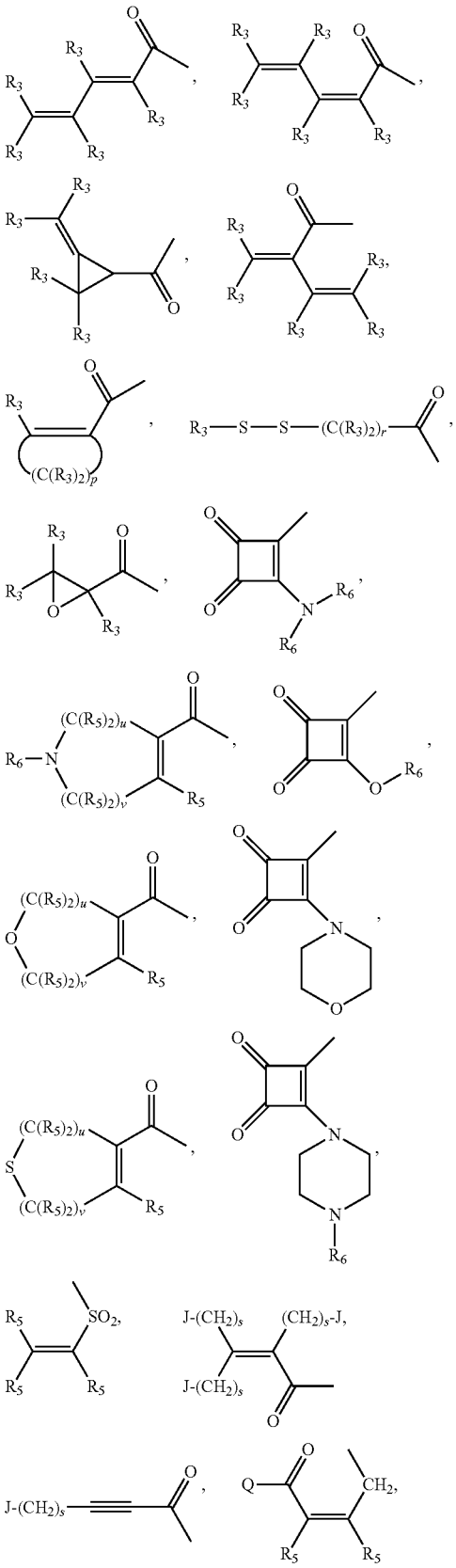

-continued

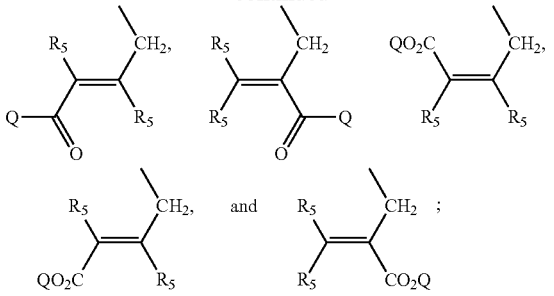

$R_3$ is independently hydrogen, alkyl of 1-6 carbon atoms, carboxy, carboalkoxy of 1-6 carbon atoms, phenyl, carboalkyl of 2-7 carbon atoms,

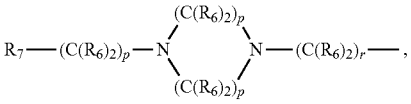

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

with the proviso that at least one of the $R_3$ groups is selected from the group

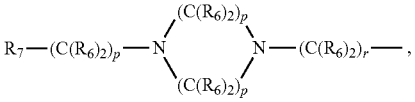

$R'_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

with the proviso that for said at least one $R_3$ group the moiety Het-$(C(R_6)_2)_q$—W—$(C(R_6)_2)_r$— cannot be morpholino-N-alkyl wherein the alkyl group is 1-6 carbon atoms, piperidino-N-alkyl wherein the alkyl group is 1-6 carbon atoms, N-alkyl piperidino-N-alkyl wherein either alkyl group is 1-6 carbon atoms, or azacycloalkyl-N-alkyl of 3-11 carbon atoms;

$R_5$ is independently hydrogen, alkyl of 1-6 carbon atoms, carboxy, carboalkoxy of 1-6 carbon atoms, phenyl, carboalkyl of 2-7 carbon atoms,

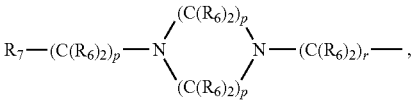

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_rNR_6R_6$, or —$(C(R_6)_2)_rOR_6$;

J is independently hydrogen, chlorine, fluorine, or bromine;

Q is alkyl of 1-6 carbon atoms or hydrogen;

a=0 or 1;

g=1-6;

k=0-4;

n is 0-1;

p=2-4;

q=0-4;

r=1-4;

s=1-6;

u=0-4 and v=0-4, wherein the sum of u+v is 2-4;

or a pharmaceutically acceptable salt thereof, provided that when $R_6$ is alkenyl of 2-7 carbon atoms or alkynyl of 2-7 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^+$, or —$NR_6(OR_6)$, then g=2-6;

when M is —O— and $R_7$ is —$OR_6$, then p=1-4;

when Y is —$NR_6$—, then k=2-4;

when Y is —O— and M or W is —O—, then k=1-4;

when W is not a bond with Het bonded through a nitrogen atom, then q=2-4;

and when W is a bond with Het bonded through a nitrogen atom and Y is —O— or —$NR_6$—, then k=2-4.]

[9. A pharmaceutical composition which comprises a compound of formula 1 having the structure

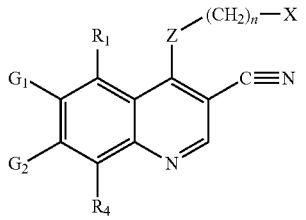

wherein:

X is cycloalkyl of 3 to 7 carbon atoms, which may be optionally substituted with one or more alkyl of 1 to 6 carbon atom groups; or is a pyridinyl, pyrimidinyl, or phenyl ring wherein the pyridinyl, pyrimidinyl, or phenyl ring may be optionally mono- di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalky of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, methylmercapto, and benzoylamino;

Z is —NH—, —O—, —S—, or —NR—;

R is alkyl of 1-6 carbon atoms, or carboalkyl of 2-7 carbon atoms;

$G_1$, $G_2$, $R_1$, and $R_4$ are each, independently, hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,

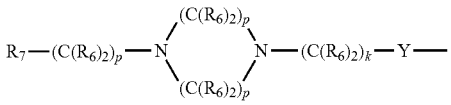

$R_8R_9$—CH—M—$(C(R_6)_2)_k$—Y—, $R_7$—$(C(R_6)_2)_g$—Y—, $R_7$—$(C(R_6)_2)_p$—M—$(C(R_6)_2)_k$—Y—, or Het-$(C(R_6)_2)_q$—W—$(C(R_6)_2)_k$—Y— with the proviso that either $G_1$ or $G_2$ or both $G_1$ and $G_2$ must be a radical selected from the group

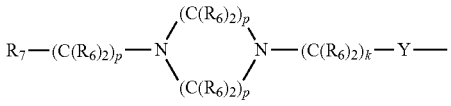

$R_8R_9$—CH—M—$(C(R_6)_2)_k$—Y—, R'$_7$—$(C(R_6)_2)_g$—Y—, $R_7$—$(C(R_6)_2)_p$—M—$(C(R_6)_2)_k$—Y—, Het-$(C(R_6)_2)_q$—W—$(C(R_6)_2)_k$—Y—, or $R_2$—$\overset{H}{N}$—;

Y is a divalent radical selected from the group consisting of

—$(CH_2)_a$—, —O—, and —$\underset{R_6}{N}$—;

$R_7$ is —$NR_6R_6$, -J, —$OR_6$, —$N(R_6)_3^+$, or —$NR_6(OR_6)$;

R'$_7$ is —$NR_6(OR_6)$, —$N(R_6)_3^+$, alkenoxy of 1-6 carbon atoms, alkynoxy of 1-6 carbon atoms, N-alkyl-N-alkenylamino of 4 to 12 carbon atoms, N,N-dialkenylamino of 6-12 carbon atoms, N-alkyl-N-alkynylamino of 4 to 12 carbon atoms, N-alkenyl-N-alkynylamino of 4 to 12 carbon atoms, or N,N-dialkynylamino of 6-12 carbon atoms with the proviso that the alkenyl or alkynyl moiety is bound to a nitrogen or oxygen atom through a saturated carbon atom;

M is $>NR_6$, —O—, $>N—(C(R_6)_2)_pNR_6R_6$, or $>N—(C(R_6)_2)_p—OR_6$,

W is $>NR_6$, —O— or is a bond;

Het is a heterocycle selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

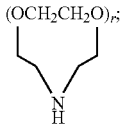

wherein the heterocycle is optionally mono- or di-substituted on carbon or nitrogen with $R_6$, optionally mono- or di-substituted on carbon with hydroxy, $—N(R_6)_2$, or $—OR_6$, optionally mono or di-substituted on carbon with the mono-valent radicals $—(C(R_6)_2)_sOR_6$ or $—(C(R_6)_2)_sN(R_6)_2$, or optionally mono or di-substituted on a saturated carbon with divalent radicals —O— or $—O(C(R_6)_2)_sO—$;

$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;

$R_2$, is selected from the group consisting of

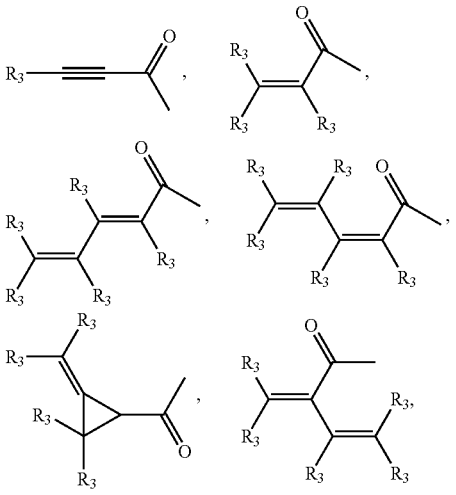

-continued

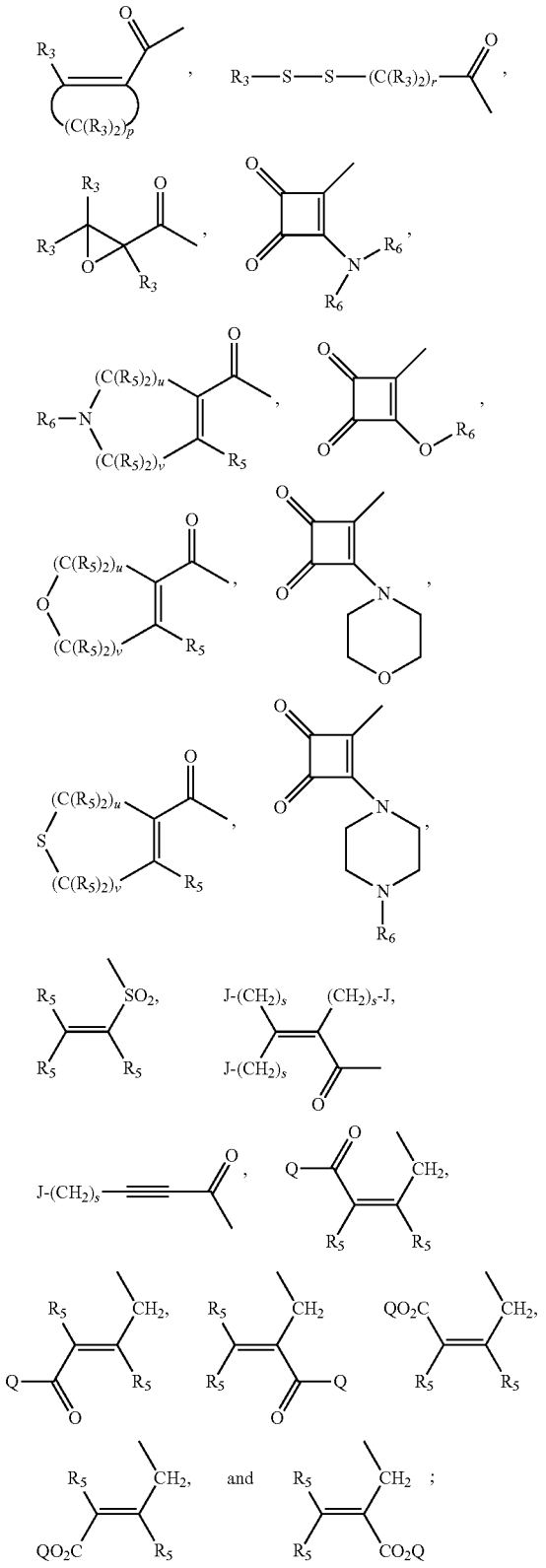

$R_3$ is independently hydrogen, alkyl of 1-6 carbon atoms, carboxy, carboalkoxy of 1-6 carbon atoms, phenyl, carboalkyl of 2-7 carbon atoms,

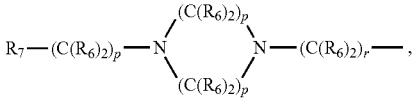

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

with the proviso that at least one of the $R_3$ groups is selected from the group

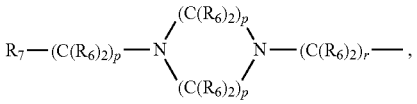

$R'_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

with the proviso that for said at least one $R_3$ group the moiety Het-$(C(R_6)_2)_q$—W—$(C(R_6)_2)_r$— cannot be morpholino-N-alkyl wherein the alkyl group is 1-6 carbon atoms, piperidino-N-alkyl wherein the alkyl group is 1-6 carbon atoms, N-alkyl piperidino-N-alkyl wherein either alkyl group is 1-6 carbon atoms, or azacycloalkyl-N-alkyl of 3-11 carbon atoms;

$R_5$ is independently hydrogen, alkyl of 1-6 carbon atoms, carboxy, carboalkoxy of 1-6 carbon atoms, phenyl, carboalkyl of 2-7 carbon atoms,

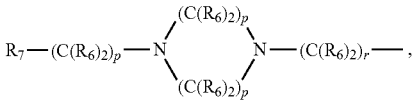

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_rNR_6R_6$, or —$(C(R_6)_2)_rOR_6$;

J is independently hydrogen, chlorine, fluorine, or bromine;

Q is alkyl of 1-6 carbon atoms or hydrogen;

a=0 or 1;

g=1-6;

k=0-4;

n is 0-1;

p=2-4;

q=0-4;

r=1-4;

s=1-6;

u=0-4 and v=0-4, wherein the sum of u+v is 2-4;

or a pharmaceutically acceptable salt thereof, provided that when $R_6$ is alkenyl of 2-7 carbon atoms or alkynyl of 2-7 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^+$, or —$NR_6(OR_6)$, then g=2-6;

when M is —O— and $R_7$ is -$OR_6$, then p=1-4;

when Y is —$NR_6$—, then k=2-4;

when Y is —O— and M or W is —O—, then k=1-4;

when W is not a bond with Het bonded through a nitrogen atom, then q=2-4;

and when W is a bond with Het bonded through a nitrogen atom and Y is —O— or —$NR_6$—, then k=2-4.]

*10. A compound having the structure:*

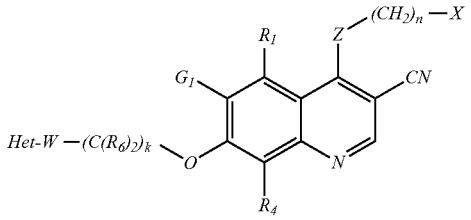

*wherein:*

*X is a phenyl ring, optionally mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino;*

*Z is —NH—;*

*$R_1$ and $R_4$ are each hydrogen;*

*$G_1$ is hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,*

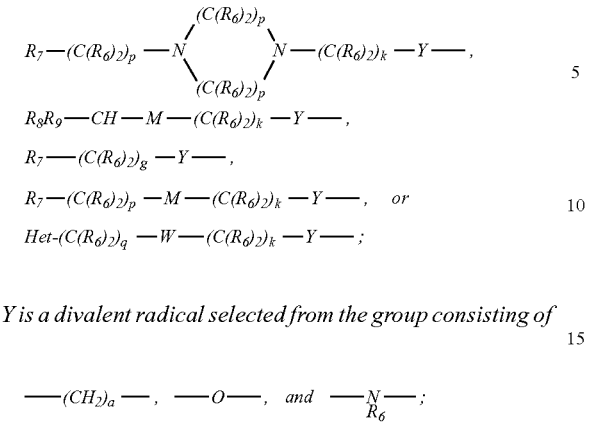

$R_7$—$(C(R_6)_2)_p$—N(—$(C(R_6)_2)_p$)—N(—$(C(R_6)_2)_k$—Y—), $R_8R_9$—CH—M—$(C(R_6)_2)_k$—Y—, $R_7$—$(C(R_6)_2)_g$—Y—, $R_7$—$(C(R_6)_2)_p$—M—$(C(R_6)_2)_k$—Y—, or

Het-$(C(R_6)_2)_q$—W—$(C(R_6)_2)_k$—Y—;

*Y is a divalent radical selected from the group consisting of*

—$(CH_2)_a$—, —O—, and —N($R_6$)—;

$R_7$ is —$NR_6R_6$, —J, —$OR_6$, —$N(R_6)_3^{\pm}$, or —$NR_6(OR_6)$;

M is —$N(R_6)$—, —O—, —$N[(C(R_6)_2)_pNR_6R_6]$—, or —$N[(C(R_6)_2)_p$—$OR_6]$—;

W is —$N(R_6)$—, —O—, or is a bond;

Het is a heterocycle selected from the group consisting of pyridine, 2,6-disubstituted morpholine, 2,5-disubstituted thiomorpholine, 2-substituted imidazole, substituted thiazole, thiazolidine, N-substituted imidazole, N-substituted 1,4-piperazine, N-substituted piperidine, dioxane, 1,3-dioxolane, and N-substituted pyrrolidine, wherein the heterocycle is optionally mono-or di-substituted on carbon or nitrogen with $R_6$, optionally mono- or di-substituted on carbon with hydroxy, —$N(R_6)_2$, or —$OR_6$, optionally mono-or di-substituted on carbon with the mono-valent radicals —$(C(R_6)_2)_sOR_6$ or —$(C(R_6)_2)_sN(R_6)_2$, or optionally mono-or di-substituted on a saturated carbon with divalent radicals —O— or —$O(C(R_6)_2)_sO$—;

$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;

$R_8$ and $R_9$ are each, independently, —$(C(R_6)_2)_rNR_6R_6$, or —$(C(R_6)_2)_rOR_6$;

J is independently hydrogen, chlorine, fluorine, or bromine;

a=0 or 1;

g=1-6;

k=0-4;

n is 0;

p=2-4;

q=0-4;

r=1-4; and s=1-6;

or a pharmaceutically acceptable salt thereof, provided that when $R_6$ is alkenyl of 2-6 carbon atoms or alkynyl of 2-6 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^{\pm}$, or —$NR_6(OR_6)$, then g=2-6;

when M is —O— and $R_7$ is —$OR_6$, then p=1-4;

when Y is —$NR_6$—, then k=2-4;

when Y is —O— and M or W is —O—, then k=1-4;

when W is not a bond with Het bonded through a nitrogen atom, then q=2-4;

and when W is a bond with Het bonded through a nitrogen atom and Y is —O— or —$NR_6$—, then k=2-4.

11. A compound having the structure:

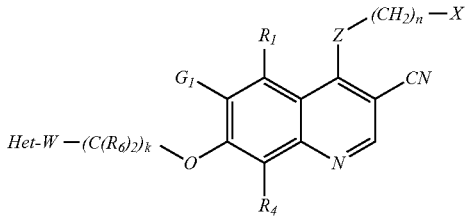

wherein:

X is a phenyl ring, optionally mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino;

Z is —NH—;

$R_1$ and $R_4$ are each hydrogen;

$G_1$ is hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,

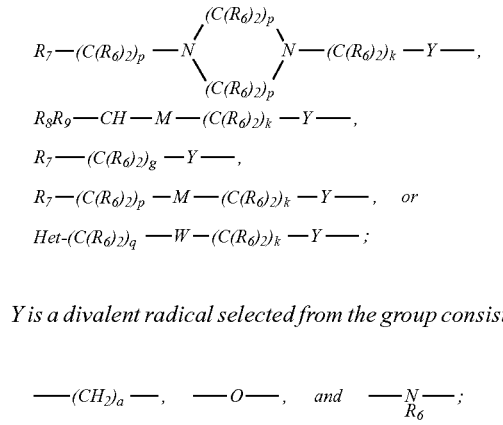

$R_7$—$(C(R_6)_2)_p$—N(—$(C(R_6)_2)_p$)—N—$(C(R_6)_2)_k$—Y—, $R_8R_9$—CH—M—$(C(R_6)_2)_k$—Y—, $R_7$—$(C(R_6)_2)_g$—Y—, $R_7$—$(C(R_6)_2)_p$—M—$(C(R_6)_2)_k$—Y—, or

Het-$(C(R_6)_2)_q$—W—$(C(R_6)_2)_k$—Y—;

Y is a divalent radical selected from the group consisting of

—$(CH_2)_a$—, —O—, and —N($R_6$)—;

$R_7$ is —$NR_6R_6$, —J, —$OR_6$, —$N(R_6)_3^{\pm}$, or —$NR_6(OR_6)$;

M is —N($R_6$)—, —O—, —N[$(C(R_6)_2)_pNR_6R_6$]—, or —N[$(C(R_6)_2)_p$—$OR_6$]—;

W is —N($R_6$)—, —O—, or is a bond;

Het is N-substituted 1,4-piperazine;

wherein Het is optionally mono-or di-substituted on carbon or nitrogen with $R_6$, optionally mono-or di-substituted on carbon with hydroxy, —$N(R_6)_2$, or —$OR_6$, optionally mono-or di-substituted on carbon with the mono-valent radicals —$(C(R_6)_2)_sOR_6$ or —$(C(R_6)_2)_sN(R_6)_2$, or optionally mono-or di-substituted on a saturated carbon with divalent radicals —O— or —$O(C(R_6)_2)_sO$—;

$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;

$R_8$ and $R_9$ are each, independently, —$(C(R_6)_2)_rNR_6R_6$, or —$(C(R_6)_2)_rOR_6$;

J is independently hydrogen, chlorine, fluorine, or bromine;

a=0 or 1;

g=1-6;

k=0-4;

n is 0;

p=2-4;

q=0-4;

r=1-4; and s=1-6;

or a pharmaceutically acceptable salt thereof, provided that when $R_6$ is alkenyl of 2-6 carbon atoms or alkynyl of 2-6 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^{\pm}$, or —$NR_6(OR_6)$, then g=2-6;

when M is —O— and $R_7$ is —$OR_6$, then p=1-4;

when Y is —$NR_6$—, then k=2-4;

when Y is —O— and M or W is —O—, then k=1-4;

when W is not a bond with Het bonded through a nitrogen atom, then q=2-4;

and when W is a bond with Het bonded through a nitrogen atom and Y is —O— or —$NR_6$—, then k=2-4.

12. A compound having the structure:

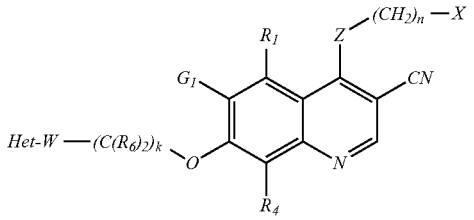

wherein:

X is a phenyl ring tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino;

Z is —NH—;

$R_1$ and $R_4$ are each hydrogen;

$G_1$ is hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkenylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,

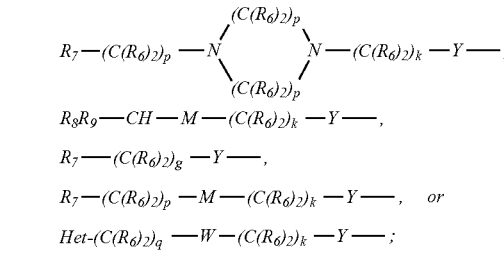

$R_7$—$(C(R_6)_2)_p$—N(—$(C(R_6)_2)_p$)—N—$(C(R_6)_2)_k$—Y—, $R_8R_9$—CH—M—$(C(R_6)_2)_k$—Y—, $R_7$—$(C(R_6)_2)_g$—Y—, $R_7$—$(C(R_6)_2)_p$—M—$(C(R_6)_2)_k$—Y—, or

Het-$(C(R_6)_2)_q$—W—$(C(R_6)_2)_k$—Y—;

Y is a divalent radical selected from the group consisting of

—$(CH_2)_a$—, —O—, and —N($R_6$)—;

$R_7$ is —$NR_6R_6$, —J, —$OR_6$, —$N(R_6)_3^{\pm}$, or —$NR_6(OR_6)$;

M is —$M(R_6)$—, —O—, —$N[(C(R_6)_2)_pNR_6R_6]$—, or $N[(C(R_6)_2)_p$—$OR_6]$—;

W is —$N(R_6)$—, —O—, or is a bond;

Het is a heterocycle selected from the group consisting of pyridine, 2,6-disubstituted morpholine, 2,5-disubstituted thiomorpholine, 2-substituted imidazole, substituted thiazole, thiazolidine, N-substituted imidazole, N-substituted 1,4-piperazine, N-substituted piperidine, dioxane, 1,3-dioxolane, and N-substituted pyrrolidine; wherein the heterocycle is optionally mono-or di-substituted on carbon or nitrogen with $R_6$, optionally mono-or di-substituted on carbon with hydroxy, —$N(R_6)_2$, or —$OR_6$, optionally mono-or di-substituted on carbon with the mono-valent radicals —$(C(R_6)_2)_sOR_6$ or —$(C(R_6)_2)_sN(R_6)_2$, or optionally mono-or di-substituted on a saturated carbon with divalent radicals —O— or —$O(C(R_6)_2)_sO$—;

$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;

$R_8$ and $R_9$ are each, independently, —$(C(R_6)_2)_rNR_6R_6$, or —$(C(R_6)_2)_rOR_6$;

J is independently hydrogen, chlorine, fluorine, or bromine;

a=0 or 1;

g=1-6;

k=0-4;

n is 0;

p=2-4;

q=0-4;

r=1-4; and s=1-6;

or a pharmaceutically acceptable salt thereof, provided that when $R_6$ is alkenyl of 2-6 carbon atoms or alkynyl of 2-6 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^{\pm}$, or —$NR_6(OR_6)$, then g=2-6;

when M is —O— and $R_7$ is —$OR_6$, then p=1-4;

when Y is —$NR_6$—, then k=2-4;

when Y is —O— and M or W is —O—, then k=1-4;

when W is not a bond with Het bonded through a nitrogen atom, then q=2-4;

and when W is a bond with Het bonded through a nitrogen atom and Y is —O— or —$NR_6$—, then k=2-4.

13. The compound according to claim 12, wherein Het is N-substituted 1,4-piperazine, or a pharmaceutically acceptable salt thereof.

14. A compound having the structure:

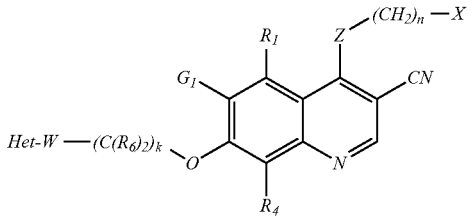

wherein:

X is a phenyl ring optionally mono-, di-, or tri-substituted with a halogen;

Z is —NH—;

$R_1$ and $R_4$ are each hydrogen;

$G_1$ is hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino, $$R_7-(C(R_6)_2)_p-N\begin{matrix}(C(R_6)_2)_p\\(C(R_6)_2)_p\end{matrix}N-(C(R_6)_2)_k-Y-,$$

$$R_8R_9-CH-M-(C(R_6)_2)_k-Y-,$$

$$R_7-(C(R_6)_2)_g-Y-,$$

$$R_7-(C(R_6)_2)_p-M-(C(R_6)_2)_k-Y-, \quad or$$

$$Het\text{-}(C(R_6)_2)_q-W-(C(R_6)_2)_k-Y-;$$

*Y is a divalent radical selected from the group consisting of*

$$-(CH_2)_a-, \quad -O-, \quad and \quad -\underset{R_6}{N}-;$$

$R_7$ *is* $-NR_6R_6$, $-J$, $-OR_6$, $-N(R_6)_3^{\pm}$, *or* $-NR_6(OR_6)$;

*M is* $-N(R_6)-$, $-O-$, $-N[(C(R_6)_2)_pNR_6R_6]-$, *or* $-N[(C(R_6)_2)_p-OR_6]-$;

*W is* $-N(R_6)-$, $-O-$, *or is a bond;*

*Het is a heterocycle selected from the group consisting of pyridine, 2,6-disubstituted morpholine, 2,5-disubstituted thiomorpholine, 2-substituted imidazole, substituted thiazole, thiazolidine, N-substituted imidazole, N-substituted 1,4-piperazine, N-substituted piperidine, dioxane, 1,3-dioxolane, and N-substituted pyrrolidine; wherein the heterocycle is optionally mono-or di-substituted on carbon or nitrogen with* $R_6$, *optionally mono-or di-substituted on carbon with hydroxy,* $-N(R_6)_2$, *or* $-OR_6$, *optionally mono-or di-substituted on carbon with the mono-valent radicals* $-(C(R_6)_2)_sOR_6$ *or* $-(C(R_6)_2)_sN(R_6)_2$, *or optionally mono-or di-substituted on a saturated carbon with divalent radicals* $-O-$ *or* $-O(C(R_6)_2)_sO-$;

$R_6$ *is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;*

$R_8$ *and* $R_9$ *are each, independently,* $-(C(R_6)_2)_rNR_6R_6$, *or* $-(C(R_6)_2)_rOR_6$;

*J is independently hydrogen, chlorine, fluorine, or bromine;*

*a=0 or 1;*

*g=1-6;*

*k=0-4;*

*n is 0;*

*p=2-4;*

*q=0-4;*

*r=1-4; and*

*s=1-6;*

*or a pharmaceutically acceptable salt thereof, provided that*

*when* $R_6$ *is alkenyl of 2-6 carbon atoms or alkynyl of 2-6 carbon atoms, such alkenyl or alkynyl moiety is bound to a nitrogen or oxygen atom through a saturated carbon atom;*

*and further provided that*

*when Y is* $-NR_6-$ *and* $R_7$ *is* $-NR_6R_6$, $-N(R_6)_3^{\pm}$, *or* $-NR_6(OR_6)$, *then g=2-6;*

*when M is —O— and* $R_7$ *is* $-OR_6$, *then p=1-4;*

*when Y is* $-NR_6-$, *then k=2-4;*

*when Y is —O— and M or W is —O—, then k=1-4;*

*when W is not a bond with Het bonded through a nitrogen atom, then q=2-4;*

*and when W is a bond with Het bonded through a nitrogen atom and Y is —O— or* $-NR_6-$, *then k=2-4.*

*15. The compound according to claim 14, wherein X is a phenyl ring optionally mono-, di-, or tri-substituted with chloro, or a pharmaceutically acceptable salt thereof.*

*16. The compound according to claim 14, wherein Het is N-substituted 1,4-piperazine, or a pharmaceutically acceptable salt thereof.*

*17. A compound having the structure:*

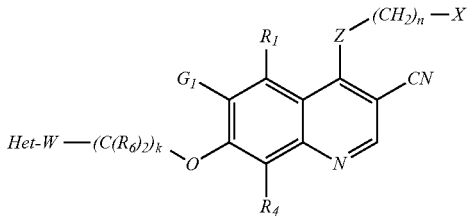

*wherein:*

*X is a phenyl ring optionally mono-, di-, or tri-substituted with an alkoxy of 1-6 carbons;*

*Z is —NH—;*

$R_1$ *and* $R_4$ *are each hydrogen;*

$G_1$ *is hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of 1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,*

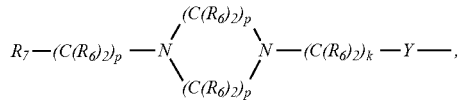

$R_7$—$(C(R_6)_2)_p$—N(—$(C(R_6)_2)_p$)—N(—$(C(R_6)_2)_p$)—$(C(R_6)_2)_k$—Y—, $R_8R_9$—CH—M—$(C(R_6)_2)_k$—Y—, $R_7$—$(C(R_6)_2)_g$—Y—, $R_7$—$(C(R_6)_2)_p$—M—$(C(R_6)_2)_k$—Y—, or

Het-$(C(R_6)_2)_q$—W—$(C(R_6)_2)_k$—Y—;

*Y is a divalent radical selected from the group consisting of*

—$(CH_2)_a$—, —O—, and —N($R_6$)—;

*$R_7$ is —$NR_6R_6$, —J, —$OR_6$, —$N(R_6)_3^{\pm}$, or —$NR_6(OR_6)$;*

*M is —$N(R_6)$—, —O—, —$N[(C(R_6)_2)_pNR_6R_6]$—, or —$N[(C(R_6)_2)_p$—$OR_6]$—;*

*W is —$N(R_6)$—, —O— or is a bond;*

*Het is a heterocycle selected from the group consisting of pyridine, 2,6-disubstituted morpholine, 2,5-disubstituted thiomorpholine, 2-substituted imidazole, substituted thiazole, thiazolidine, N-substituted imidazole, N-substituted 1,4-piperazine, N-substituted piperidine, dioxane, 1,3-dioxolane, and N-substituted pyrrolidine; wherein the heterocycle is optionally mono-or di-substituted on carbon or nitrogen with $R_6$, optionally mono- or di-substituted on carbon with hydroxy, —$N(R_6)_2$, or —$OR_6$, optionally mono-or di-substituted on carbon with the mono-valent radicals —$(C(R_6)_2)_sOR_6$ or —$(C(R_6)_2)_sN(R_6)_2$, or optionally mono-or di-substituted on a saturated carbon with divalent radicals —O— or —$O(C(R_6)_2)_sO$—;*

*$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;*

*$R_8$ and $R_9$ are each, independently, —$(C(R_6)_2)_rNR_6R_6$, or —$(C(R_6)_2)_rOR_6$;*

*J is independently hydrogen, chlorine, fluorine, or bromine;*

*a=0 or 1;*

*g=1-6;*

*k=0-4;*

*n is 0;*

*p=2-4;*

*q=0-4;*

*r=1-4; and*

*s=1-6;*

*or a pharmaceutically acceptable salt thereof, provided that*

*when $R_6$ is alkenyl of 2-6 carbon atoms or alkynyl of 2-6 carbon atoms, such alkenyl or alkynyl moiety is bound to a nitrogen or oxygen atom through a saturated carbon atom;*

*and further provided that*

*when Y is —$NR_6$— and $R_7$ is —$NR_6R_6$, —$N(R_6)_3^{\pm}$, or —$NR_6(OR_6)$, then g=2-6;*

*when M is —O— and $R_7$ is —$OR_6$, then p=1-4;*

*when Y is —$NR_6$—, then k=2-4;*

*when Y is —O— and M or W is —O—, then k=1-4;*

*when W is not a bond with Het bonded through a nitrogen atom, then q=2-4;*

*and when W is a bond with Het bonded through a nitrogen atom and Y is —O— or —$NR_6$—, then k=2-4.*

*18. The compound according to claim 17, wherein X is a phenyl ring optionally mono-, di-, or tri-substituted with methoxy, or a pharmaceutically acceptable salt thereof.*

*19. The compound according to claim 17, wherein Het is N-substituted 1,4-piperazine, or a pharmaceutically acceptable salt thereof.*

*20. A compound having the structure:*

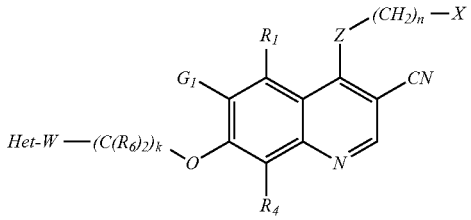

*wherein:*

*X is a phenyl ring, optionally mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino;*

*Z is —NH—;*

*$R_1$ and $R_4$ are each hydrogen;*

*$G_1$ is hydrogen, halogen, alkyl of 1-6 carbon atoms, alkenyl of 2-6 carbon atoms, alkynyl of 2-6 carbon atoms, alkenyloxy of 2-6 carbon atoms, alkynyloxy of 2-6 carbon atoms, hydroxymethyl, halomethyl, alkanoyloxy of 1-6 carbon atoms, alkenoyloxy of 3-8 carbon atoms, alkynoyloxy of 3-8 carbon atoms, alkanoyloxymethyl of 2-7 carbon atoms, alkenoyloxymethyl of 4-9 carbon atoms, alkynoyloxymethyl of 4-9 carbon atoms, alkoxymethyl of 2-7 carbon atoms, alkoxy of 1-6 carbon atoms, alkylthio of 1-6 carbon atoms, alkylsulphinyl of*

1-6 carbon atoms, alkylsulphonyl of 1-6 carbon atoms, alkylsulfonamido of 1-6 carbon atoms, alkenylsulfonamido of 2-6 carbon atoms, alkynylsulfonamido of 2-6 carbon atoms, hydroxy, trifluoromethyl, trifluoromethoxy, cyano, nitro, carboxy, carboalkoxy of 2-7 carbon atoms, carboalkyl of 2-7 carbon atoms, phenoxy, phenyl, thiophenoxy, benzyl, amino, hydroxyamino, alkoxyamino of 1-4 carbon atoms, alkylamino of 1-6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6-12 carbon atoms, phenylamino, benzylamino,

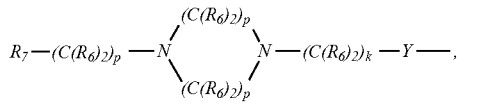

$R_8R_9$—CH—M—$(C(R_6)_2)_k$—Y—, $R_7$—$(C(R_6)_2)_g$—Y—, $R_7$—$(C(R_6)_2)_p$—M—$(C(R_6)_2)_k$—Y—, or

Het-$(C(R_6)_2)_q$—W—$(C(R_6)_2)_k$—Y—;

Y is a divalent radical selected from the group consisting of

—$(CH_2)_a$—, —O—, and —N(R$_6$)—;

$R_7$ is —$NR_6R_6$, —J, —$OR_6$, —$N(R_6)_3^{\pm}$, or —$NR_6(OR_6)$;

M is —N($R_6$)—, —O—, —N[$(C(R_6)_2)_pNR_6R_6$]—, or —N[$(C(R_6)_2)_p$—$OR_6$]—;

W is —N($R_6$)—, —O—, or is a bond;

Het is a piperazine optionally mono-or di-substituted on carbon or nitrogen with $R_6$, optionally mono-or di-substituted on carbon with hydroxy, —$N(R_6)_2$, or —$OR_6$, optionally mono-or di-substituted on carbon with the mono-valent radicals —$(C(R_6)_2)_sOR_6$ or —$(C(R_6)_2)_sN(R_6)_2$, or optionally mono-or di-substituted on a saturated carbon with divalent radicals —O— or —O($C(R_6)_2)_s$O—;

$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;

$R_8$ and $R_9$ are each, independently, —$(C(R_6)_2)_rNR_6R_6$, or —$(C(R_6)_2)_rOR_6$;

J is independently hydrogen, chlorine, fluorine, or bromine;

a=0 or 1;

g=1-6;

k=0-4;

n is 0;

p=2-4;

q=0-4;

r=1-4; and s=1-6;

or a pharmaceutically acceptable salt thereof, provided that when $R_6$ is alkenyl of 2-6 carbon atoms or alkynyl of 2-6 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^{\pm}$, or —$NR_6(OR_6)$, then g=2-6;

when M is —O— and $R_7$ is —$OR_6$, then p=1-4;

when Y is —$NR_6$—, then k=2-4;

when Y is —O— and M or W is —O—, then k=1-4;

when W is not a bond with Het bonded through a nitrogen atom, then q=2-4;

and when W is a bond with Het bonded through a nitrogen atom and Y is —O— or —$NR_6$—, then k=2-4.

21. The compound according to claim 20, wherein X is a tri-substituted phenyl ring, or a pharmaceutically acceptable salt thereof.

22. The compound according to claim 20, wherein X is a phenyl ring optionally mono-, di-, or tri-substituted with a halogen, or a pharmaceutically acceptable salt thereof.

23. The compound according to claim 22, wherein X is a phenyl ring optionally mono-, di-, or tri-substituted with chloro, or a pharmaceutically acceptable salt thereof.

24. The compound according to claim 20, wherein X is a phenyl ring optionally mono-, di-, or tri-substituted with an alkoxy of 1-6 carbons, or a pharmaceutically acceptable salt thereof.

25. The compound according to claim 24, wherein X is a phenyl ring optionally mono-, di-, or tri-substituted with methoxy, or a pharmaceutically acceptable salt thereof.

26. The compound according to claim 20, wherein $G_1$ is alkoxy of 1-6 carbons, or a pharmaceutically acceptable salt thereof.

27. The compound according to claim 26, wherein $G_1$ is methoxy, or a pharmaceutically acceptable salt thereof.

28. A compound having the structure:

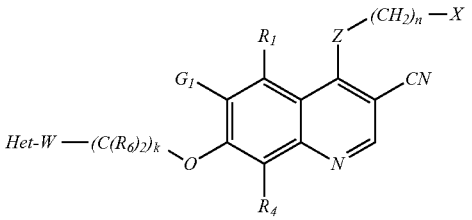

wherein:

X is a phenyl ring, optionally mono-, di-, or tri-substituted with a substituent selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino,

*benzylamino, alkanoylamino of 1-6 carbon atoms, alkenoylamino of 3-8 carbon atoms, alkynoylamino of 3-8 carbon atoms, carboxyalkyl of 2-7 carbon atoms, carboalkoxyalkyl of 3-8 carbon atoms, aminoalkyl of 1-5 carbon atoms, N-alkylaminoalkyl of 2-9 carbon atoms, N,N-dialkylaminoalkyl of 3-10 carbon atoms, N-alkylaminoalkoxy of 2-9 carbon atoms, N,N-dialkylaminoalkoxy of 3-10 carbon atoms, mercapto, and benzoylamino;*

*Z is —NH—;*

*$R_1$ and $R_4$ are each hydrogen;*

*$G_1$ is alkoxy of 1-6 carbons;*

*W is —N($R_6$)—, —O—, or is a bond;*

*Het is a heterocycle selected from the group consisting of pyridine, 2,6-disubstituted morpholine, 2,5-disubstituted thiomorpholine, 2-substituted imidazole, substituted thiazole, thiazolidine, N-substituted imidazole, N-substituted 1,4-piperazine, N-substituted piperidine, dioxane, 1,3-dioxolane, and N-substituted pyrrolidine; wherein the heterocycle is optionally mono-or di-substituted on carbon or nitrogen with $R_6$, optionally mono- or di-substituted on carbon with hydroxy, —N($R_6$)$_2$, or —O$R_6$, optionally mono-or di-substituted on carbon with the mono-valent radicals —(C($R_6$)$_2$)$_s$O$R_6$ or —(C($R_6$)$_2$)$_s$N($R_6$)$_2$, or optionally mono-or di-substituted on a saturated carbon with divalent radicals —O— or —O(C($R_6$)$_2$)$_s$O—;*

*$R_6$ is hydrogen, alkyl of 1-6 carbon atoms, alkenyl of 2-6 carbon atoms, alkynyl of 2-6 carbon atoms, cycloalkyl of 1-6 carbon atoms, carboalkyl of 2-7 carbon atoms, carboxyalkyl (2-7 carbon atoms), phenyl, or phenyl optionally substituted with one or more halogen, alkoxy of 1-6 carbon atoms, trifluoromethyl, amino, alkylamino of 1-3 carbon atoms, dialkylamino of 2-6 carbon atoms, nitro, cyano, azido, halomethyl, alkoxymethyl of 2-7 carbon atoms, alkanoyloxymethyl of 2-7 carbon atoms, alkylthio of 1-6 carbon atoms, hydroxy, carboxyl, carboalkoxy of 2-7 carbon atoms, phenoxy, phenyl, thiophenoxy, benzoyl, benzyl, phenylamino, benzylamino, alkanoylamino of 1-6 carbon atoms, or alkyl of 1-6 carbon atoms;*

*k=0-4;*

*n is 0; and*

*s=1-6;*

*or a pharmaceutically acceptable salt thereof,*

*provided that*

*when $R_6$ is alkenyl of 2-6 carbon atoms or alkynyl of 2-6 carbon atoms, such alkenyl or alkynyl moiety is bound to a nitrogen or oxygen atom through a saturated carbon atom.*

*29. The compound according to claim 28, wherein Het is N-substituted 1,4-piperazine, or a pharmaceutically acceptable salt thereof.*

*30. The compound according to claim 29, wherein X is a tri-substituted phenyl ring, or a pharmaceutically acceptable salt thereof.*

*31. The compound according to claim 29, wherein X is a phenyl ring optionally mono-, di-, or tri-substituted with a halogen, or a pharmaceutically acceptable salt thereof.*

*32. The compound according to claim 31, wherein X is a phenyl ring optionally mono-, di-, or tri-substituted with chloro, or a pharmaceutically acceptable salt thereof.*

*33. The compound according to claim 29, wherein X is a phenyl ring optionally mono-, di-, or tri-substituted with an alkoxy of 1-6 carbons, or a pharmaceutically acceptable salt thereof.*

*34. The compound according to claim 33, wherein X is a phenyl ring optionally mono-, di-, or tri-substituted with methoxy, or a pharmaceutically acceptable salt thereof.*

*35. The compound according to any one of claims 28 to 34, wherein $G_1$ is methoxy, or a pharmaceutically acceptable salt thereof.*

*36. The compound according to any one of claims 10 to 34, wherein W is a bond, or a pharmaceutically acceptable salt thereof.*

*37. The compound according to any one of claims 10 to 34, wherein W is a bond, Het is bonded through a nitrogen atom, and k is 2 to 4, or a pharmaceutically acceptable salt thereof.*

*38. The compound according to any one of claims 10 to 34, wherein k is 3, or a pharmaceutically acceptable salt thereof.*

*39. A pharmaceutical composition which comprises a compound of any one of claim 5 or 10-34 or a pharmaceutically acceptable salt thereof.*

*40. A pharmaceutical composition which comprises a compound of claim 35 or a pharmaceutically acceptable salt thereof.*

*41. A pharmaceutical composition which comprises a compound of claim 36 or a pharmaceutically acceptable salt thereof.*

*42. A pharmaceutical composition which comprises a compound of claim 37 or a pharmaceutically acceptable salt thereof.*

*43. A pharmaceutical composition which comprises a compound of claim 38 or a pharmaceutically acceptable salt thereof.*

* * * * *